(12) United States Patent
Miltz et al.

(10) Patent No.: US 8,748,435 B2
(45) Date of Patent: Jun. 10, 2014

(54) PYRAZOLO PYRIMIDINE DERIVATIVES

(75) Inventors: Wolfgang Miltz, Basel (CH); Berndt Oberhauser, Riehen (CH); Andrea Vaupel, Riehen (CH); Juraj Velcicky, Basel (CH); Klaus Weigand, Bettingen (CH); Rajender Reddy Leleti, Randolph, NJ (US); Yugang Liu, Bridgewater, NJ (US); Zhengming Du, Parsippany, NJ (US)

(73) Assignee: Novartis AG, Basel (CH)

( * ) Notice: Subject to any disclaimer, the term of this patent is extended or adjusted under 35 U.S.C. 154(b) by 71 days.

(21) Appl. No.: 13/429,726

(22) Filed: Mar. 26, 2012

(65) Prior Publication Data

US 2012/0252778 A1 Oct. 4, 2012

Related U.S. Application Data

(60) Provisional application No. 61/470,630, filed on Apr. 1, 2011.

(51) Int. Cl.
*A01N 43/90* (2006.01)
*A61K 31/519* (2006.01)
*C07D 487/00* (2006.01)

(52) U.S. Cl.
USPC ........................ 514/259.3; 544/281

(58) Field of Classification Search
None
See application file for complete search history.

(56) References Cited

U.S. PATENT DOCUMENTS

| | | |
|---|---|---|
| 2002/0041880 A1 | 4/2002 | DeFeo-Jones et al. |
| 2006/0089362 A1 | 4/2006 | Seno et al. |
| 2006/0239999 A1 | 10/2006 | Saki et al. |
| 2006/0252679 A1 | 11/2006 | Saki et al. |
| 2010/0152205 A1 | 6/2010 | Hunt et al. |
| 2011/0081337 A1 | 4/2011 | Yang |

FOREIGN PATENT DOCUMENTS

| | | |
|---|---|---|
| DE | 4333705 C2 | 4/1995 |
| EP | 0490587 A1 | 6/1992 |
| FR | 2690442 A1 | 10/1993 |
| JP | 6009638 | 1/1994 |
| WO | 9854093 | 12/1998 |
| WO | 0204424 A1 | 1/2002 |
| WO | 0224222 A2 | 3/2002 |
| WO | 03096025 A1 | 11/2003 |
| WO | 2006074041 A2 | 7/2006 |
| WO | 2007013673 A1 | 2/2007 |
| WO | 2008008539 A2 | 1/2008 |
| WO | 2008071771 A2 | 6/2008 |
| WO | 2009017954 A1 | 2/2009 |
| WO | 2009023179 A2 | 2/2009 |
| WO | 2009144201 A1 | 3/2009 |
| WO | 2010086040 A1 | 8/2010 |

*Primary Examiner* — Jeffrey H Murray
(74) *Attorney, Agent, or Firm* — Sophie Binet Cross

(57) ABSTRACT

The present invention relates to pyrazolo pyrimidine derivatives, to methods of preparing these, to combinations and pharmaceutical composition comprising these, and to their use in the treatment of diseases and disorders which may for example involve autoimmune diseases, angiogenesis, pain, and/or inflammatory diseases.

12 Claims, No Drawings

PYRAZOLO PYRIMIDINE DERIVATIVES

This application claims benefit under 35 U.S.C. §119(e) of U.S. Provisional Application No. 61/1470630, filed Apr. 1, 2011; the contents of which is incorporated herein by reference in their entirety.

The present invention relates to pyrazolo pyrimidine derivatives, to methods of preparing these, to combinations and pharmaceutical composition comprising these, and to their use in the treatment of diseases and disorders which may for example involve autoimmune diseases, angiogenesis, pain, and/or inflammatory diseases.

BACKGROUND

There is a need for new and innovative approaches for the treatment of rheumatoid arthritis and other autoimmune diseases, since there are still no ideal treatments available. Moreover, it appears that the GPR4 receptor might be associated with the autoimmune system.

Therefore, the present invention addresses the GPR4 receptor interaction with low molecular weight compounds, especially with selective GPR4 compounds, especially with GPR4 receptor antagonists. This approach may provide an innovative path for treating diseases or disorders involving the autoimmune system, such as by way of example, treatment of pain in particular in association with inflammatory processes, treatment of inflammatory diseases or disorders, or treatment of diseases or disorders involving angiogenesis.

PRIOR ART

WO2009/144201 describes imidazopyridine derivatives which may be effective in the treatment of a disease or disorder being associated with GPR4 receptor interaction.

The present invention describes in one embodiment a compound of formula (I) or a pharmaceutically acceptable salt thereof,

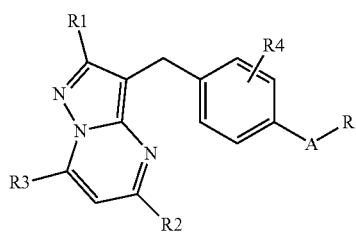

(I)

wherein

R1 is H or $C_1$-$C_6$ alkyl;

R2 and R3 are independently from each other H or $C_1$-$C_6$ alkyl;

A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—,

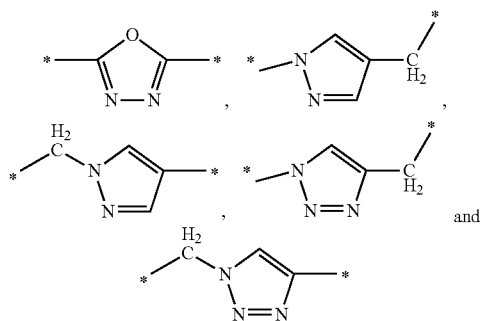

(wherein a * denote the link (or places of attachment));

R stands for heterocyclyl or cycloalkyl, each of which may be optionally substituted 1 to 4 times; and R4 is H, $C_1$-$C_6$ alkyl, $C_1$-$C_6$ alkoxy, halogen, hydroxy, cyano or trifluoromethyl.

The present invention describes in another embodiment a compound of formula (I') or a pharmaceutically acceptable salt thereof,

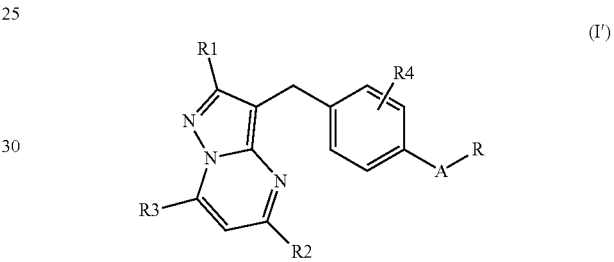

(I')

wherein

R1 is H or $C_1$-$C_6$ alkyl;

R2 and R3 are independently from each other H or $C_1$-$C_6$ alkyl;

A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—,

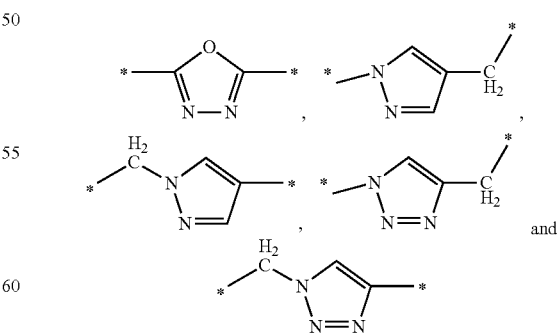

(wherein a * denote the link (or places of attachment));

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, $C_1$-$C_6$ alkoxycarbonyl or tri-$C_1$-$C_6$ alkyl silyloxy; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H, $C_1$-$C_6$ alkyl, $C_1$-$C_6$ alkoxy, halogen, hydroxy, cyano or trifluoromethyl.

Compounds of the invention, e.g. compounds of formula (I) or salts thereof, in particular pharmaceutically acceptable salts thereof, may modulate GPR4 efficacy, for example as antagonists.

In another embodiment the invention relates to a compound of formula (I'') or a pharmaceutically acceptable salt thereof,

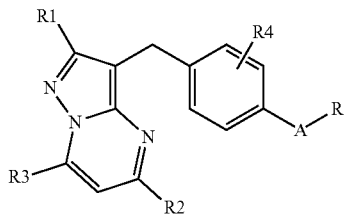

(I'')

wherein

R1 is H or $C_1$-$C_6$ alkyl;

R2 and R3 are independently from each other H or $C_1$-$C_6$ alkyl;

A is a bivalent linking group selected from the group consisting of:

—CH=CH—, —CH=CH—CH$_2$—, —CH$_2$—CH$_2$—CH$_2$—, —CH=CH—C(O)—, —CH$_2$—CH$_2$—C(O)—, —C(O)—NH—CH$_2$—, —O—CH$_2$—, —O—CH$_2$—CH$_2$—,

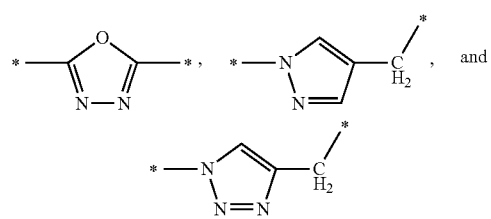

(wherein a * denote the link (or places of attachment));

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, $C_1$-$C_6$ alkoxycarbonyl or tri-$C_1$-$C_6$ alkyl silyloxy; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

In another embodiment the invention relates to a compound of formula (II) or a pharmaceutically acceptable salt thereof,

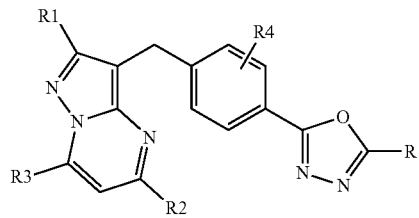

(II)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

In another embodiment the invention relates to a compound of formula (III) or a pharmaceutically acceptable salt thereof,

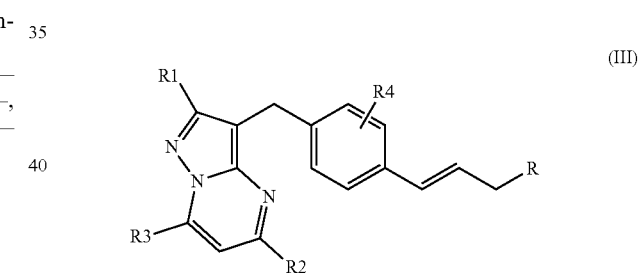

(III)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

In another embodiment the invention relates to a compound of formula (IV) or a pharmaceutically acceptable salt thereof,

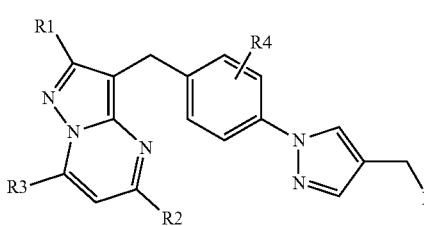

(IV)

wherein
R1 is H or $C_1$-$C_6$ alkyl;
R2 and R3 are independently from each other H or $C_1$-$C_6$ alkyl;
R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and
R4 is H or $C_1$-$C_6$ alkyl.

In another embodiment the invention relates to a compound of formula (V) or a pharmaceutically acceptable salt thereof,

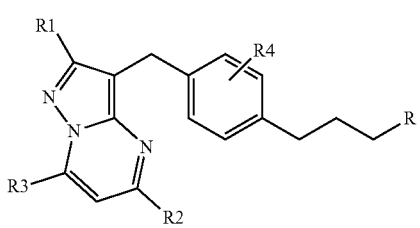

(V)

wherein
R1 is H or $C_1$-$C_6$ alkyl;
R2 and R3 are independently from each other H or $C_1$-$C_6$ alkyl;
R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and
R4 is H or $C_1$-$C_6$ alkyl.

In another embodiment the invention relates to compounds in accordance to the foregoing formulae (I), (I'), (I"), (II), (III), (IV) and/or (V), or a pharmaceutically acceptable salt thereof, wherein R is selected from piperidine and piperazine each of which may be optionally substituted one or more times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; or tetrazole optionally substituted by $C_1$-$C_6$ alkyl; and the remaining substituents are as defined above.

In another embodiment the invention relates to compounds in accordance to the foregoing formulae (I), (I'), (I"), (II), (III), (IV) and/or (V), or a pharmaceutically acceptable salt thereof, wherein
R1 is $C_1$-$C_2$ alkyl;
R2 and R3 are independently from each other methyl;
R stands for piperidine or piperazine which may be optionally substituted 1 to 2 times by $C_1$-$C_6$ alkyl optionally substituted one or more times by hydroxy, oxo (=O), amino optionally substituted by $C_1$-$C_6$ alkoxycarbonyl, or mono $C_1$-$C_6$ alkyl-amino optionally substituted by $C_1$-$C_6$ alkoxycarbonyl; and
R4 is H.

In another embodiment the invention relates to compounds in accordance to the foregoing formulae (I), (I'), (I"), (II), (III), (IV) and/or (V), or a pharmaceutically acceptable salt thereof, wherein
R1 is ethyl;
R2 and R3 are independently from each other methyl;
R stands for piperidine or piperazine which may be optionally substituted 1 to 2 times by $C_1$-$C_6$ alkyl optionally substituted one or more times by hydroxy, oxo (=O), or mono $C_1$-$C_6$ alkyl-amino; and
R4 is H.

In another embodiment the invention relates to compounds in accordance to the foregoing formulae (I), (I'), (I"), (II), (III), (IV) and/or (V), or a pharmaceutically acceptable salt thereof, wherein
R1 is ethyl;
R2 and R3 are independently from each other methyl;
R stands for 4-piperidinyl or 1-piperazinyl which may be optionally substituted 1 to 2 times by $C_1$-$C_6$ alkyl optionally substituted one or more times by hydroxy, oxo (=O), or mono $C_1$-$C_6$ alkyl-amino; and
R4 is H.

In another embodiment the invention relates to compounds in accordance to the foregoing formulae (I), (I'), (I"), (II), (III), (IV) and/or (V), or a pharmaceutically acceptable salt thereof, wherein
R1 is ethyl;
R2 and R3 are independently from each other methyl;
R stands for 4-piperidinyl or 1-piperazinyl which may be optionally substituted once by $C_1$-$C_6$ alkyl optionally substituted 1-3 times by hydroxy, oxo (=O), or mono $C_1$-$C_6$ alkyl-amino; and
R4 is H.

In another embodiment the invention relates to compounds in accordance to the foregoing formulae (I), (I'), (I"), (II), (III), (IV) and/or (V), or a pharmaceutically acceptable salt thereof, wherein
R1 is ethyl;
R2 and R3 are independently from each other methyl;
R stands for 4-piperidinyl or 1-piperazinyl which may be optionally substituted once by $C_1$-$C_6$ alkyl optionally substituted 1-3 times by hydroxy, oxo (=O), or mono $C_1$-$C_6$ alkyl-amino, with the proviso that $C_1$-$C_6$ alkyl cannot be unsubstituted when $C_1$-$C_6$ alkyl is attached to a N-atom; and
R4 is H.

In another embodiment the invention relates to a compound of the invention, e.g. to a compound in accordance to the foregoing formulae (I), (I'), (I"), (II), (III), (IV) and/or (V), or a pharmaceutically acceptable salt thereof, wherein R stands for azetidine, piperidine, or piperazine, each of which may be optionally substituted 1 to 4 times by oxo (═O); hydroxy; $C_1$-$C_6$ alkyl optionally substituted one or more times by hydroxy, oxo (═O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; with the proviso that when azetidine, piperidine, or piperazine are substituted at the N-atom, said substituent shall not be unsubstituted $C_1$-$C_6$ alkyl.

In another embodiment the invention relates to a compound in accordance to the foregoing formulae (I), (I'), (I''), (II), (III), (IV) and/or (V), or a pharmaceutically acceptable salt thereof, wherein R1 is $C_1$-$C_2$ alkyl, in particular ethyl;
R2 and R3 are independently from each other methyl;
R4 is H; and
R is selected from the group of

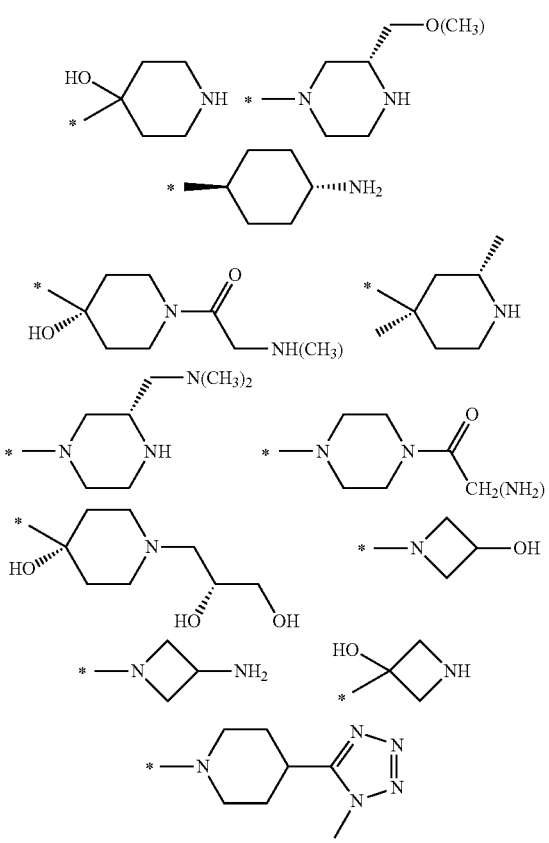

wherein a * denotes the place of attachment.

In another embodiment the invention relates to a compound in accordance to the foregoing formulae (II), (III), (IV) or (V), or a pharmaceutically acceptable salt thereof, wherein R1 is ethyl;
R2 and R3 are independently from each other methyl;
R4 is hydrogen; and
R is selected from the group of

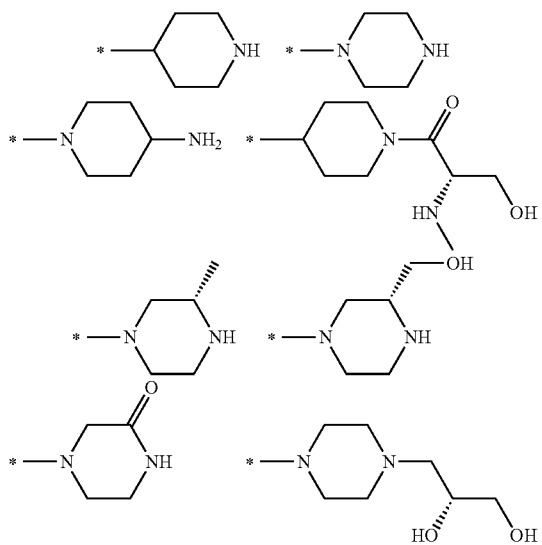

wherein a * denotes the place of attachment.

In another embodiment the invention relates to a compound in accordance to the foregoing formulae (II), (III), (IV) or (V), or a pharmaceutically acceptable salt thereof, wherein R1 is ethyl;
R2 and R3 are independently from each other methyl;
R4 is hydrogen; and
R is selected from the group of

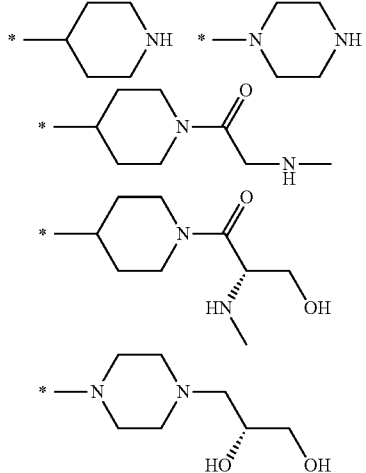

wherein a * denotes the place of attachment.

In another embodiment the invention relates to a compound in accordance to the foregoing formulae (II), or (III), or a pharmaceutically acceptable salt thereof, wherein R1 is ethyl;
R2 and R3 are independently from each other methyl;
R4 is hydrogen; and
R is selected from the group of

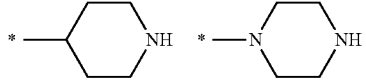

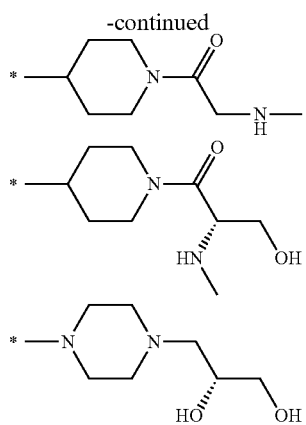

wherein a * denotes the place of attachment.

In another embodiment the invention relates to a compound of the present invention, in particular in accordance to the foregoing formulae (I), (I'), (I''), (II), (III), (IV) and/or (V), or a pharmaceutically acceptable salt thereof, wherein the compound is selected from:

4-{(E)-2-[4-(2-Ethyl-5,7-dimethyl-pyrazolo[1,5-a]pyrimidin-3-ylmethyl)-phenyl]-vinyl}-piperidin-4-ol,
4-{(E)-2-[4-(2-Ethyl-5,7-dimethyl-pyrazolo[1,5-a]pyrimidin-3-ylmethyl)-phenyl]-vinyl}-4-hydroxy-piperidine-1-carboxylic acid tert-butyl ester,
3-{(E)-3-[4-(2-Ethyl-5,7-dimethyl-pyrazolo[1,5-a]pyrimidin-3-ylmethyl)-phenyl]-allyl}-azetidin-3-ol,
3-{(E)-3-[4-(2-Ethyl-5,7-dimethyl-pyrazolo[1,5-a]pyrimidin-3-ylmethyl)-phenyl]-allyl}-3-hydroxy-azetidine-1-carboxylic acid tert-butyl ester,
4-{(E)-3-[4-(2-Ethyl-5,7-dimethyl-pyrazolo[1,5-a]pyrimidin-3-ylmethyl)-phenyl]-allyl}-piperidin-4-ol,
4-{(E)-3-[4-(2-Ethyl-5,7-dimethyl-pyrazolo[1,5-a]pyrimidin-3-ylmethyl)-phenyl]-allyl}-4-hydroxy-piperidine-1-carboxylic acid tert-butyl ester,
4-{3-[4-(2-Ethyl-5,7-dimethyl-pyrazolo[1,5-a]pyrimidin-3-ylmethyl)-phenyl]-propyl}-piperidin-4-ol,
4-{3-[4-(2-Ethyl-5,7-dimethyl-pyrazolo[1,5-a]pyrimidin-3-ylmethyl)-phenyl]-propyl}-4-hydroxy-piperidine-1-carboxylic acid tert-butyl ester,
(2S,4S)-4-{(E)-3-[4-(2-Ethyl-5,7-dimethyl-pyrazolo[1,5-a]pyrimidin-3-ylmethyl)-phenyl]-allyl}-2-methyl-piperidin-4-ol,
1-{(E)-3-[4-(2-Ethyl-5,7-dimethyl-pyrazolo[1,5-a]pyrimidin-3-ylmethyl)-phenyl]-allyl}-piperazin-2-one,
(R)-3-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-propane-1,2-diol,
1-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-methylamino-ethanone,
[2-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-oxo-ethyl]-methyl-carbamic acid tert-butyl ester,
((S)-4-{(E)-3-[4-(2-Ethyl-5,7-dimethyl-pyrazolo[1,5-a]pyrimidin-3-ylmethyl)-phenyl]-allyl}-piperazin-2-yl)-methanol,
(S)-4-{(E)-3-[4-(2-Ethyl-5,7-dimethyl-pyrazolo[1,5-a]pyrimidin-3-ylmethyl)-phenyl]-allyl}-2-hydroxymethyl-piperazine-1-carboxylic acid tert-butyl ester,
2-Ethyl-5,7-dimethyl-3-{4-[(E)-3-((S)-3-methyl-piperazin-1-yl)-propenyl]-benzyl}-pyrazolo[1,5-a]pyrimidine,
2-Ethyl-3-{4-[(E)-3-((S)-3-methoxymethyl-piperazin-1-yl)-propenyl]-benzyl}-5,7-dimethyl -pyrazolo[1,5-a]pyrimidine,
2-Amino-1-(4-{(E)-3-[4-(2-ethyl-5,7-dimethyl-pyrazolo[1,5-a]pyrimidin-3-ylmethyl) -phenyl]-allyl}-piperazin-1-yl)-ethanone,
2-Ethyl-5,7-dimethyl-3-(4-{(E)-3-[4-(1-methyl-1H-tetrazol-5-yl)-piperidin-1-yl]-propenyl}-benzyl)-pyrazolo[1,5-a]pyrimidine,
((S)-4-{(E)-3-[4-(2-Ethyl-5,7-dimethyl-pyrazolo[1,5-a]pyrimidin-3-ylmethyl)-phenyl]-allyl}-piperazin-2-ylmethyl)-dimethyl-amine,
(R)-2-Dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester,
(S)-2-Dimethylaminomethyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester,
2-Ethyl-5,7-dimethyl-3-[4-((E)-3-piperazin-1-yl-propenyl)-benzyl]-pyrazolo[1,5-a]pyrimidine,
(S)-1-(4-{(E)-3-[4-(2-Ethyl-5,7-dimethyl-pyrazolo[1,5-a]pyrimidin-3-ylmethyl)-phenyl]-allyl}-piperazin-1-yl)-3-hydroxy-2-methylamino-propan-1-one,
(4-{(E)-3-[4-(2-Ethyl-5,7-dimethyl-pyrazolo[1,5-a]pyrimidin-3-ylmethyl)-phenyl]-allyl}-piperazin-1-yl)-((2S,3R)-3-hydroxy-pyrrolidin-2-yl)-methanone,
(R)-3-(4-{(E)-3-[4-(2-Ethyl-5,7-dimethyl-pyrazolo[1,5-a]pyrimidin-3-ylmethyl)-phenyl]-allyl}-piperazin-1-yl)-propane-1,2-diol,
(R)-1-(tert-Butyl-dimethyl-silanyloxy)-3-(4-{(E)-3-[4-(2-ethyl-5,7-dimethyl-pyrazolo[1,5-]pyrimidin-3-ylmethyl)-phenyl]-allyl}-piperazin-1-yl)-propan-2-ol,
(E)-3-[4-(2-Ethyl-5,7-dimethyl-pyrazolo[1,5-a]pyrimidin-3-ylmethyl)-phenyl]-1-piperazin-1-yl-propenone,
4-{(E)-3-[4-(2-Ethyl-5,7-dimethyl-pyrazolo[1,5-a]pyrimidin-3-ylmethyl)-phenyl]-acryloyl}-piperazine-1-carboxylic acid tert-butyl ester,
3-[4-(2-Ethyl-5,7-dimethyl-pyrazolo[1,5-a]pyrimidin-3-ylmethyl)-phenyl]-1-piperazin-1-yl -propan-1-one,
4-{3-[4-(2-Ethyl-5,7-dimethyl-pyrazolo[1,5-a]pyrimidin-3-ylmethyl)-phenyl]-propionyl}-piperazine-1-carboxylic acid tert-butyl ester,
4-(2-Ethyl-5,7-dimethyl-pyrazolo[1,5-a]pyrimidin-3-ylmethyl)-N-piperidin-4-ylmethyl-benzamide,
2-Ethyl-5,7-dimethyl-3-[4-(piperidin-4-ylmethoxy)-benzyl]-pyrazolo[1,5-a]pyrimidine,
4-[4-(2-Ethyl-5,7-dimethyl-pyrazolo[1,5-a]pyrimidin-3-ylmethyl)-phenoxymethyl]-piperidine-1-carboxylic acid tert-butyl ester,
{4-[4-(2-Ethyl-5,7-dimethyl-pyrazolo[1,5-a]pyrimidin-3-ylmethyl)-phenoxymethyl]-piperidin-1-yl}-((2S,3R)-3-hydroxy-pyrrolidin-2-yl)-methanone,
4-[4-(2-Ethyl-5,7-dimethyl-pyrazolo[1,5-a]pyrimidin-3-ylmethyl)-phenoxymethyl]-cyclohexylamine,
(2S,3R)-3-Hydroxy-pyrrolidine-2-carboxylic acid {4-[4-(2-ethyl-5,7-dimethyl-pyrazolo[1,5-a]pyrimidin-3-ylmethyl)-phenoxymethyl]-cyclohexyl}-amide,
4-{2-[4-(2-Ethyl-5,7-dimethyl-pyrazolo[1,5-a]pyrimidin-3-ylmethyl)-phenoxy]-ethyl}-piperidin-4-ol,
2-Ethyl-5,7-dimethyl-3-[4-(2-piperazin-1-yl-ethoxy)-benzyl]-pyrazolo[1,5-a]pyrimidine,
4-{2-[4-(2-Ethyl-5,7-dimethyl-pyrazolo[1,5-a]pyrimidin-3-ylmethyl)-phenoxy]-ethyl}-piperazine-1-carboxylic acid tert-butyl ester,
2-Ethyl-3-{4-[2-((R)-3-methoxymethyl-piperazin-1-yl)-ethoxy]-benzyl}-5,7-dimethyl -pyrazolo[1,5-a]pyrimidine, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ol, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ylamine,
1-{1-[4-(2-Ethyl-5,7-dimethyl-pyrazolo[1,5-a]pyrimidin-3-ylmethyl)-phenyl]-1H-pyrazol-4-ylmethyl}-piperidin-4-ylamine,
2-Ethyl-5,7-dimethyl-3-[4-(4-piperazin-1-ylmethyl-pyrazol-1-yl)-benzyl]-pyrazolo[1,5-a]pyrimidine,
((R)-4-{1-[4-(2-Ethyl-5,7-dimethyl-pyrazolo[1,5-a]pyrimidin-3-ylmethyl)-phenyl]-1H -pyrazol-4-ylmethyl}-piperazin-2-yl)-methanol,
2-Ethyl-5,7-dimethyl-3-[4-(4-piperazin-1-ylmethyl-[1,2,3]triazol-1-yl)-benzyl]-pyrazolo[1,5-a]pyrimidine,
4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol,
4-{1-[4-(2-Ethyl-5,7-dimethyl-pyrazolo[1,5-a]pyrimidin-3-ylmethyl)-phenyl]-1H-[1,2,3]triazol-4-ylmethyl}-4-hydroxy-piperidine-1-carboxylic acid tert-butyl ester,
2-Ethyl-5,7-dimethyl-3-[4-(5-piperidin-4-yl-[1,3,4]oxadiazol-2-yl)-benzyl]-pyrazolo[1,5-a]pyrimidine,
4-{N'-[4-(2-Ethyl-5,7-dimethyl-pyrazolo[1,5-a]pyrimidin-3-ylmethyl)-benzoyl]-hydrazinocarbonyl}-piperidine-1-carboxylic acid tert-butyl ester,
4-{5-[4-(2-Ethyl-5,7-dimethyl-pyrazolo[1,5-a]pyrimidin-3-ylmethyl)-phenyl]-[1,3,4]oxadiazol-2-yl}-cyclohexylamine,
4-{N'-[4-(2-Ethyl-5,7-dimethyl-pyrazolo[1,5-a]pyrimidin-3-ylmethyl)-benzoyl]-hydrazinocarbonyl}-cyclohexyl)-carbamic acid tert-butyl ester,
4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol,
1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-2-methylamino-ethanone, and
(S)-1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-3-hydroxy-2-methylamino-propan-1-one.

In another embodiment the invention relates to a compound of the present invention, in particular in accordance to the foregoing formulae (I), (I'), (I''), (II), (III), (IV) and/or (V), or a pharmaceutically acceptable salt thereof, wherein the compound is selected from:
4-{(E)-3-[4-(2-Ethyl-5,7-dimethyl-pyrazolo[1,5-a]pyrimidin-3-ylmethyl)-phenyl]-allyl}-2-methyl-piperidin-4-ol,
3-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-propane-1,2-diol,
(4-{(E)-3-[4-(2-Ethyl-5,7-dimethyl-pyrazolo[1,5-a]pyrimidin-3-ylmethyl)-phenyl]-allyl}-piperazin-2-yl)-methanol,
4-{(E)-3-[4-(2-Ethyl-5,7-dimethyl-pyrazolo[1,5-a]pyrimidin-3-ylmethyl)-phenyl]-allyl}-2-hydroxymethyl-piperazine-1-carboxylic acid tert-butyl ester,
2-Ethyl-5,7-dimethyl-3-{4-[(E)-3-(3-methyl-piperazin-1-yl)-propenyl]-benzyl}-pyrazolo[1,5-a]pyrimidine,
2-Ethyl-3-{4-[(E)-3-(3-methoxymethyl-piperazin-1-yl)-propenyl]-benzyl}-5,7-dimethyl -pyrazolo[1,5-a]pyrimidine,
(4-{(E)-3-[4-(2-Ethyl-5,7-dimethyl-pyrazolo[1,5-a]pyrimidin-3-ylmethyl)-phenyl]-allyl}-piperazin-2-ylmethyl)-dimethyl-amine,
2-Dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester,
2-Dimethylaminomethyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester,
1-(4-{(E)-3-[4-(2-Ethyl-5,7-dimethyl-pyrazolo[1,5-a]pyrimidin-3-ylmethyl)-phenyl]-allyl}-piperazin-1-yl)-3-hydroxy-2-methylamino-propan-1-one,
(4-{(E)-3-[4-(2-Ethyl-5,7-dimethyl-pyrazolo[1,5-a]pyrimidin-3-ylmethyl)-phenyl]-allyl}-piperazin-1-yl)-(3-hydroxy-pyrrolidin-2-yl)-methanone,
(3-(4-{(E)-3-[4-(2-Ethyl-5,7-dimethyl-pyrazolo[1,5-a]pyrimidin-3-ylmethyl)-phenyl]-allyl}-piperazin-1-yl)-propane-1,2-diol,
1-(tert-Butyl-dimethyl-silanyloxy)-3-(4-{(E)-3-[4-(2-ethyl-5,7-dimethyl-pyrazolo-[1,5-]-pyrimidin-3-ylmethyl)-phenyl]-allyl}-piperazin-1-yl)-propan-2-ol,
{4-[4-(2-Ethyl-5,7-dimethyl-pyrazolo[1,5-a]pyrimidin-3-ylmethyl)-phenoxymethyl]-piperidin-1-yl}-(3-hydroxy-pyrrolidin-2-yl)-methanone,
3-Hydroxy-pyrrolidine-2-carboxylic acid {4-[4-(2-ethyl-5,7-dimethyl-pyrazolo[1,5-a]pyrimidin-3-ylmethyl)-phenoxymethyl]-cyclohexyl}-amide,
2-Ethyl-3-{4-[2-(3-methoxymethyl-piperazin-1-yl)-ethoxy]-benzyl}-5,7-dimethyl -pyrazolo[1,5-a]pyrimidine,
(4-{1-[4-(2-Ethyl-5,7-dimethyl-pyrazolo[1,5-a]pyrimidin-3-ylmethyl)-phenyl]-1H-pyrazol-4-ylmethyl}-piperazin-2-yl)-methanol, and
1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-3-hydroxy-2-methylamino-propan-1-one.

As used herein, the term "halogen" (or halo) refers to fluorine, bromine, chlorine or iodine, in particular fluorine, chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents selected from halogen, hydroxy or alkoxy groups.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-16, 1-10, 1-7, more preferably 1-4 carbon atoms.

A substituted alkoxy is an alkoxy group containing one or more, such as one, two or three substituents selected from halogen, hydroxy or alkoxy groups.

Similarly, each alkyl part of other groups like "alkylaminocrabonyl", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl".

As used herein, the term "cycloalkyl" refers to saturated or unsaturated monocyclic, bicyclic, tricyclic or spirocyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms.

A substituted cycloalkyl is a cycloalkyl group substituted by one, or two, or three, or four, or more substituents independently selected from the group consisting of hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, hydroxypyrrolidinyl-carbonyl e.g. 3-hydroxypyrrolidin-2-yl-carbonyl, $C_1$-$C_4$-alkyl-1H-tetrazolyl e.g. 1-methyl-1H-tetrazol-5-yl, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from amino, $C_1$-$C_4$-alkylamino, di-$C_1$-$C_4$-alkylamino, $C_1$-$C_4$-alkylcarbonylamino, $C_1$-$C_4$-alkylcarbonyl, halogen, hydroxyl or $C_1$-$C_4$-alkoxy groups. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "alkyl".

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that is saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl excludes heteroaryl. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like A substituted heterocyclyl is a heterocyclyl group independently substituted by 1-4, such as one, or two, or three, or four substituents selected from hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, hydroxypyrrolidinyl-carbonyl e.g. 3-hydroxypyrrolidin-2-yl-carbonyl, $C_1$-$C_4$-alkyl-1H-tetrazolyl e.g. 1-methyl-1H-tetrazol-5-yl, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from amino, $C_1$-$C_4$-alkylamino, di-$C_1$-$C_4$-alkylamino, $C_1$-$C_4$-alkylcarbonylamino, $C_1$-$C_4$-alkylcarbonyl, halogen, hydroxyl or $C_1$-$C_4$-alkoxy groups.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents selected from hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each heteroaryl part of other groups like "heteroaryloxy", "heteroaryloxyalkyl", "heteroaryloxycarbonyl" shall have the same meaning as described in the above-mentioned definition of "heteroaryl".

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared by known co-crystal forming procedures. Such procedures include grinding, heating, co-subliming, co-melting, or contacting in solution with the co-crystal former under crystallization conditions and isolating co-crystals thereby formed. Suitable co-crystal formers include those described in WO 2004/078163. Hence the invention further provides co-crystals comprising a compound of the invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by GPR4, or (ii) associated with GPR4 activity, or (iii) characterized by activity (normal or abnormal) of GPR4; or (2) reducing or inhibiting the activity of GPR4; or (3) reducing or inhibiting the expression of GPR4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of GPR4; or at least partially reducing or inhibiting the expression of GPR4.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "compounds of the invention" refers to a compound in accordance to the definition of formulae (I), (I'), (I"), (II), (III), (IV) and/or (V).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high-pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Synthesis of the Compounds of the Invention

Compounds of the invention may be prepared by the reaction sequences outlined and described below. In an embodiment an intermediate 3 is formed by reacting an appropriately substituted phenyl propionitrile, being typically commercially available, for example with an appropriate ester R1COOC$_{1-6}$ alkyl to form intermediate (1), which is reacted with hydrazine, for example under heat to form the aminopyrazole intermediate (2), which is reacted with an appropriately substituted diketone to form intermediate (3).

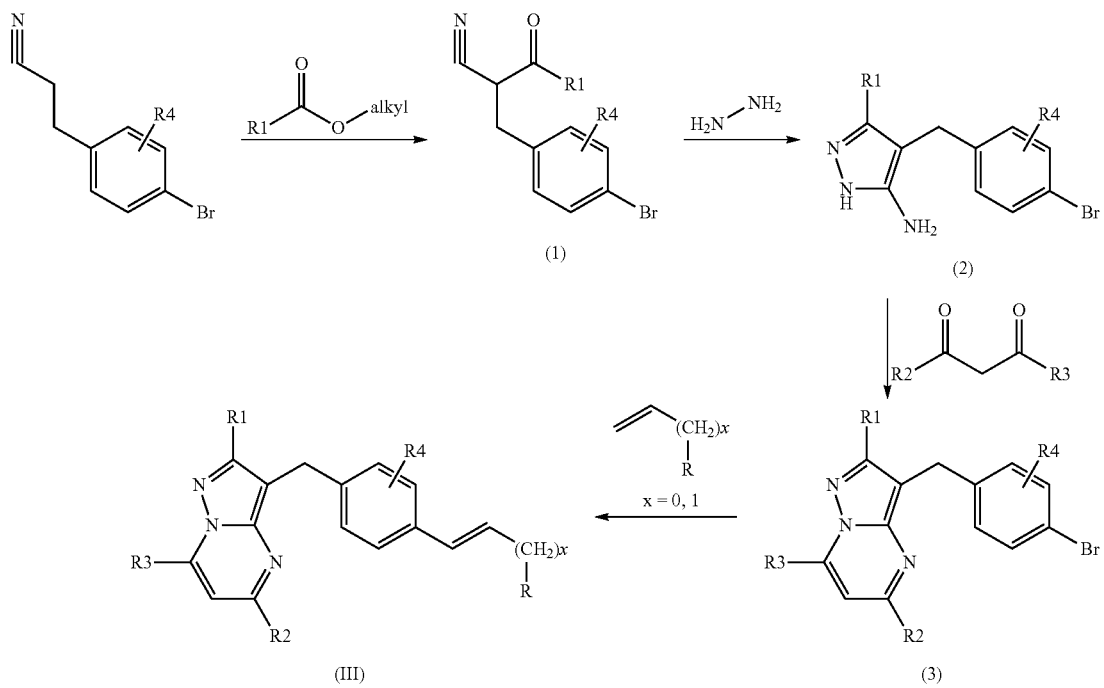

Intermediate (3) may conveniently be reacted with a number of substrates to form the compounds of the invention, such as for example compound carrying a central triazolo-, oxadiazolo-, imidazo methylene-, vinyl-, or allyl-linker (for x=1), which provides the compound of the invention in accordance to general formula (III).

A compound of general formula (III) may conveniently be reacted for example with hydrogen in the absence or presence of a catalyst to furnish a compound of general formula (V) as indicated below:

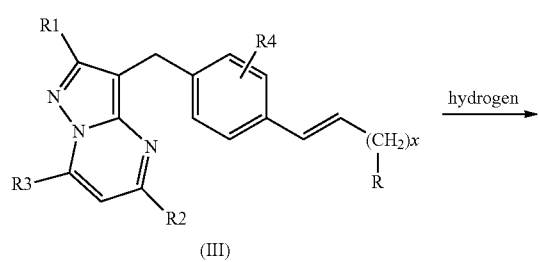

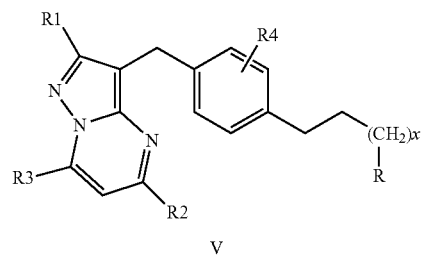

Intermediate (3) may also be reacted with other reactants to furnish the hydrazine intermediate (15) (see scheme below), which may be suitably reacted e.g. with an acrylate to form an imidazole intermediate (16), which is then reacted with an appropriate activated radical R to furnish a compound in accordance to general formula (IV).

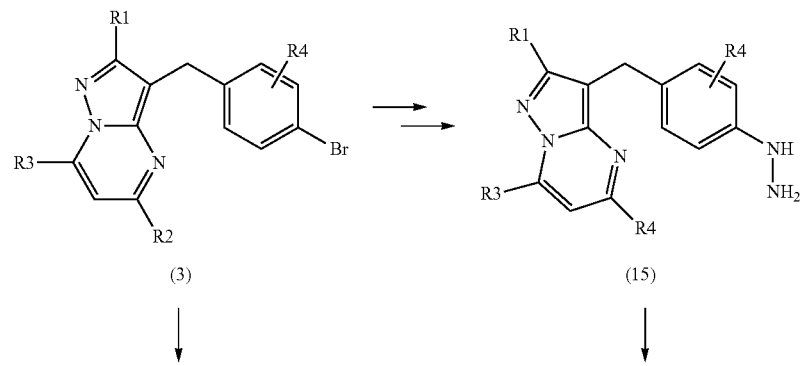

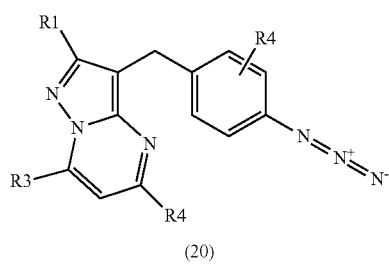

(20)

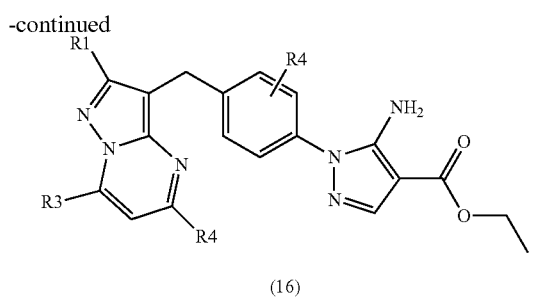

(16)

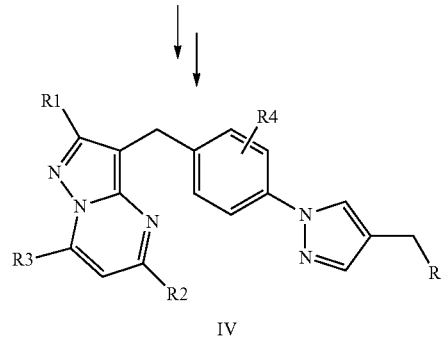

IV

An alternative route for synthesizing the pyrazolo pyrimidine moiety is shown in the following scheme below. The specific conversions are provided in reaction scheme 6, and shall explain the generic steps with specific exemplification. The activated nitrile (24) is obtained by condensation reaction of an optionally substituted cyanobenzaldehyde with cyanoketone (23). Upon hydrogenation of intermediate (24) the resulting ketonitrile (25) is reacted with an appropriated diketone to furnish the ring-closed intermediate (27), which may be conveniently converted to hydrazide derivative (29). Intermediates (27) and (29) may be further reacted to obtain various compounds of the invention, i.e. as shown in the experimental section.

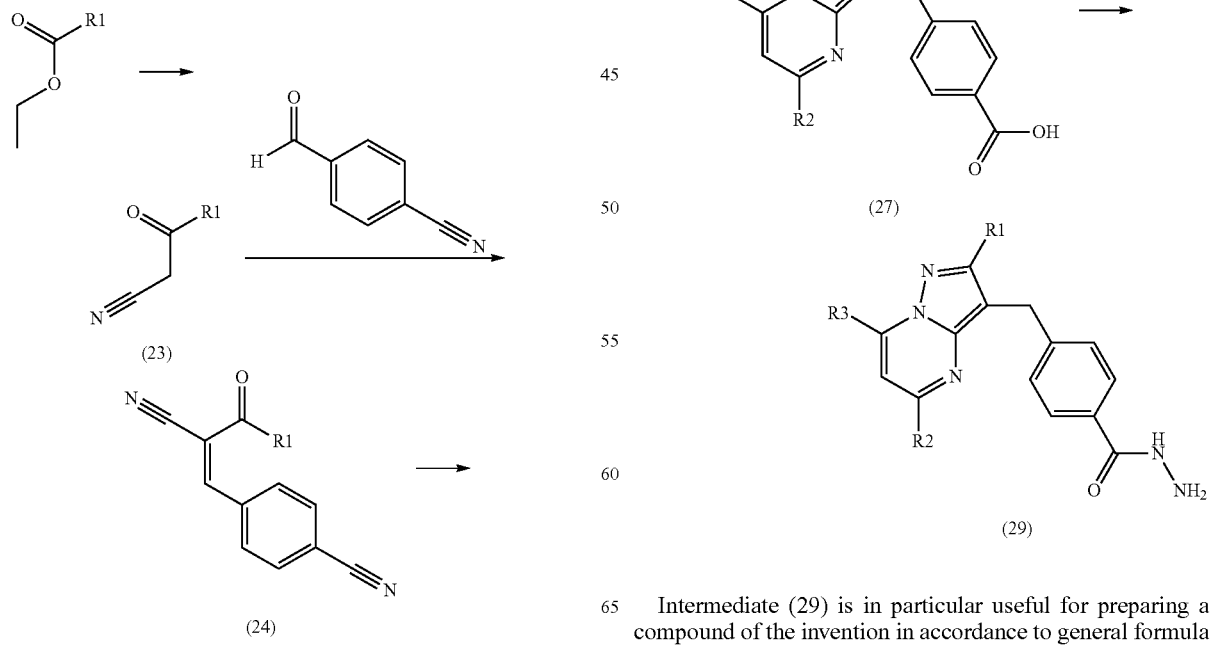

Intermediate (29) is in particular useful for preparing a compound of the invention in accordance to general formula II. For example, intermediate (29) is reacted with an appropriate carboxylic acid in accordance to the formula RCOOH, wherein R stands for the definitions given hereinabove, e.g. under coupling conditions, e.g. with HOBT/EDC, to furnish the coupled hydrazone, which is then reacted for example with tosylchloride and e.g. an organic base to render the ring closed compound, i.e. the oxadiazole compound of the invention in accordance to general formula II.

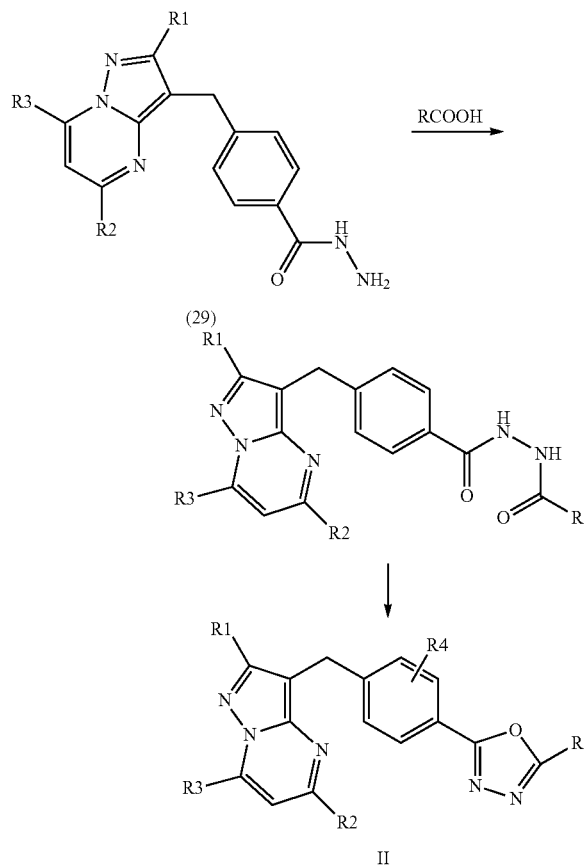

EXPERIMENTAL SECTION

Abbreviations
AcOH Acetic acid
Boc tert Butoxy carbonyl
Boc₂O Di-tert butyl dicarbonate
cHex cyclohexane
BINAP 2,2'-bis(diphenylphosphino)-1,1'-binaphthyl
DIAD Diisopropyl azodicarboxylate
DIBAH Di-isobutyl-aluminium-hydride
DIPEA Diisopropylethylamine
DMEM Dulbecco's Modified Eagle's Medium
DMF N,N-Dimethyl formamide
DMSO Dimethylsulfoxide
EDC 1-Ethyl-3-(3-dimethylaminopropyl)carbodiimide
EDTA Ethylendiamintetraacetat
EtOAc Acetic acid ethyl ester
Et₂O Diethylether
EtOH Ethanol
HBS HEPES buffered saline
HCl Hydrochloric acid
HEPES 2-(4-(2-Hydroxyethyl)-1-piperazinyl)-ethansulfonic acid
HOBT Hydroxybenzotriazol
HV High vacuum
HPLC High performance liquid chromatography
HTRF Homogenous time resolved fluorescence (assay)
IBMX 3-Isobutyl-1-methyl-xanthine
MeCN Acetonitril
MeOH Methanol
MTBE tert-Butylmethylether
rt room temperature
SPA Scintillation proximity assay
TFA Trifluoroacetic acid
THF Tetrahydrofurane
TLC Thin layer chromatography
TMSCl Trimethylsilylchloride
TsCl 4-Toluol-sulfochlorid 1H-NMR spectra were recorded on a Varian Gemini 500 MHz NMR spectrometer. Significant peaks were tabulated in the order: multiplicity (s, singlet; d, doublet; t, triplet; q, quartet; m, multiplet; br, broad) and number of protons. Electron Spray Ionization (ESI) mass spectra were recorded on a Hewlett Packard 5989A mass spectrometer.

Mass spectrometry results were reported as the ratio of mass over charge. Preparative HPLC purifications were performed with XTerra™ RP18 19×150 mm columns, using acetonitrile/water or MeOH/water as eluent systems. All reagents, starting materials and intermediates utilized in these examples were available from commercial sources or were readily prepared by methods known to those skilled in the art.

Synthesis of the Pyrazolopyrimidine Building Blocks

Reaction Scheme 1:

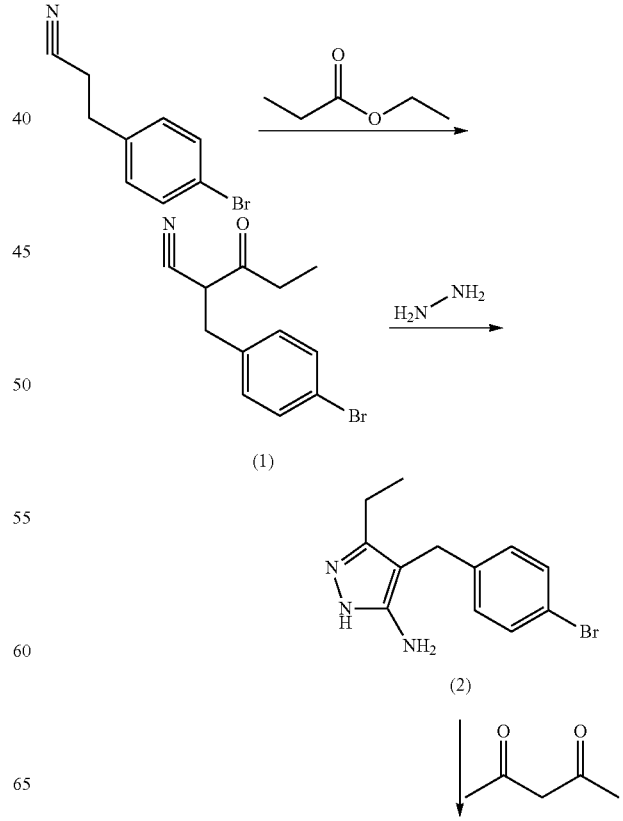

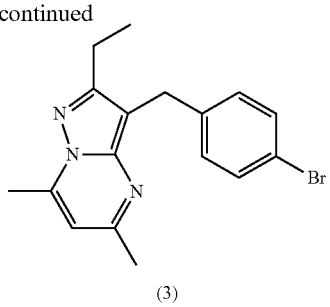

(3)

Synthesis of 3-(4-bromo-benzyl)-2-ethyl-5,7-dimethyl-pyrazolo[1,5-a]pyrimidine (3)

(1) Step A: 2-(4-bromo-benzyl)-3-oxo-pentanenitrile (1)

A 1.7 M solution of potassium tert. pentylate in toluene (81 ml, 139 mmol) was added dropwise to a solution of 3-(4-bromo-phenyl)-propionitrile (9.70 g, 46.2 mmol) in 200 ml of THF at rt, followed by addition of ethyl propionate (18.9 ml, 185 mmol). Stirring was continued for 20 min. The reaction mixture was quenched by careful addition of 1N hydrochloric acid and extracted with ethyl acetate. The organic layer was washed with water and brine, dried over $Na_2 SO_4$ and evaporated. The residue was purified by column chromatography (silica gel, EtOAc/n-hexane 3:7) to yield 1 as a yellow oil.

MS (ESI): 283 [M+NH4]$^+$, 264 [M−H]$^{-1}$H-NMR (DMSO-d6, 500 MHz, 121° C.) δ (ppm): 7.48 (d, 2H), 7.21 (d, 2H), 3.23 (br. s, 2H), 2.84 (br, 1H), 2.61 (br, 2H), 1.08 (t, 3H).

(2) Step B: 4-(4-bromo-benzyl)-5-ethyl-2H-pyrazol-3-ylamine (2)

A mixture of 2-(4-bromo-benzyl)-3-oxo-pentanenitrile (1, 10.4 g, 39.1 mmol) and hydrazine hydrate (1.9 ml, 39.1 mmol) in 35 ml of a 1:1 mixture of ethanol and acetic acid was heated in a microwave reactor to 140° C. for 15 min. After cooling the reaction mixture was diluted with ethyl acetate and washed several times with sat. sodium bicarbonate, followed by brine. The organic layer was dried over $Na_2 SO_4$ and evaporated to give a mixture of 2 and its N-acetamide. For conversion of the latter to 2, the crude product was taken up in 1N sodium hydroxide and heated to 160° C. in a microwave reactor until no N-acetamide could be detected by LC-MS (10-20 min). The reaction mixture was extracted with ethyl acetate, the organic layer was washed with brine, dried over $Na_2 SO_4$ and evaporated to yield 2 as a white powder, which was used in the next step without further purification.

MS (ESI): 280 [M+H]$^+$; $^1$H-NMR (DMSO-d6, 500 MHz) δ (ppm): 7.41 (d, 2H), 7.11 (d, 2H), 3.56 (s, 2H), 2.34 (q, 2H), 1.90 (s, 2H), 0.99 (t, 3H).

(3) Step C: 3-(4-bromo-benzyl)-2-ethyl-5,7-dimethyl-pyrazolo[1,5-a]pyrimidine (3)

To a solution of 4-(4-bromo-benzyl)-5-ethyl-2H-pyrazol-3-ylamine (2) (7.9 g, 28.2 mmol) in 120 ml of a 1:1 mixture of dioxane and trifluoroacetic acid 1:1 was added acetylacetone (2.9 ml, 28.2 mmol) at rt and the reaction mixture was stirred overnight.

The mixture was neutralized with sat. sodium bicarbonate, extracted with ethyl acetate, dried over $Na_2 SO_4$ and evaporated to dryness to yield 3 as an off-white solid which was used in the next step without further purification.

MS (ESI): 344 [M+H]$^+$; $^1$H-NMR (DMSO-d6, 600 MHz) δ (ppm): 7.41 (d, 2H), 7.12 (d, 2H), 6.75 (s, 1H), 3.99 (s, 2H), 2.67 (q, 2H), 2.64 (s, 3H), 2.50 (s, 3H), 1.12 (t, 3H).

Reaction Scheme 2:

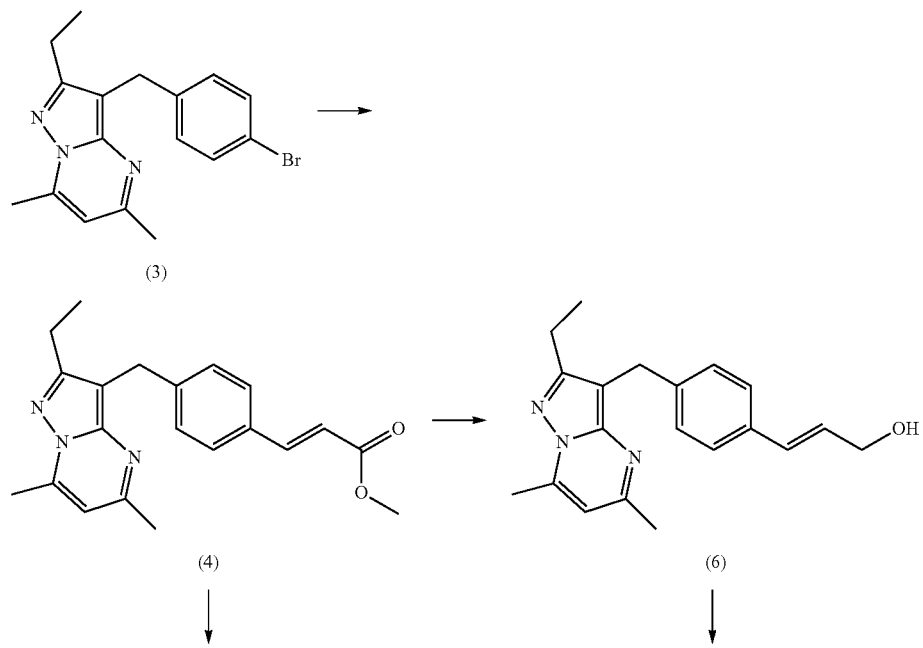

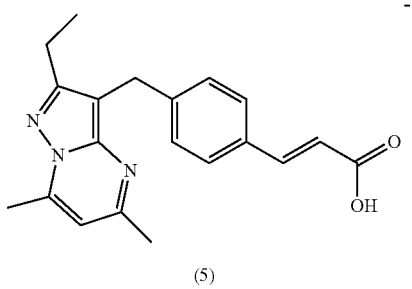

(5)

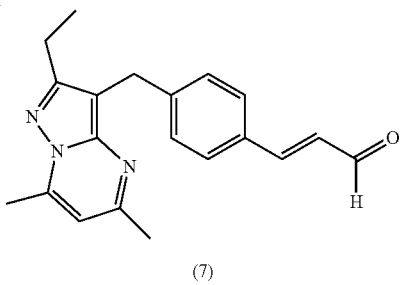

(7)

Synthesis of (E)-3-[4-(2-ethyl-5,7-dimethyl-pyrazolo[1,5-a]pyrimidin-3-ylmethyl)-phenyl]-propenal (7)

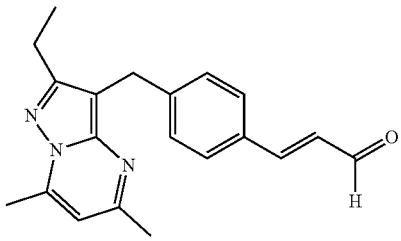 [SMILES: CCc1nn2c(C)cc(C)nc2c1Cc1ccc(/C=C/C=O)cc1]

(1) Step A: (E)-3-[4-(2-ethyl-5,7-dimethyl-pyrazolo[1,5-a]pyrimidin-3-ylmethyl)-phenyl]-acrylic acid methyl ester (4)

3-(4-Bromo-benzyl)-2-ethyl-5,7-dimethyl-pyrazolo[1,5-a]pyrimidine (3) (525 mg, 1.47 mmol) was dissolved in 15 ml of dioxane and after addition of methyl acrylate (264 ul, 2.93 mmol), dicyclohexyl-methylamine (622 ul ml, 2.93 mmol) and Pd(PtBu$_3$)$_2$ (15 mg, 0.03 mmol) the mixture was heated for 5 min at 130° C. in a microwave oven. Then the mixture was evaporated under reduced pressure. The residue was diluted with ethyl acetate, washed with sat. NaHCO$_3$— and NaCl-solution, and dried over Na$_2$ SO$_4$. Evaporation gave a yellow solid. The crude product was purified by recrystallization from diethylether to give a colorless solid.

MS (ESI): 350 [M+H]$^+$, $^1$H-NMR (DMSO-d6, 500 MHz) δ (ppm): 7.62 (s, 1H), 7.59 (d, 2H), 7.23 (d, 2H), 6.76 (s, 1H), 6.53 (d, 1H), 4.1 (s, 2H), 3.7 (s, 3H), 3.3 (s, 6H), 2.65 (q, 2H), 1.15 (t, 3H).

(2) Step B: (E)-3-[4-(2-ethyl-5,7-dimethyl-pyrazolo[1,5-a]pyrimidin-3-ylmethyl)-phenyl]-prop-2-en-1-ol (6)

(E)-3-[4-(2-Ethyl-5,7-dimethyl-pyrazolo[1,5-a]pyrimidin-3-ylmethyl)-phenyl]-acrylic acid methyl ester (4) (780 mg, 2.3 mmol), was dissolved in 23 ml dichloromethane and cooled to −78° C. A 1.2M solution of DIBAH in dichloromethane (5.8 ml, 7 mmol) was added dropwise.

The mixture was stirred for 3 h (TLC control) at −78° C. Then the mixture was quenched with water and evaporated. The residue was diluted with ethyl acetate, washed with water and NaCl-solution, dried over Na$_2$ SO$_4$ and evaporated. The crude product was purified by flash-chromatography (ethyl acetate/hexanes (1:1), silicagel) to yield a colorless oil.

MS (ESI): 322 [M+H]$^+$; $^1$H-NMR (DMSO-d6, 400 MHz) δ (ppm): 7.27 (d, 2H), 7.11 (d, 2H), 6.73 (s, 1H), 6.45 (d, 1H), 6.25 (dt, 1H), 4.8 (t, 1H), 4.08 (m, 2H), 4.0 (s, 2H), 2.65 (q, 2H), 2.6 (s, 3H), 2.45 (s, 3H), 1.1 (t, 3H).

(3) Step C: (E)-3-[4-(2-ethyl-5,7-dimethyl-pyrazolo[1,5-a]pyrimidin-3-ylmethyl)-phenyl]-propenal (7)

(E)-3-[4-(2-Ethyl-5,7-dimethyl-pyrazolo[1,5-a]pyrimidin-3-ylmethyl)-phenyl]-prop-2-en-1-ol (6) (650 mg, 2.02 mmol), was dissolved in 20 ml acetonitrile. MnO$_2$ (1.76 g, 20.2 mmol) was added and the black suspension was stirred at rt for 2.5 h. The reaction mixture was filtrated over celite and washed with acetonitrile. The filtrate was evaporated and purified by flash chromatography (silica gel, EtOAc/cHex (0-40%) to give a beige powder.

MS (ESI): 320 [M+H]$^+$; $^1$H-NMR (CDCl$_3$, 400 MHz) δ (ppm): 9.67 (d, 1H), 7.46 (d, 1H), 7.44 (d, 2H), 7.31 (d, 2H), 6.67 (dd, 1H), 6.49 (s, 1H), 4.20 (s, 2H), 2.74 (q, 2H), 2.72 (s, 3H), 2.57 (s, 3H), 1.21 (t, 3H).

Synthesis of (E)-3-[4-(2-ethyl-5,7-dimethyl-pyrazolo[1,5-a]pyrimidin-3-ylmethyl)-phenyl]-acrylic acid (5)

(E)-3-[4-(2-Ethyl-5,7-dimethyl-pyrazolo[1,5-a]pyrimidin-3-ylmethyl)-phenyl]-acrylic acid methyl ester (4) (2.94 g, 8.4 mmol) was dissolved in 25 ml of THF and 1M LiOH (25 ml) was added. The reaction mixture was stirred over night at rt. Then 0.5M HCl was added until a pH of 3.5 was reached. The mixture was extracted twice with EtOAc, the organic layer was washed with brine and dried over Na$_2$ SO$_4$. After evaporation the product was purified by recrystallisation from EtOAc to give a white solid.

MS (ESI): 336 [M+H]$^+$; $^1$H-NMR (DMSO-d6, 400 MHz) δ (ppm): 12.3 (s, 1H), 7.55 (d, 2H), 7.52 (d, 1H), 7.25 (d, 2H), 6.78 (s, 1H), 6.45 (d, 1H), 4.08 (s, 2H), 2.68 (q, 2H), 2.5 (s, 3H), 2.48 (s, 3H), 1.12 (t, 3H).

Reaction Scheme 3:

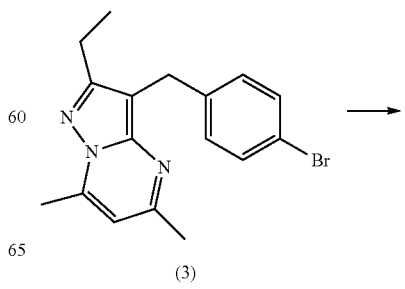

(3)

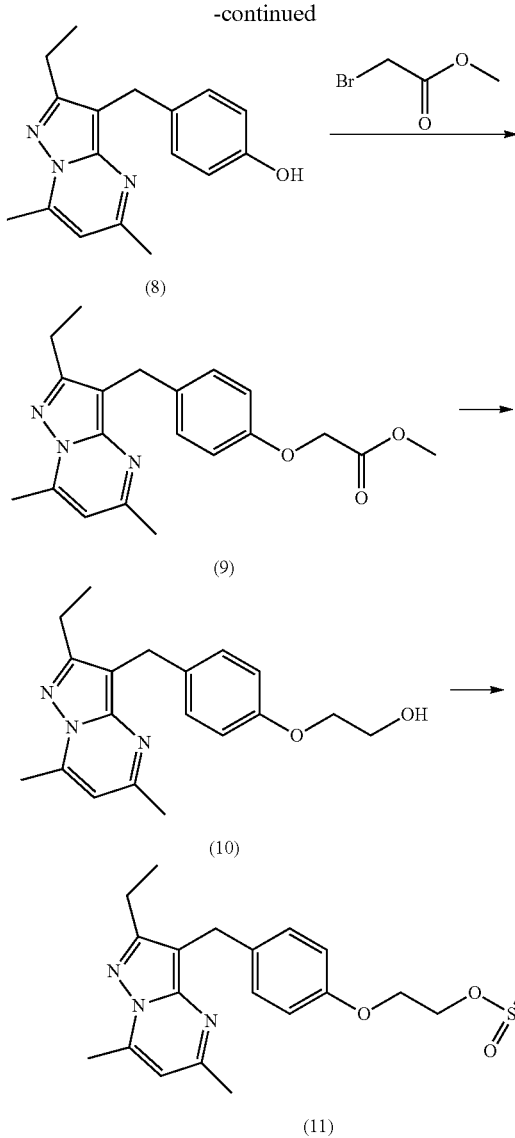

Synthesis of 4-(2-ethyl-5,7-dimethyl-pyrazolo[1,5-a]pyrimidin-3-ylmethyl)-phenol (8)

Potassiumhydroxide (1.96 g, 34.9 mmol) was dissolved in 30 ml of a 1:1 mixture of argon-flushed dioxane and water. After addition of 3-(4-bromo-benzyl)-2-ethyl-5,7-dimethyl-pyrazolo[1,5-a]pyrimidine (3) (4 g, 11.62 mmol), $Pd_2(dba)_3$ (426 mg, 0.465 mmol) and tetramethyl Xphos (894 mg, 1.859 mmol), the mixture was flushed with argon and stirred for 1 h at 100° C. Then the mixture was treated with 1N HCl and extracted with ethyl acetate. The combined organic layers were washed with brine, dried over $Na_2 SO_4$ and evaporated. Purification by chromatography (silica gel, ethylaceta/n-heptane) gave a yellow solid.

MS (ESI): 282 [M+H]$^+$; $^1$H-NMR (CDCl$_3$, 400 MHz) δ (ppm): 9.15 (s, 1H), 7.03 (d, 2H), 6.78 (s, 1H), 6.68 (d, 2H), 3.97 (s, 2H), 2.7 (q, 2H), 4.20 (s, 2H), 2.74 (q, 2H), 2.65 (s, 3H), 2.55 (s, 3H), 1.2 (t, 3H).

Synthesis of [4-(2-ethyl-5,7-dimethyl-pyrazolo[1,5-a]pyrimidin-3-ylmethyl)-phenoxy]-acetic acid methyl ester (9)

4-(2-Ethyl-5,7-dimethyl-pyrazolo[1,5-a]pyrimidin-3-ylmethyl)-phenol (8) (1 g, 3.55 mmol) was dissolved in 30 ml of THF and after addition of NaH (60% in mineral oil, 0.171 g, 4.27 mmol) the mixture was stirred for 20 min at rt. Then methyl 2-bromoacetate (0.382 ml, 3.91 mmol) was added and the mixture was stirred for 16 h at rt. The mixture was quenched with $H_2O$. The mixture was concentrated. The residue was diluted with ethyl acetate, washed with water and NaCl-solution, dried over $Na_2 SO_4$ and evaporated. The crude product was used in the next step without further purification.

MS (ESI): 354 [M+H]$^+$; $^1$H-NMR (CDCl$_3$, 400 MHz) δ (ppm): 7.09 (d, 2H), 6.8 (d, 2H), 6.75 (s, 1H), 4.7 (s, 2H), 3.97 (s, 2H), 3.68 (s, 3H), 2.68 (q, 2H), 2.62 (s, 3H), 2.50 (s, 3H), 1.15 (t, 3H).

Synthesis of 2-[4-(2-ethyl-5,7-dimethyl-pyrazolo[1,5-a]pyrimidin-3-ylmethyl)-phenoxy]-ethanol (10)

[4-(2-Ethyl-5,7-dimethyl-pyrazolo[1,5-a]pyrimidin-3-ylmethyl)-phenoxy]-acetic acid methyl ester (9) (1.2 g, 3.40 mmol) was dissolved in 36 ml of THF. LiAlH$_4$ (1.867 ml, 3.73 mmol) was added slowly to the reaction mixture and stirring was continued for 3 h at rt. The mixture was quenched with water and washed twice with $CH_2 Cl_2$. The aqueous layer was acidified with 1N HCl to pH3 and three times extracted with $CH_2 Cl_2$. The combined organic layers were washed with water and NaCl-solution, dried over $Na_2 SO_4$ and evaporated. The product was purified by chromatography (silica gel, chexane/ethylacetate).

MS (ESI): 326 [M+H]$^+$; $^1$H-NMR (CDCl$_3$, 400 MHz) δ (ppm): 7.16 (d, 2H), 6.79 (d, 2H), 6.45 (s, 1H), 4.1 (s, 2H), 4.03 (m, 2H), 3.92 (m, 2H), 2.75 (q, 2H), 2.70 (s, 3H), 2.55 (s, 3H), 2.43 (t, 1H), 1.22 (t, 3H).

Synthesis of methanesulfonic acid 2-[4-(2-ethyl-5,7-dimethyl-pyrazolo[1,5-a]pyrimidin-3-ylmethyl)-phenoxy]-ethyl ester (11)

A mixture of 2-[4-(2-Ethyl-5,7-dimethyl-pyrazolo[1,5-a]pyrimidin-3-ylmethyl)-phenoxy]-ethanol (10) (200 mg, 0.62 mmol), methanesulfonyl chloride (0.05 ml, 0.62 mmol) and Et$_3$N (0.09 ml, 0.62 mmol) was stirred at room temperature for 2 h. Then the reaction was quenched by addition of $CH_2Cl_2$ and water. The organic layer was then extracted with water and NaCl-solution, dried over $Na_2 SO_4$ and evaporated. The crude product was used in the next step without purification.

MS (ESI): 404 [M+H]$^+$; $^1$H-NMR (CDCl$_3$, 400 MHz) δ (ppm): 7.17 (d, 2H), 6.78 (d, 2H), 4.55 (m, 2H), 4.20 (m, 2H), 4.11 (s, 2H), 3.07 (s, 3 H), 2.73 (m, 2H), 2.17 (s, 3H), 1.20 (t, 3 H)

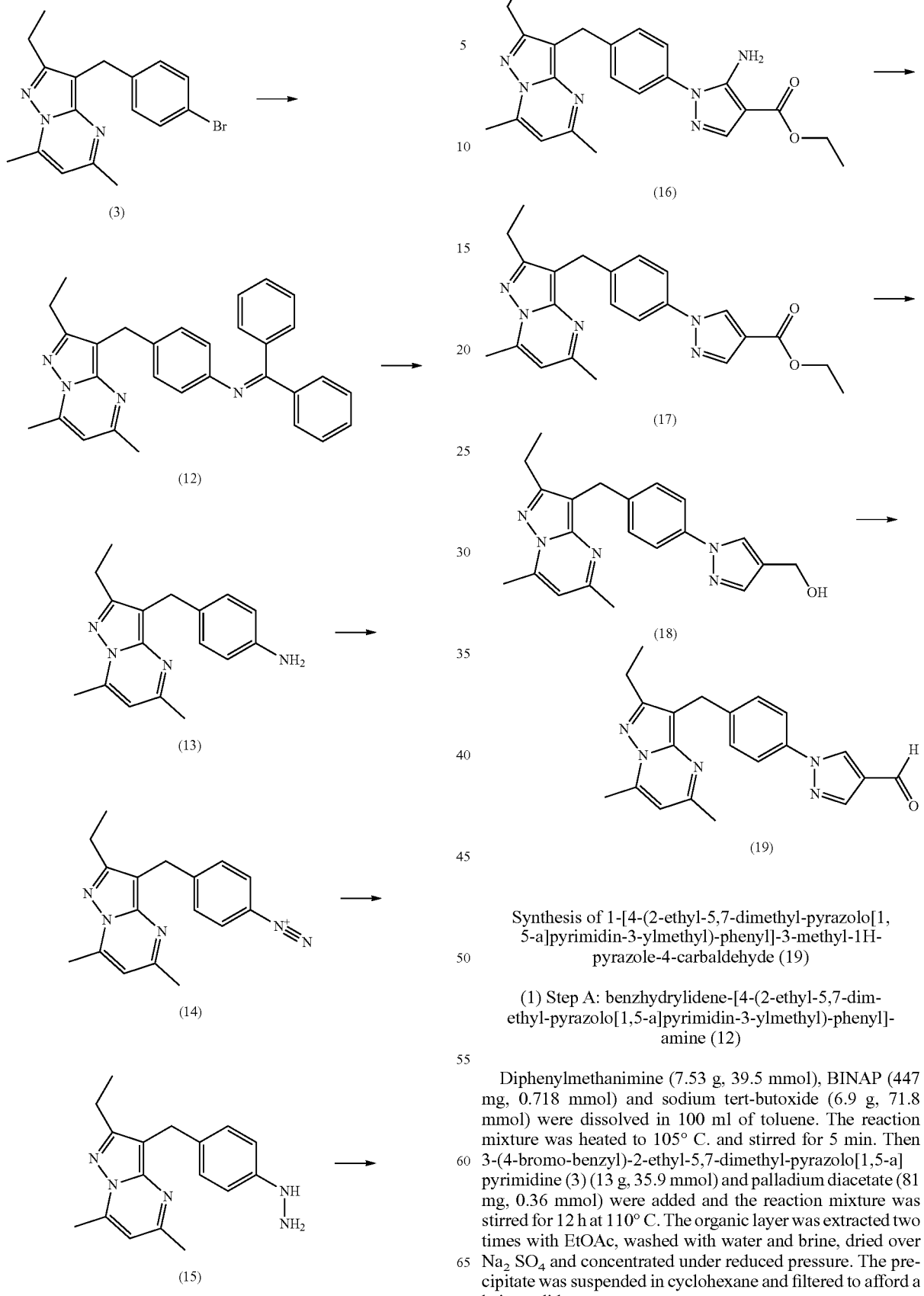

Synthesis of 1-[4-(2-ethyl-5,7-dimethyl-pyrazolo[1,5-a]pyrimidin-3-ylmethyl)-phenyl]-3-methyl-1H-pyrazole-4-carbaldehyde (19)

(1) Step A: benzhydrylidene-[4-(2-ethyl-5,7-dimethyl-pyrazolo[1,5-a]pyrimidin-3-ylmethyl)-phenyl]-amine (12)

Diphenylmethanimine (7.53 g, 39.5 mmol), BINAP (447 mg, 0.718 mmol) and sodium tert-butoxide (6.9 g, 71.8 mmol) were dissolved in 100 ml of toluene. The reaction mixture was heated to 105° C. and stirred for 5 min. Then 3-(4-bromo-benzyl)-2-ethyl-5,7-dimethyl-pyrazolo[1,5-a]pyrimidine (3) (13 g, 35.9 mmol) and palladium diacetate (81 mg, 0.36 mmol) were added and the reaction mixture was stirred for 12 h at 110° C. The organic layer was extracted two times with EtOAc, washed with water and brine, dried over Na₂SO₄ and concentrated under reduced pressure. The precipitate was suspended in cyclohexane and filtered to afford a beige solid.

MS (ESI): 445 [M+H]$^+$, $^1$H-NMR (CDCl$_3$, 400 MHz) δ (ppm): 7.75 (d, 2H), 7.4-7.5 (m, 3H), 7.27 (m, 2H), 7.12 (d, 2H), 7.00 (d, 2H), 6.65 (m, 2H), 6.46 (s, 1H), 4.06 (s, 2H), 2.71 (s, 3H), 2.58 (q, 2H), 2.56 (s, 3H), 1.09 (t, 3H).

(2) Step B: 4-(2-ethyl-5,7-dimethyl-pyrazolo[1,5-a]pyrimidin-3-ylmethyl)-phenylamine (13)

Benzhydrylidene-[4-(2-ethyl-5,7-dimethyl-pyrazolo[1,5-a]pyrimidin-3-ylmethyl)-phenyl]-amine (12) (3.97 g, 8.93 mmol) was dissolved in a mixture of water (40 ml), EtOH (10 ml) and conc. HCl (10 ml) and stirred at rt for 1 h. The reaction mixture was basified to pH 11 with Na$_2$CO$_3$. The organic layer was extracted with EtOAc, washed with water and brine, dried over Na$_2$SO$_4$ and concentrated to afford an orange oil. The crude product was purified by chromatography (2-50% EtOAc in cyclohexane) to afford a yellow solid.

MS (ESI): 281 [M+H]$^+$, $^1$H-NMR (CDCl$_3$, 400 MHz) δ (ppm): 6.82 (d, 2H), 6.73 (s, 1H), 6.43 (d, 2H), 4.78 (br s, 2H), 3.85 (s, 2H), 2.65 (q, 2H), 2.62 (s, 3H), 2.48 (s, 3H), 1.12 (t, 3H).

(3) Step C: 4-(2-ethyl-5,7-dimethyl-pyrazolo[1,5-a]pyrimidin-3-ylmethyl)-benzenediazonium salt (14)

Borontrifluoride etherate (2.4 ml, 19.1 mmol) was dissolved in 30 ml of THF and cooled to −50° C. 4-(2-Ethyl-5,7-dimethyl-pyrazolo[1,5-a]pyrimidin-3-ylmethyl)-phenylamine (13) (1.79 g, 6.38 mmol) was slowly added and the reaction mixture was stirred for 10 min at −50° C. Then isopentylnitrite (1.5 g, 128 mmol) was added and the reaction mixture was stirred over night.

The reaction mixture was concentrated and used in the next step without further purification.

(4) Step D: [4-(2-ethyl-5,7-dimethyl-pyrazolo[1,5-a]pyrimidin-3-ylmethyl)-phenyl]-hydrazine (15)

The crude 4-(2-ethyl-5,7-dimethyl-pyrazolo[1,5-a]pyrimidin-3-ylmethyl)-benzenediazonium salt (14) (1.8 g, 6.16 mmol) was dissolved in 40 ml of conc. HCl. After addition of tin(II)chloride (1.75 g, 9.24 mmol) the reaction mixture was stirred for 30 min at r.t. The reaction mixture was concentrated and used in the next step without further purification.

MS (ESI): 296 [M+H]$^+$.

(5) Step E: 5-amino-1-[4-(2-ethyl-5,7-dimethyl-pyrazolo[1,5-a]pyrimidin-3-ylmethyl)-phenyl]-3-methyl-1H-pyrazole-4-carboxylic acid ethyl ester (16)

[4-(2-Ethyl-5,7-dimethyl-pyrazolo[1,5-a]pyrimidin-3-ylmethyl)-phenyl]-hydrazine (15) (1.8 g, 6.1 mmol) was dissolved in 40 ml water/AcOH (1:3), and after addition of (E)-ethyl 2-cyano-3-ethoxyacrylate (1.24 g, 7.3 mmol) and sodium acetate (1.1 g, 13.4 mmol) the reaction mixture was stirred for 3 h at 100° C. Sodium carbonate was added (pH 11). The organic layer was extracted 2 times with EtOAc, washed with water and brine, dried over Na$_2$SO$_4$ and concentrated. The crude product was purified by chromatography (50-90% EtOAc in cyclohexane).

MS (ESI): 419 [M+H]$^+$, $^1$H-NMR (CDCl$_3$, 400 MHz) δ (ppm): 7.77 (s, 1H), 7.39 (m, 4H), 6.50 (s, 1H), 7.36 (d, 2H), 6.50 (s, 1H), 5.75 (br, 2H), 4.34 (q, 2H), 4.21 (s, 2H), 2.76 (q, 2H), 2.73 (s, 3H), 2.57 (s, 3H), 1.37 (t, 3H), 1.24 (t, 3H).

(6) Step F: 1-[4-(2-ethyl-5,7-dimethyl-pyrazolo[1,5-a]pyrimidin-3-ylmethyl)-phenyl]-3-methyl-1H-pyrazole-4-carboxylic acid ethyl ester (17)

5-Amino-1-[4-(2-ethyl-5,7-dimethyl-pyrazolo[1,5-a]pyrimidin-3-ylmethyl)-phenyl]-3-methyl-H-pyrazole-4-carboxylic acid ethyl ester (16) (923 mg, 1.76 mmol) was dissolved in 15 ml of THF and after addition of isoamylnitrite (620 mg, 5.29 mmol) the reaction mixture was stirred for 12 h at 70° C. The reaction mixture was evaporated under reduced pressure and purified by chromatography (10-50% EtOAc in cyclohexane, 30 min) to afford a yellow solid.

MS (ESI): 404 [M+H]$^+$, $^1$H-NMR (CDCl$_3$, 400 MHz) δ (ppm): 8.36 (s, 1H), 8.08 (s, 1H), 7.58 (d, 2H), 7.36 (d, 2H), 6.50 (s, 1H), 4.35 (q, 2H), 4.21 (s, 2H), 2.76 (q, 2H), 2.74 (s, 3H), 2.58 (s, 3H), 1.39 (t, 3H), 1.23 (t, 3H).

(7) Step G: {1-[4-(2-ethyl-5,7-dimethyl-pyrazolo[1,5-a]pyrimidin-3-ylmethyl)-phenyl]-3-methyl-1H-pyrazol-4-yl}-methanol (18)

1-[4-(2-Ethyl-5,7-dimethyl-pyrazolo[1,5-a]pyrimidin-3-ylmethyl)-phenyl]-3-methyl-1H-pyrazole-4-carboxylic acid ethyl ester (17) (618 mg, 1.53 mmol) was dissolved in 10 ml of dichloromethane and cooled at −70° C. A 1M solution of DIBAH in THF (3.1 ml, 3.1 mmol) was added and the reaction mixture was stirred for 2 h at −70° C. The mixture was quenched with water and diluted with dichloromethane. The mixture was filtrated and extracted with dichloromethane. Organic layer was washed with water and brine, dried over Na$_2$SO$_4$ and concentrated to afford a yellow foam. The product was used in the next step without further purification.

MS (ESI): 362 [M+H]$^+$, $^1$H-NMR (CDCl$_3$, 400 MHz) δ (ppm): 7.8 (s, 1H), 7.6 (s, 1H), 7.44 (d, 2H), 7.23 (d, 2H), 6.37 (s, 1H), 4.57 (s, 2H), 4.09 (s, 2H), 2.77 (q, 2H), 2.7 (s, 3H), 2.50 (s, 3H), 1.13 (t, 3H).

(8) Step H: 1-[4-(2-ethyl-5,7-dimethyl-pyrazolo[1,5-a]pyrimidin-3-ylmethyl)-phenyl]-3-methyl-1H-pyrazole-4-carbaldehyde (19)

{1-[4-(2-Ethyl-5,7-dimethyl-pyrazolo[1,5-a]pyrimidin-3-ylmethyl)-phenyl]-3-methyl-1H-pyrazol-4-yl}-methanol (18) (500 mg, 1.38 mmol) was dissolved in 10 ml of dichloromethane and after addition of manganese dioxide (1.2 g, 13.8 mmol) the reaction mixture was stirred for 3 h at rt. The mixture was filtrated though celite and evaporated under reduced pressure. The product was used in the next step without further purification.

MS (ESI): 360 [M+H]$^+$, $^1$H-NMR (CDCl$_3$, 400 MHz) δ (ppm): 9.97 (s, 1H), 8.39 (s, 1H), 8.15 (s, 1H), 7.58 (d, 2H), 7.38 (d, 2H), 6.51 (s, 1H), 4.22 (s, 2H), 2.77 (q, 2H), 2.74 (s, 3H), 2.58 (s, 3H), 1.24 (t, 3H).

Reaction Scheme 5:

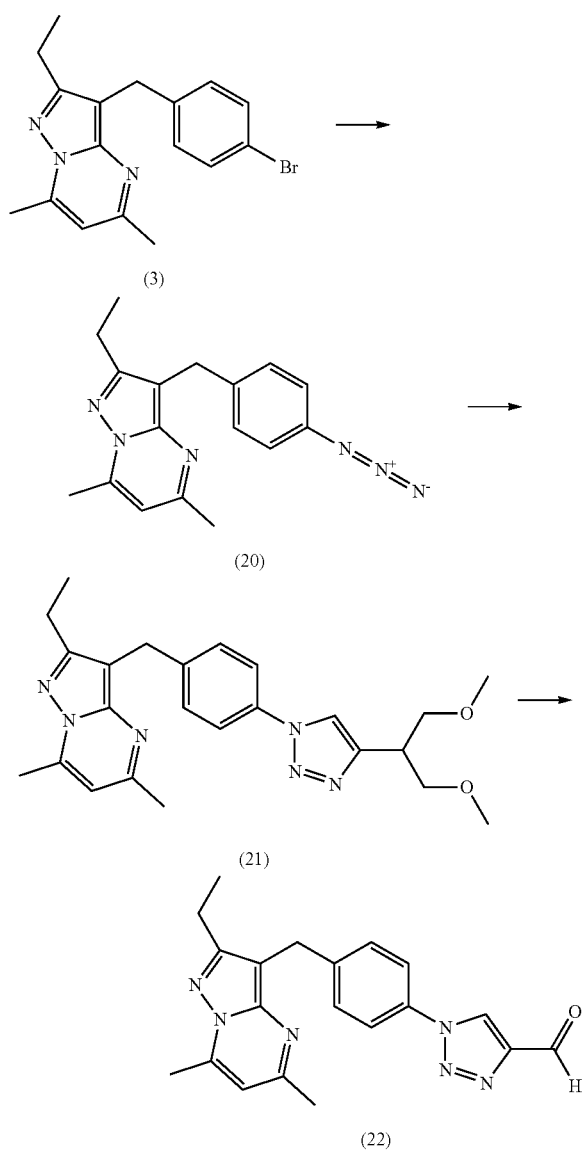

Synthesis of 1-[4-(2-ethyl-5,7-dimethyl-pyrazolo[1,5-a]pyrimidin-3-ylmethyl)-phenyl]-1H-[1,2,3]triazole-4-carbaldehyde (22)

(1) Step A: 3-(4-azido-benzyl)-2-ethyl-5,7-dimethyl-pyrazolo[1,5-a]pyrimidine (20)

A vial containing 3-(4-bromo-benzyl)-2-ethyl-5,7-dimethyl-pyrazolo[1,5-a]pyrimidine (3) (10 g, 29.0 mmol), sodium azide (3.78 g, 58.1 mmol), copper(I) iodide (0.553 g, 2.90 mmol), N,N'-dimethylethylenediamine (0.469 ml, 4.36 mmol) and sodium ascorbate (0.288 g, 1.452 mmol) in ethanol (45 ml)/water (15.00 ml) was submitted to microwave irradiations for 1 h at 100° C. The reaction was diluted with EtOAc and washed with sat aqu $Na_2 CO_3$, water and brine. The organic layer was dried over anhydrous $Na_2 SO_4$, filtered and concentrated under HV. The crude product was purified by flash chromatography (silica gel, EtOAc/heptane 5% to 40%) to give a pale yellow solid.

MS (ESI): 306 [M]$^+$, $^1$H-NMR (MeOD, 360 MHz) δ (ppm): 7.23 (d, 2H), 6.96 (d, 2H), 6.75 (s, 1H), 4.15 (s, 2H), 2.75 (q, 2H), 2.73 (s, 3H), 2.58 (s, 3H), 1.19 (t, 9H).

(2) Step B: 3-[4-(4-diethoxymethyl-[1,2,3]triazol-1-yl)-benzyl]-2-ethyl-5,7-dimethyl-pyrazolo[1,5-a]pyrimidine (21)

A solution of 3-(4-azido-benzyl)-2-ethyl-5,7-dimethyl-pyrazolo[1,5-a]pyrimidine (20) (2 g, 6.53 mmol), propionaldehyde diethylacetal (1.294 g, 9.79 mmol) and copper(I) iodide (1.492 g, 7.83 mmol) in 33 ml of acetonitrile was stirred at r.t. for 24 h. The reaction was diluted in EtOAc and washed with sat aq $Na_2 CO_3$, water and brine. The organic layer was dried over anhydrous $Na_2 SO_4$, filtered and concentrated under HV. The crude product was purified by flash chromatography (silica gel, EtOAc/DCM 0% to 50%) to give a pale yellow oil.

MS (ESI): 435 [M+H]$^+$, $^1$H-NMR (DMSO-d6, 360 MHz) δ (ppm): 8.69 (s, 1H), 7.81 (d, 2H), 7.39 (d, 2H), 6.79 (s, 1H), 5.74 (s, 1H), 4.14 (s, 2H), 3.61 (q, 4H), 2.72 (q, 2H), 2.66 (s, 3H), 2.51 (s, 3H), 1.17 (t, 9H).

(3) Step C: 1-[4-(2-ethyl-5,7-dimethyl-pyrazolo[1,5-a]pyrimidin-3-ylmethyl)-phenyl]-1H-[1,2,3]triazole-4-carbaldehyde (22)

A solution of 3-[4-(4-diethoxymethyl-[1,2,3]triazol-1-yl)-benzyl]-2-ethyl-5,7-dimethyl-pyrazolo[1,5-a]pyrimidine (21) (2.19 g, 5.04 mmol) and 4N HCl (50 ml, 200 mmol) in 30 ml of dioxane was stirred at r.t. for 2 h. The reaction mixture was quenched with sat aq $NaHCO_3$ and extracted with dichloromethane. The combined organic layers were washed with brine, dried over anhydrous $Na_2 SO_4$, filtered and concentrated under HV.

The product was obtained as a white solid.

MS (ESI): 361 [M+H]$^+$, $^1$H-NMR (DMSO-d6, 360 MHz) δ (ppm): 10.11 (s, 1H), 9.50 (s, 1H), 7.86 (d, 2H), 7.44 (d, 2H), 6.80 (s, 1H), 4.16 (s, 2H), 2.73 (q, 2H), 2.66 (s, 3H), 2.5 (s, 3H), 1.18 (t, 3H).

Reaction Scheme 6:

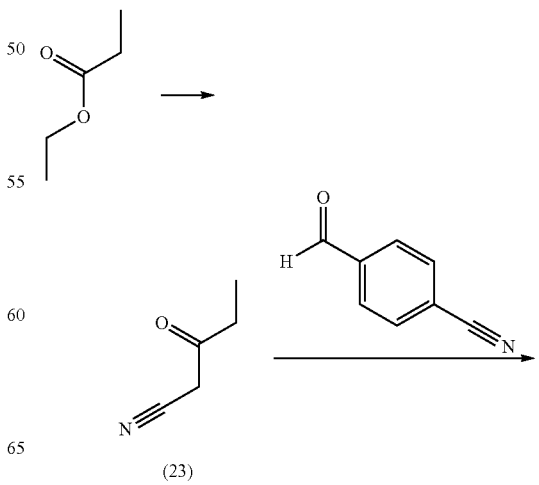

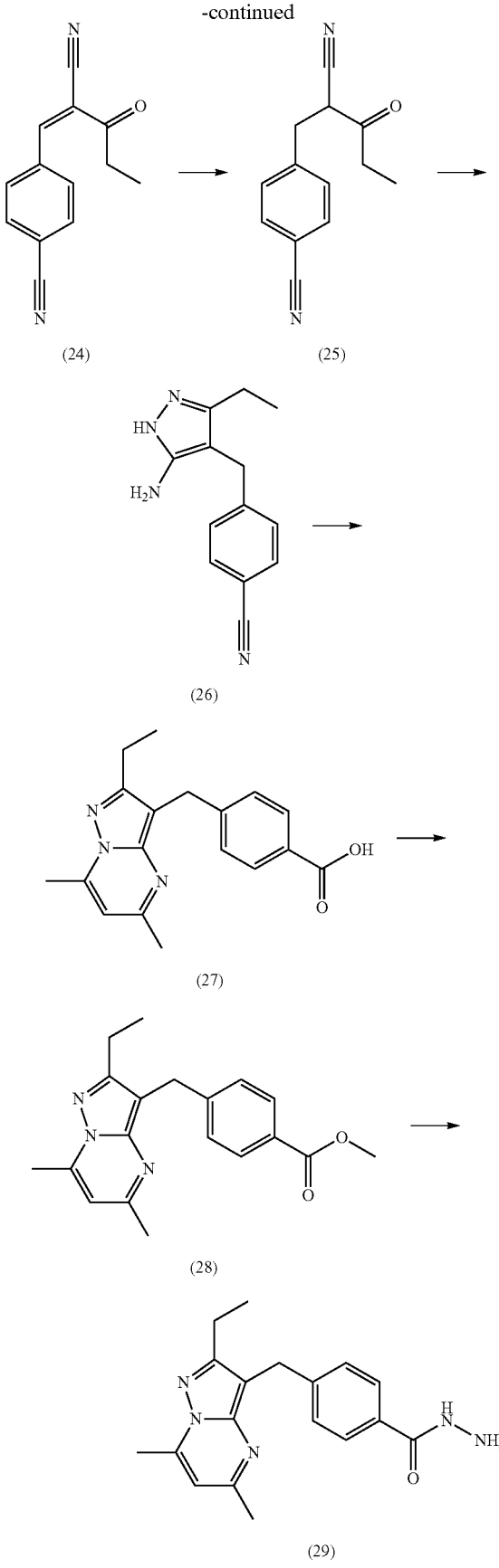

Synthesis of 4-(2-ethyl-5,7-dimethyl-pyrazolo[1,5-a]pyrimidin-3-ylmethyl)-benzoic acid hydrazide (29)

(1) Step A: 3-oxopentanenitrile (23)

To a 1000 ml, four-necked flask equipped with an overhead stirrer, a thermocouple and a condenser was charged with potassium t-butoxide (36.5 g, 323.1 mmol) and 200 ml of THF. A mixture of ethyl propionate (30 g, 293.7 mmol) and acetonitrile (14.4 g, 352.5 mmol) was added to the resulting solution over 45 min while maintaining the batch temperature at about 20° C. The batch was stirred for additional 1 hour at 20° C., and was cooled to 0° C. followed by addition of 1N HCl (400 ml) to pH ~7 while maintaining the batch temperature at about 0° C. The organics were extracted with ethyl acetate (300 ml) and washed with 15% NaCl (200 ml). The organic layer was dried over $MgSO_4$. It was filtered and concentrated in vacuo to give a product residue with some residual solvent.

This crude oil product 23 could be used directly in the next step without further purification.

$^1$H NMR (500 MHz, $CDCl_3$) δ (ppm): 3.42 (s, 2H), 2.60 (m, 2H), 1.05 (t, 3H).

(2) Step B: 4-(2-cyano-3-oxopent-1-enyl)benzonitrile (24)

To a 1000 ml, four-necked flask equipped with an overhead stirrer, a thermocouple and a condenser was charged with 3-oxopentanenitrile (23) (21.8 g, 135 mmol, 60%) of, 4-formylbenzonitrile (17.7 g, 135 mmol), L-proline (3.65 g, 27 mmol, 0.2 eq) and 200 ml of EtOH. The mixture was stirred at 22° C. for 16 hours and concentrated to a volume of approximately 120 ml. 100 ml of MTBE was added and the mixture was stirred at 22° C. for about 30 min. The precipitate was collected by vacuum filtration. The solid was washed with 50 ml of MTBE. It was dried in a vacuum oven at 50° C. to give the product 24 as a off white solid. $^1$H NMR (500 MHz, $CDCl_3$) δ (ppm): 8.20 (s, 1H), 8.10 (d, 2H), 7.81 (d, 2H), 3.00 (m, 2H), 1.28 (t, 3H).

(3) Step C: 4-(2-cyano-3-oxopentyl)benzonitrile (25)

To a hydrogenation reactor was charged with 4-(2-cyano-3-oxopent-1-enyl)benzonitrile (24) (20 g, 95.1 mmol), Pd/C (2 g, 10%, wet), MeOH (100 ml) and MeCN (100 ml). The mixture was stirred at 25° C. under 50 psi hydrogen for 2 h until absorption of hydrogen was stopped. The mixture was filtered through a celite pad to remove catalyst. It was concentrated under reduced pressure to give product 25 (20 g, 99%) as an oil. The product was directly used for the next step reaction without further purification.

$^1$H NMR (500 MHz, $CDCl_3$) δ (ppm): 7.70 (d, 2H), 7.41 (d, 2H), 3.69 (t, 1H), 3.25 (m, 2H), 2.71 (m, 2H), 1.13 (t, 3H).

(4) Step D: 4-((5-amino-3-ethyl-1H-pyrazol-4-yl)methyl)benzonitrile (26)

To a 500 ml, four-necked flask equipped with an overhead stirrer, a thermocouple and a condenser was charged 4-(2-cyano-3-oxopentyl)benzonitrile (25) (5 g, 23.6 mmol) and 50 ml of EtOH. The solution was stirred and hydrazine (1.65 g, 33 mmol, 64%, 1.4 eq) was added. The batch was stirred at 65° C. for 3 hours. The solvent was concentrated by vacuum and the residue was slurried with 50 ml of MTBE at room temperature for 30 min. The precipitate was collected by vacuum filtration and the solid was washed with MTBE to give product 26 as a white solid.

$^1$H NMR (500 MHz, CDCl$_3$) δ (ppm): 7.62 (d, 2H), 7.30 (d, 2H), 6.42-6.80 (s, br, 3H), 3.79 (s, 2H), 2.56 (m, 2H), 1.20 (t, 3H).

(5) Step E: 4-((2-ethyl-5,7-dimethylpyrazolo[1,5-a] pyrimidin-3-yl)methyl)benzoic acid (27)

To a 500 ml, four-necked flask equipped with an overhead stirrer, a thermocouple and a condenser was charged with 4-((5-amino-3-ethyl-1H-pyrazol-4-yl)methyl)benzonitrile (26) (12.8 g, 56.5 mmol), pentane-2,4-dione (6.8 g, 67.9 mmol, 1.2 eq), 20 ml of HOAc and 40 ml of concentrated HCl. The mixture was stirred at 110° C. for 43 hours. It was cooled to room temperature and 300 ml of water was added. Slowly, the solution became a suspension. It was stirred at room temperature for 1 h. The precipitate was collected by vacuum filtration and the solid was washed with water. The solid was vacuum oven dried at 50° C. for 5 h.

$^1$H NMR (500 MHz, DMSO-d6) δ (ppm): 12.61-12.89 (s, br, 1H), 7.83 (d, 2H), 7.30 (d, 2H), 6.81 (s, 1H), 4.11 (d, 2H), 2.67 (m, 2H), 2.63 (s, 3H), 2.48 (s, 3H), 1.12 (t, 3H).

(6) Step F: 4-(2-ethyl-5,7-dimethyl-pyrazolo[1,5-a] pyrimidin-3-ylmethyl)-enzoic acid methyl ester (28)

4-((2-ethyl-5,7-dimethylpyrazolo[1,5-a]pyrimidin-3-yl) methyl)benzoic acid (27) (1.6 g, 5.17 mmol) was dissolved in 10 ml of methanol, then TMSCl (1.983 ml, 15.52 mmol) was added and the reaction mixture was stirred for 16 h at rt. The reaction mixture was concentrated under reduced pressure to give a yellow solid. The compound will be used in the next step without further purification.

MS (ESI): 324 [M–H]$^+$, $^1$H NMR (400 MHz, DMSO-d6) δ (ppm): 7.85 (d, 2H), 7.33 (d, 2H), 6.77 (s, 1H), 3.82 (s, 3H), 2.68 (q, 2H), 1.12 (t, 3H).

(7) Step G: 4-(2-ethyl-5,7-dimethyl-pyrazolo[1,5-a] pyrimidin-3-ylmethyl)-benzoic acid hydrazide (29)

4-(2-Ethyl-5,7-dimethyl-pyrazolo[1,5-a]pyrimidin-3-yl-methyl)-enzoic acid methyl ester (28) (2.13 g, 6.59 mmol) was dissolved in 40 ml of methanol and after addition of hydrazin hydrate (9.1 ml, 198 mmol) the mixture was stirred at 80° C. for 3 hr. The reaction mixture was filtered to afford a white solid which was used in the next step without further purification.

MS (ESI): 324 [M–H]$^+$, $^1$H NMR (400 MHz, DMSO-d6) δ (ppm): 7.65 (d, 2H), 7.35 (d, 2H), 6.5 (s, 1H), 4.2 (s, 2H), 4.1 (br, 1H), 3.82 (s, 3H), 2.75 (q, 2H), 1.2 (t, 3H).

Synthesis of the piperidine, azetidine and piperazine building blocks

Reaction Scheme 7:

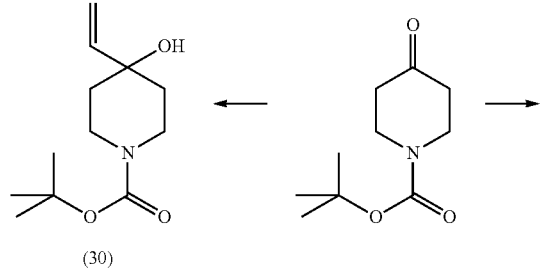

(30)

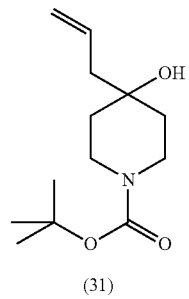

(31)

4-Vinyl-4-hydroxy-piperidine-1-carboxylic acid tert-butyl ester (30)

4-Oxo-piperidine-1-carboxylic acid tert-butyl ester (2.5 g, 12.5 mmol) was dissolved in 25 ml of diethylether and cooled to 0° C. A 1M solution of vinylmagnesiumbromide in THF (16.3 ml, 16.31 mmol) was added dropwise at 0° C. After 90 min stirring at 0° C., the reaction mixture was quenched with NH$_4$Cl solution and extracted with ethyl acetate. The organic layer was washed with brine, dried over Na$_2$SO$_4$ and evaporated. The crude product was further purified by flash chromatography (silicagel, cyclohexane/ethylacetate 4:1).

MS (ESI): 226 [M–H]$^+$, $^1$H-NMR (CDCl$_3$, 400 MHz) δ (ppm): 5.95 (dd, 1H), 5.30 (d, 1H), 5.12 (d, 1H), 3.84 (m, 2H), 3.25 (m, 2H), 1.7 (m, 2H), 1.55 (m, 3H), 1.48 (s, 9H).

4-Allyl-4-hydroxy-piperidine-1-carboxylic acid tert-butyl ester (31)

This compound was synthesized analogously to 30 using allyl magnesiumbromide.

MS (ESI): 240 [M–H]$^+$, $^1$H-NMR (CDCl$_3$, 400 MHz) δ (ppm): 5.87 (m, 1H), 5.22 (d, 1H), 5.15 (d, 1H), 3.82 (dt, 2H), 3.2 (m, 2H), 2.25 (d, 2H), 1.5-1.6 (m, 5H), 1.48 (s, 9H).

Reaction Scheme 8:

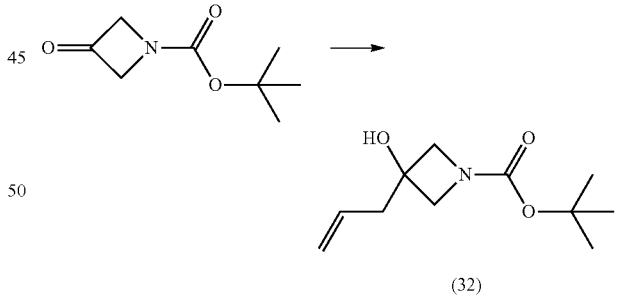

(32)

Synthesis of 3-allyl-3-hydroxy-azetidine-1-carboxylic acid tert-butyl ester (32)

3-Oxo-azetidine-1-carboxylic acid tert-butyl ester (1.37 g, 8 mmol) was dissolved in Et$_2$O (10 ml) and a 1M solution of allylmagnesiumbromid in Et$_2$O (10.4 ml, 10.4 mmol) was added dropwise at 0° C. Stirring was continued at rt overnight. The reaction mixture was quenched with H$_2$O, extracted twice with EtOAc, the organic layer were washed with brine, combined, dried over Na$_2$SO$_4$, filtered off and concentrated under reduced pressure to give a orange oil. The crude product was purified by flash chromatography (silica gel, EtOAc/cyclohexane 15-25%) which furnished the product as an yellow oil.

MS (ESI): 212 [M–H]+, 1H-NMR (CDCl3, 400 MHz) δ (ppm): 5.7 (m, 1H), 5.13 (s, 1H), 5.1 (d, 1H), 3.72 (m, 4H), 2.38 (d, 2H), 2.0 (br, 1H), 1.3 (s, 9H).

Reaction Scheme 9:

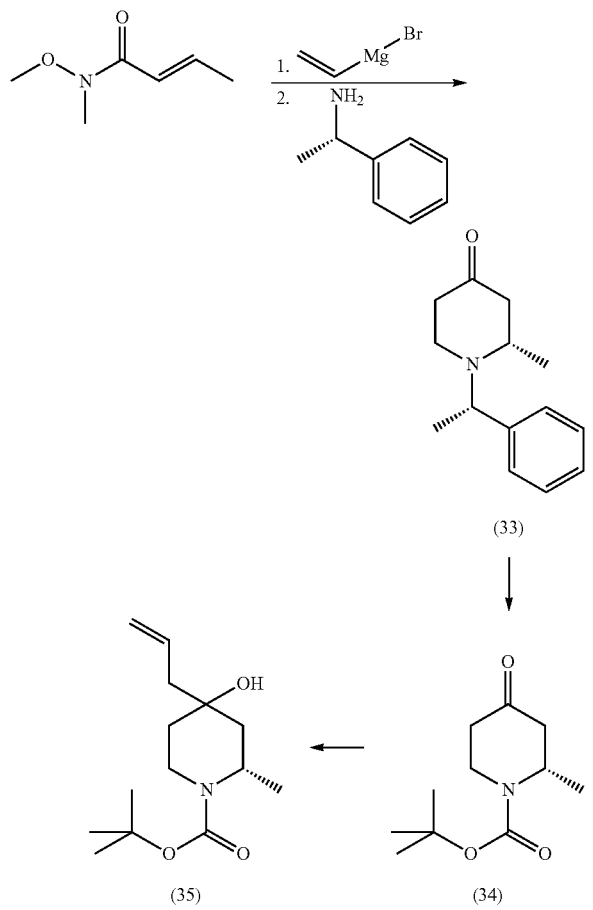

Synthesis of (S)-4-allyl-4-hydroxy-2-methyl-piperidine-1-carboxylic acid tert-butyl ester (35)

(1) Step A: (S)-2-methyl-1-((S)-1-phenyl-ethyl)-piperidin-4-one (33)

In a flame dried roundbottomflask (E)-but-2-enoic acid methoxy-methyl-amide (Einhorn et al., Synth. Commun. 20 (8), 1105-1112 (1990)) (8.0 g, 61.9 mmol) was dissolved in 150 ml of THF. A 1M solution of vinylmagnesium bromide in Et2O (68.1 ml, 68.1 mmol) was added at 0° C. and then the mixture was stirred for 1 h at rt. (S)-(−)-alpha-methylbenzylamin (15.8 ml, 124 mmol) was added at rt, followed by water (15 ml). The reaction was stirred at rt for 1 h. THF was evaporated and 150 ml of water was added. Then the mixture was extracted three times with CH2Cl2 The organic layer was washed with brine, dried over Na2 SO4 and evaporated. The crude product was purified by flash chromatography (silica gel, 20% EtOAc/cyclohexane) which furnished the (S,S) product as the first fraction (confirmed by x-ray).

MS (ESI): 218 [M+H]+, 1H-NMR (CDCl3, 400 MHz) δ (ppm): 7.2-7.6.7 (m, 5H), 4.03 (m, 1H), 3.4 (m, 1H), 2.6-2.8 (m, 2H), 2.2-2.4 (m, 2H), 1.3-1.6 (m, 2H), 1.3 (d, 3H), 1.15 (d, 3H).

(2) Step B: (S)-2-methyl-4-oxo-piperidine-1-carboxylic acid tert-butyl ester (34)

In a 2 neckroundbottomflask (S)-2-methyl-1-((S)-1-phenyl-ethyl)-piperidin-4-one (33) (0.8 g, 3.68 mmol) was dissolved in 18 ml of THF. Boc2O (964 mg, 4.42 mmol) was added under argon. Pd(OH)2 (130 mg, 0.184 mmol) was added and the reaction mixture was hydrogenated overnight at rt. The mixture was filtered over celite, rinsed with THF and evaporated. The crude product was purified by flash chromatography (silica gel, EtOAc/cyclohexane, 10-20%) which furnished the product as white solid.

MS (ESI): 214 [M+H]+, 1H-NMR (CDCl3, 400 MHz) δ (ppm): 4.71 (m, 1H), 4.24 (ddd, 1H), 3.32 (ddd, 1H), 2.68 (dd, 1H), 2.48 (ddd, 1H), 2.35 (m, 1H), 2.26 (m, 1H), 1.50 (s, 9H), 1.19 (d, 3H).

(3) Step C: (S)-4-allyl-4-hydroxy-2-methyl-piperidine-1-carboxylic acid tert-butyl ester (35)

In a argon flushed dry 25 ml 2-neckoundbottomflask (S)-2-methyl-4-oxo-piperidine-1-carboxylic acid tert-butyl ester (34) (0.6 g, 2.81 mmol) was dissolved in 10 ml of ether. A 1M solution of allylmagnesiumbromide in Et2O (3.66 ml, 3.66 mmol) was added dropwise at 0° C. The reaction mixture was stirred at 0° C. for 2 h. The mixture was quenched with NH4Cl solution and extracted with ether. The organic layer was washed with brine, dried over Na2 SO4 and evaporated. The crude product was purified by flash chromatography (silica gel, 20-30% EtOAc/cyclohexane) which furnished the product as white solid MS (ESI): 256 [M+H]+, 1H-NMR (DMSO-d6, 400 MHz) δ (ppm): 5.85 (m, 1H), 5.05 (d, 1H), 5.0 (d, 1H), 4.18 (m, 1H), 3.7 (dd, 1H), 3.1 (dd, 1H), 2.1 (d, 2H), 1.35 (s, 9H), 1.3-1.5 (m, 5H), 1.2 (d, 3H).

Reaction Scheme 10:

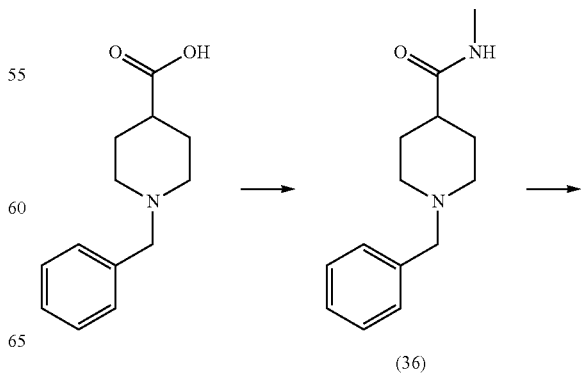

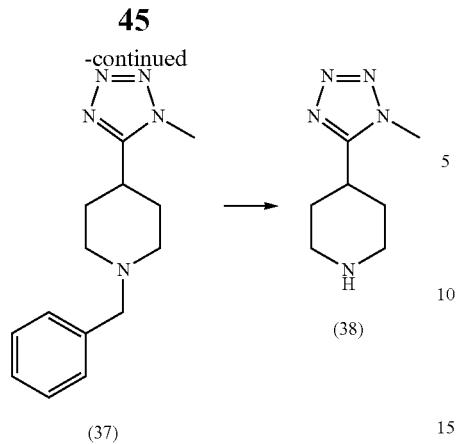

Synthesis of 4-(1-methyl-1H-tetrazol-5-yl)-piperidine (38)

(1) Step A: 1-benzyl-piperidine-4-carboxylic acid methylamide (36)

A mixture of 1-benzylpiperidine-4-carboxylic acid (1 g, 4.56 mmol), methylamine (9.12 ml of a 2N solution in THF, 18.2 mmol), 1-ethyl-3-(3-dimethylaminopropyl)carbodiimide (1.75 g, 9.1 mmol) and 1-hydroxybenzotriazole (0.7 g, 4.56 mmol) in 10 ml DMF was stirred at rt for 3 h. The reaction mixture was poured on saturated aqueous NaHCO₃ and extracted with ethyl acetate. The organic layer was washed with NaHCO₃ solution and brine, dried (Na₂ SO₄) and evaporated. Drying in vacuo gave a colorless solid which was used in the next step without further purification.

MS (ESI): 233 [M+H]$^+$, $^1$H-NMR (DMSO-d6, 500 MHz) δ (ppm): 7.65 (br d, 1H), 7.21-7.32 (m, 5H), 3.42 (s, 2H), 2.79 (m, 2H), 2.54 (d, 3H), 2.03 (m, 1H), 1.88 (m, 2H), 1.50-1.61 (m, 4H).

(2) Step B: 1-benzyl-4-(1-methyl-1H-tetrazol-5-yl)-piperidine (37)

A solution of 1-benzyl-piperidine-4-carboxylic acid methylamide (36) (853 mg, 3.67 mmol) in dichloromethane (10 ml) was cooled in an ice-bath and phosphorous pentachloride (841 mg, 4 mmol) was added dropwise. The mixture was stirred at rt for 5 h, cooled to −5° C. and trimethylsilyl azide (387 ul, 3.67 mmol) was added dropwise. The reaction mixture was stirred for 3 h at rt and was then quenched by addition of sat. aqueous NaHCO₃ solution. The organic layer was washed with water and brine, dried over Na₂ SO₄ and evaporated to yield a colorless solid.

MS (ESI): 258 [M+H]$^+$, $^1$H-NMR (DMSO-d6, 500 MHz) δ (ppm): 7.31-7.38 (m, 5H), 4.01 (s, 3H), 3.33 (br. s, 2H), 3.07 (br. m, 5H), 1.75-2.0 (br. m, 4H).

(3) Step C: 4-(1-methyl-1H-tetrazol-5-yl)-piperidine (38)

Pd(OH)₂ (20% on C, 30 mg) was added to a solution of 1-benzyl-4-(1-methyl-1H-tetrazol-5-yl)-piperidine (37) (150 mg, 0.58 mmol) in 15 ml of ethanol and the mixture was hydrogenated at 4-5 bar H₂ at 50° C. for 16 h. The catalyst was filtered off and the solvent was evaporated to give 38 as a colorless solid.

MS (ESI): 168 [M+H]$^+$, $^1$H-NMR (DMSO-d6, 500 MHz) δ (ppm): 4.02 (s, 3H), 3.17 (m, 1H), 3.09 (m, 2H), 2.70 (m, 2H), 1.86 (m, 2H), 1.68 (m, 2H).

Reaction Scheme 11:

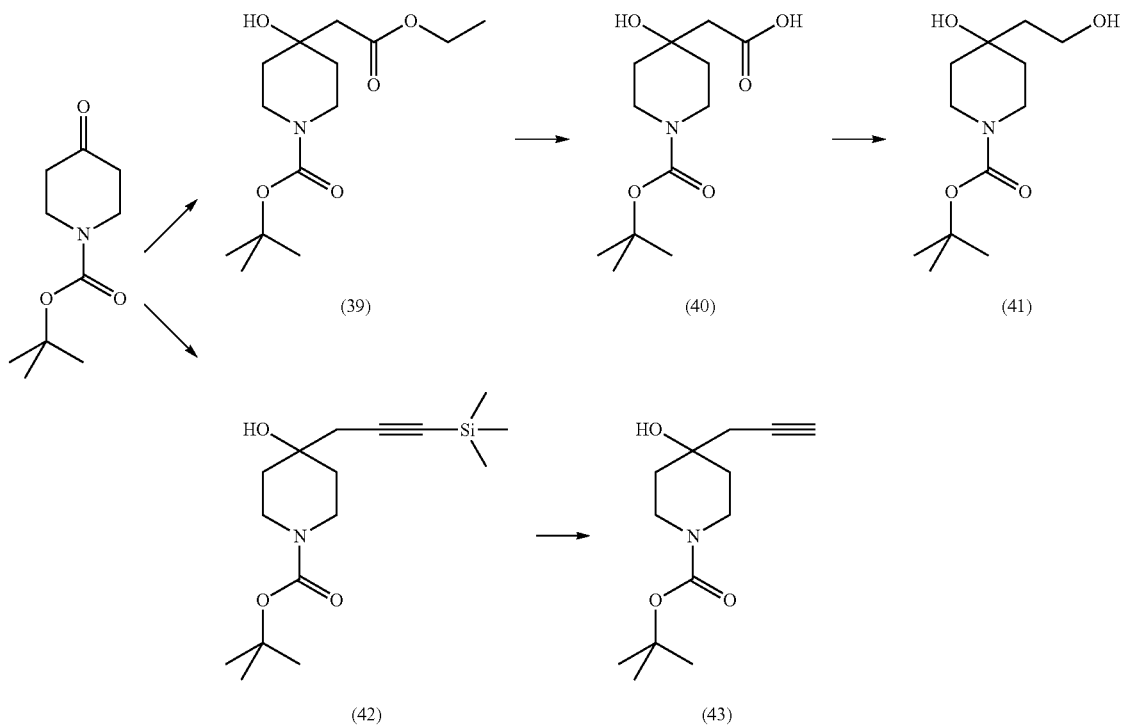

Synthesis of 4-hydroxy-4-(2-hydroxy-ethyl)-piperidine-1-carboxylic acid tert-butyl ester (41)

(1) Step A: 4-ethoxycarbonylmethyl-4-hydroxy-piperidine-1-carboxylic acid tert-butyl ester (39)

Ethyl acetate (1.95 ml, 20 mmol) was added dropwise at −78° C. to 1M solution of LiHMDS in THF (20 ml, 20 mmol). After stirring for 10 min at −78° C., 4-oxo-piperidine-1-carboxylic acid tert-butyl ester (3.98 g, 20 mmol) in 8 ml of THF was added dropwise at −78° C. and the dry ice/acetone bath was removed to allow the temperature to slowly reach 0° C. At this temperature, the reaction mixture was quenched by addition of 25 ml of $H_2O$ and the mixture was extracted twice with $Et_2O$, the organic layers were washed with brine, dried over $Na_2SO_4$ and concentrated on vacuum to give the product as an yellow oil.

MS (ESI): 286 [M−H]+, 1H-NMR (CDCl3, 400 MHz) δ (ppm): 4.17 (q, 2H), 3.81 (dt, 2H), 3.19 (dt, 2H), 2.44 (s, 2H), 1.66 (d, 2H), 1.40 (dd, 2H), 1.45 (s, 9H), 1.27 (t, 3H).

(2) Step B: 4-carboxymethyl-4-hydroxy-piperidine-1-carboxylic acid tert-butyl ester (40)

A 2M aq solution of NaOH (13.5 ml, 27 mmol) was added to a solution of 4-ethoxycarbonylmethyl-4-hydroxy-piperidine-1-carboxylic acid tert-butyl ester (39) (5.17 g, 18 mmol) at rt. After stirring at rt for 1 h, methanol was evaporated and the residue was treated with water and extracted twice with $Et_2O$, the water layer was then acidified with 2M aq solution of HCl (15 ml), extracted twice with EtOAc and the combined organic layers were dried over $Na_2SO_4$ and concentrated to provide the product as white solid.

MS (ESI): 258 [M−H]+, 1H-NMR (CDCl3, 400 MHz) δ (ppm): 3.84 (d, 2H), 3.22 (t, 2H), 2.54 (s, 2H), 1.73 (d, 2H), 1.56 (td, 2H), 1.44 (s, 9H).

(3) Step C: 4-hydroxy-4-(2-hydroxy-ethyl)-piperidine-1-carboxylic acid tert-butyl ester (41)

1M solution of borane in THF (15.8 ml, 15.8 mmol) was added slowly to a solution of 2-(1-(tert-butoxycarbonyl)-4-hydroxypiperidin-4-yl)acetic acid (40) (1.02 g, 3.94 mmol) at 0° C. After stirring the mixture at 0° C. for 1 hour and at rt for 16 hours the reaction was quenched by addition of $NH_4Cl$ solution and extracted with ethyl acetate. The organic layer was then washed with water and brine, dried over $Na_2SO_4$ and evaporated. The crude product was purified by flash chromatography (silica gel, EtOAc/n-pentane) which furnished the product as colorless oil.

MS (ESI): 246 [M+H]+; 1H-NMR (CDCl3, 400 MHz) δ (ppm): 3.96 (t, 2H), 3.78 (m, 2H), 3.23 (m, 2H), 1.76 (t, 2H) 1.70 (d, 2H), 1.49 (m, 2H), 1.47 (s, 9H).

Synthesis of 4-hydroxy-4-prop-2-ynyl-piperidine-1-carboxylic acid tert-butyl ester (43)

(1) Step A: 4-hydroxy-4-(3-trimethylsilanyl-prop-2-ynyl)-piperidine-1-carboxylic acid tert-butyl ester (42)

3-Bromopropenyl-1-trimethylsilane (1.15 g, 6.02 mmol) was dissolved in diethylether (25 ml) and cooled to 0° C. Magnesium tunings (0.195 g, 8.03 mmol) and zinc bromide (0.100 g, 0.44 mmol) were added and stirring continued for 2 h at 0° C. Tert-butyl-4-oxopiperidine-1-carboxylate (0.80 g, 4.02 mmol) was added and stirring was continued at rt for 48 h. The reaction mixture was diluted with ethylacetate and quenched with water. The organic layer was separated, washed with brine, dried and concentrated. The crude material was purified by flash chromatography on silica gel to give the title compound as a yellow oil.

1H-NMR (CDCl3, 500 MHz) δ (ppm): 3.69 (d, 2H), 3.00 3.03-2.96 (m, 2H), 2.23 (s, 1H, OH), 1.66-1.62 (m, 1H), 1.50-1.42 (m, 5), 1.29 (s, 9H), 0.00 (s, 9H).

(2) Step B: 4-hydroxy-4-prop-2-ynyl-piperidine-1-carboxylic acid tert-butyl ester (43)

4-Hydroxy-4-(3-trimethylsilanyl-prop-2-ynyl)-piperidine-1-carboxylic acid tert-butyl ester

(42) (0.49 g, 1.59 mmol) was dissolved in 10 ml of MeOH at rt. Potassium carbonate (0.66 g, 4.78 mmol) was added and stirring was continued for 2 h at rt. The reaction mixture was then diluted with ethylacetate and water, the organic layer was separated, washed with water, dried and concentrated to give the title compound as a yellow oil which was used without further purification for the next step.

1H-NMR (CDCl3, 500 MHz) δ (ppm): 5.14 (s, 1H, OH), 3.69.3.63 (m, 1H), 3.08-3.02 (m, 3H), 2.22 (s, 1H), 1.53-1.42 (m, 4H), 1.30 (s, 9H).

SYNTHESIS OF THE EXAMPLES

Reaction Scheme 12:

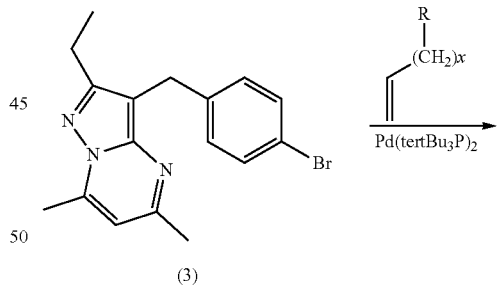

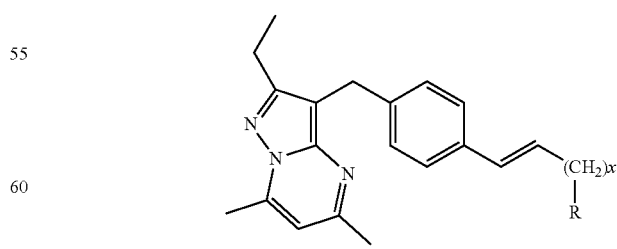

R stands for example for 4-hydroxy-piperidin-4-yl-1-carboxylic acid tert. Butylester or for other radicals as defined hereinabove for a radical R, and x is 0 or 1.

Example 1

4-{(E)-2-[4-(2-Ethyl-5,7-dimethyl-pyrazolo[1,5-a]pyrimidin-3-ylmethyl)-phenyl]-vinyl}-piperidin-4-ol

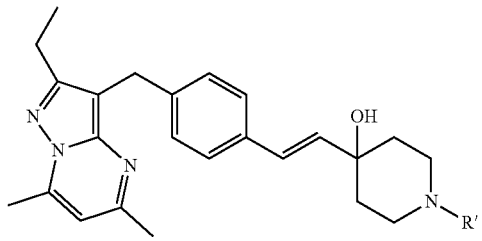

(1) Step A: 4-{(E)-2-[4-(2-ethyl-5,7-dimethyl-pyrazolo[1,5-a]pyrimidin-3-ylmethyl)-phenyl]-vinyl}-4-hydroxy-piperidine-1-carboxylic acid tert-butyl ester (R'=Boc)

4-Vinyl-4-hydroxy-piperidine-1-carboxylic acid tert-butyl ester (30) (363 mg, 1.6 mmol) was dissolved in 12 ml of dioxane and 3-(4-bromo-benzyl)-2-ethyl-5,7-dimethyl-pyrazolo[1,5-a]pyrimidine (3) (500 mg, 1.45 mmol) was added followed by diisopropylethylamine (0.5 ml, 2.9 mmol). After the mixture was flushed with argon, Pd(t-Bu₃P)₂ (14.8 mg, 0.03 mmol) was added and the mixture was stirred for 10 min. at 130° C. in a microwave oven. Then the mixture was allowed to cool down, treated with saturated NaHCO₃ solution and extracted with ethyl acertate. The organic layer was washed with water and brine and dried over Na₂ SO₄. The crude product was purified by chromatography (silica gel, cyclohexane/ethyl acetate 1:1).

MS (ESI): 491 [M+H]⁺, ¹H-NMR (DMSO-d6, 400 MHz) δ (ppm): 7.28 (d, 2H), 7.12 (d, 2H), 6.75 (s, 1H), 6.50 (d, 1H), 6.29 (d, 1H), 4.75 (s, 1H), 4.01 (s, 2H), 3.68 (m, 2H), 3.11 (brs, 2H), 2.65 (q, 2H), 2.62 (s, 3H), 2.48 (s, 3H), 1.67 (m, 2H), 1.51 (m, 4H), 1.39 (s, 9H), 1.19 (m, 2H), 1.11 (t, 3H).

(2) Step B: 4-{(E)-2-[4-(2-ethyl-5,7-dimethyl-pyrazolo[1,5-a]pyrimidin-3-ylmethyl)-phenyl]-vinyl}-piperidin-4-ol (R'=H)

4-{(E)-2-[4-(2-Ethyl-5,7-dimethyl-pyrazolo[1,5-a]pyrimidin-3-ylmethyl)-phenyl]-vinyl}-4-hydroxy-piperidine-1-carboxylic acid tert-butyl ester (190 mg, 0.387 mmol, example 1 Step A) was dissolved in 1 ml of 1-propanol and after addition of 1M aqueous Na₂ CO₃ solution (3.887 ml, 3.87 mmol) the mixture was stirred for 30 minutes at 170° C. in a microwave oven The reaction mixture was diluted with ethylacetate, washed with brine, dried over Na₂ SO₄ and evaporated under reduced pressure. The crude product was purified by preparative HPLC (acetonitrile I water).

LC/MS: 1.81 min (2.1×50 mm, HSS T3 1.7 um at 50° C., 1.2 ml/min, gradient 2-98% acetonitrile (+0.04% formic acid) in water (+0.05% formic acid+3.75 mM NH₄OAc);

MS (ESI): 391 [M+H]⁺, ¹H-NMR (DMSO-d6, 600 MHz) δ (ppm): 7.28 (d, 2H), 7.13 (d, 2H), 6.76 (s, 1H), 6.46 (d, 1H), 6.29 (d, 1H), 4.50 (br s, 1H), 4.02 (s, 2H), 2.82 (m, 2H), 2.66 (q, 2H), 2.6-2.7 (m, 2H), 2.64 (s, 3H), 2.49 (s, 3H), 1.54 (m, 2H), 1.44 (m, 2H), 1.12 (t, 3H).

Example 2

3-{(E)-3-[4-(2-Ethyl-5,7-dimethyl-pyrazolo[1,5-a]pyrimidin-3-ylmethyl)-phenyl]-allyl}-azetidin-3-ol

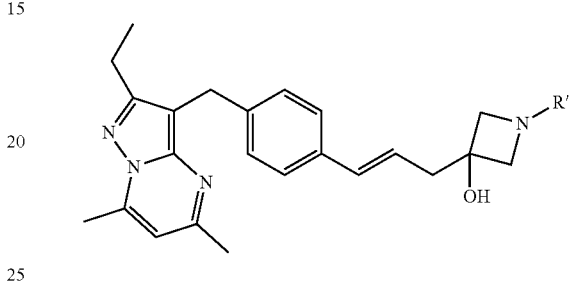

(1) Step A: 3-{(E)-3-[4-(2-ethyl-5,7-dimethyl-pyrazolo[1,5-a]pyrimidin-3-ylmethyl)-phenyl]-allyl}-3-hydroxy-azetidine-1-carboxylic acid tert-butyl ester (R'=Boc)

This compound was synthesized analogously to example 1 step A using 3-allyl-3-hydroxy-azetidine-1-carboxylic acid tert-butyl ester (32).

MS (ESI): 477 [M+H]⁺, ¹H-NMR (DMSO-d6, 400 MHz) δ (ppm): 7.22 (d, 2H), 7.10 (d, 2H), 6.72 (s, 1H), 6.40 (d, 1H), 6.19 (dt, 1H), 5.67 (s, 1H), 4.01 (m, 2H), 3.99 (s, 2H), 3.71 (m, 2H), 3.62 (m, 2H), 2.65 (q, 2H), 2.61 (s, 3H), 2.46 (s, 3H), 1.33 (s, 9H), 1.11 (t, 3H).

(2) Step B: 3-{(E)-3-[4-(2-ethyl-5,7-dimethyl-pyrazolo[1,5-a]pyrimidin-3-ylmethyl)-phenyl]-allyl}-azetidin-3-ol (R'=H)

3-{(E)-3-[4-(2-Ethyl-5,7-dimethyl-pyrazolo[1,5-a]pyrimidin-3-ylmethyl)-phenyl]-allyl}-3-hydroxy-azetidine-1-carboxylic acid tert-butyl ester (47.7 mg, 0.1 mmol) was dissolved in 1 ml of 95% CF₃ COOH and stirred for 30 min at 0° C. The solvent was evaporated at rt under reduced pressure, treated with 1M Na₂ CO₃ solution and extracted twice with CH₂Cl₂. The organic layer was washed with water, dried over Na₂ SO₄ and evaporated under reduced pressure to give a yellow oil. The crude was further purified by preparative TLC (CH₂Cl₂/CH₃OH/NH₃ conc.=80:18:2).

LC/MS: 1.64 min (2.1×50 mm, HSS T3 1.8 um at 50° C., 1.2 ml/min, gradient 2-98% acetonitrile (+0.04% formic acid) in water (+0.05% formic acid+3.75 mM NH₄OAc);

MS (ESI): 377 [M+H]⁺, ¹H-NMR (DMSO-d6, 400 MHz) δ (ppm): 7.25 (d, 2H), 7.11 (d, 2H), 6.75 (s, 1H), 6.40 (d, 1H), 6.24 (dt, 1H), 5.35 (brs, 1H), 4.00 (s, 2H), 3.41 (d, 2H), 3.26 (d, 2H), 2.66 (q, 2H), 2.62 (s, 3H), 2.48 (s, 3H), 1.12 (t, 3H).

Example 3

4-{(E)-3-[4-(2-Ethyl-5,7-dimethyl-pyrazolo[1,5-a]pyrimidin-3-ylmethyl)-phenyl]-allyl}-piperidin-4-ol

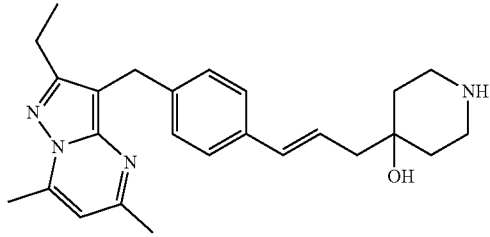 [SMILES: CCc1nn2c(C)cc(C)nc2c1Cc1ccc(/C=C/CC2(O)CCNCC2)cc1]

(1) Step A: 4-{(E)-3-[4-(2-ethyl-5,7-dimethyl-pyrazolo[1,5-a]pyrimidin-3-ylmethyl)-phenyl]-allyl}-4-hydroxy-piperidine-1-carboxylic acid tert-butyl ester (R'=Boc)

This compound was synthesized analogously to example 1 step A using 4-allyl-4-hydroxy-piperidine-1-carboxylic acid tert-butyl ester (31).

MS (ESI): 505 [M+H]+, 1H-NMR (DMSO-d6, 400 MHz) δ (ppm): 7.25 (d, 2H), 7.11 (d, 2H), 6.75 (s, 1H), 6.33 (d, 1H), 6.20-6.28 (m, 1H), 4.41 (s, 1H), 4.00 (m, 2H), 3.61 (d, 2H), 3.05 (brs, 2H), 2.66 (q, 2H), 2.63 (s, 3H), 2.48 (s, 3H), 2.26 (d, 2H), 1.39 (m, 4H), 1.37 (s, 9H), 1.12 (t, 3H).

(2) Step B: 4-{(E)-3-[4-(2-ethyl-5,7-dimethyl-pyrazolo[1,5-a]pyrimidin-3-ylmethyl)-phenyl]-allyl}-piperidin-4-ol 4-{(E)-3-[4-(2-Ethyl-5,7-dimethyl-pyrazolo[1,5-a]pyrimidin-3-ylmethyl)-phenyl]-allyl}-4-hydroxy-piperidine-1-carboxylic acid tert-butyl ester (step A) (555 mg, 1.1 mmol)) was dissolved in 4M HCl in dioxane (11 ml) and stirred for 1 h at rt. The reaction mixture was then evaporated under reduced pressure and purified by flash chromatography (silica gel, CH$_2$Cl$_2$/CH$_3$OH/NH$_3$ conc. 90:9:1).

LC/MS: 1.95 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 405 [M+H]+, 1H-NMR (DMSO-d6, 400 MHz) δ (ppm): 7.25 (d, 2H), 7.11 (d, 2H), 6.75 (s, 1H), 6.18-6.36 (m, 2H), 4.19 (s, 1H), 4.00 (s, 2H), 2.76 (m, 2H), 2.66 (q, 2H), 2.62 (s, 3H), 2.60 (m, 2H), 2.48 (s, 3 H), 2.23 (d, 2H), 1.37 (m, 4H), 1.12 (t, 3H).

Example 4

4-{3-[4-(2-Ethyl-5,7-dimethyl-pyrazolo[1,5-a]pyrimidin-3-ylmethyl)-phenyl]-propyl}-piperidin-4-ol hydrochloride

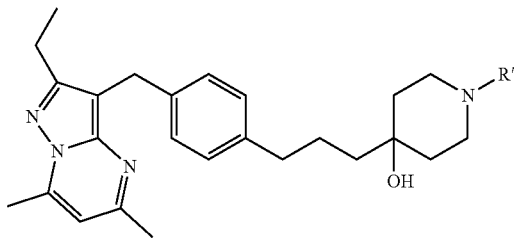

(1) Step A: 4-{3-[4-(2-ethyl-5,7-dimethyl-pyrazolo[1,5-a]pyrimidin-3-ylmethyl)-phenyl]-propyl}-4-hydroxy-piperidine-1-carboxylic acid tert-butyl ester (R'=Boc)

Example 3 step B (316 mg, 0.63 mmol) was dissolved in 12 ml of methanol. After addition of 10% Pd—C (31.6 mg) the mixture was hydrogenated at rt for 12 h. Then the reaction mixture was filtrated through celite and evaporated under reduced pressure. The crude product was purified by chromatography (EtOAc/heptane 20-40%).

MS (ESI): 507 [M+H]+, 1H-NMR (DMSO-d6, 400 MHz) δ (ppm): 7.06 (m, 4H), 6.74 (s, 1H), 4.14 (s, 1H), 3.98 (s, 2H), 3.55 (m, 2H), 3.44 (m, 2H), 3.02 (brs, 2H), 2.65 (q, 2H), 2.62 (s, 3H), 2.47 (s, 3H), 1.56 (m, 2H), 1.37 (s, 9H), 1.28-1.35 (m, 4H), 1.10 (t, 3H), 0.84 (m, 2H).

(2) Step B: 4-{3-[4-(2-ethyl-5,7-dimethyl-pyrazolo[1,5-a]pyrimidin-3-ylmethyl)-phenyl]-propyl}-piperidin-4-ol This compound was synthesized from step A analogously to example 3 step B.

LC/MS: 0.86 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 407 [M+H]+, 1H-NMR (DMSO-d6, 500 MHz) δ (ppm): 8.60 (brs, 1H), 8.41 (brs, 1H), 7.08 (d, 2H), 7.05 (d, 2H), 6.75 (s, 1H), 5.75 (s, 1H), 3.99 (s, 2H), 3.38 (m, 2H), 3.03 (brs, 4H), 2.66 (q, 2H), 2.62 (s, 3H), 2.48 (s, 3H), 1.52-1.58 (m, 4H), 1.33-1.41 (m, 2H), 1.11 (s, 3H), 0.84 (m, 2H).

Example 5

(2S,4S)-4-{(E)-3-[4-(2-Ethyl-5,7-dimethyl-pyrazolo[1,5-a]pyrimidin-3-ylmethyl)-phenyl]-allyl}-2-methyl-piperidin-4-ol

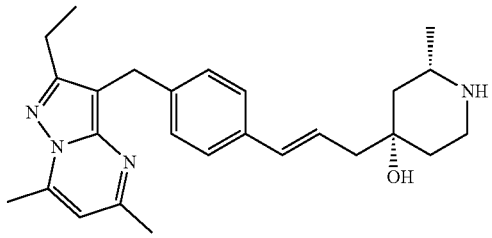 [SMILES: CCc1nn2c(C)cc(C)nc2c1Cc1ccc(/C=C/C[C@]2(O)CCN[C@@H](C)C2)cc1]

This compound was synthesized analogously to example 1 step A using (S)-4-allyl-4-hydroxy-2-methyl-piperidine-1-carboxylic acid tert-butyl ester (35) followed by Boc-deprotection analogously to example 3 step B.

LC/MS: 1.98 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 419 [M+H]+, 1H-NMR (DMSO-d6, 400 MHz) δ (ppm): 7.24 (d, 2H), 7.11 (d, 2H), 6.75 (s, 1H), 6.21-6.36 (m, 2H), 4.32 (s, 1H), 4.00 (s, 2H), 2.78 (m, 1H), 2.66 (q, 2H), 2.63 (s, 3H), 2.57 (m, 1H), 2.48 (s, 3H), 2.34 (m, 2H), 1.55 (m, 2H), 1.28 (ddd, 1H), 1.17 (m, 1H), 1.13 (t, 3H), 0.98 (dd, 1H), 0.92 (d, 3H).

Reaction Scheme 13:

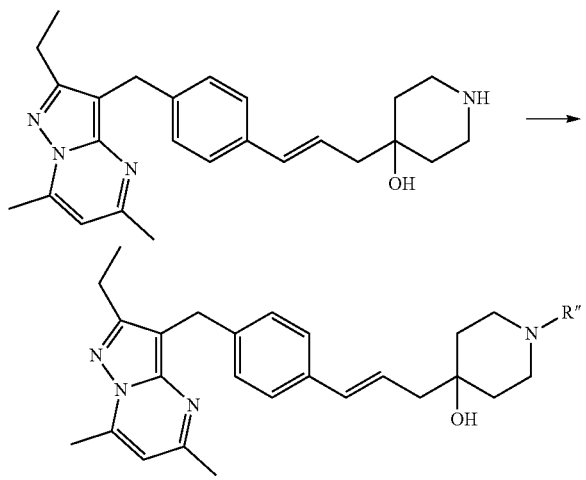

Starting from example No. 3 and in accordance to scheme 13, a substituent R" may be introduced as shown in the following examples 6 and 7, utilizing for example a reductive amination procedure (example 6), or a standard coupling reaction of an amine with a carboxylic acid (example 7).

Example 6

(R)-3-(4-{(E)-3-[4-(2-Ethyl-5,7-dimethyl-pyrazolo [1,5-a]pyrimidin-3-ylmethyl)-phenyl]-allyl}-4-hydroxy-piperidin-1-yl)-propane-1,2-diol

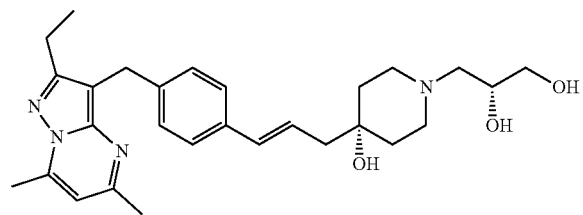

4-{(E)-3-[4-(2-Ethyl-5,7-dimethyl-pyrazolo[1,5-a]pyrimidin-3-ylmethyl)-phenyl]-allyl}-piperidin-4-ol (example 3) (100 mg, 0.247 mmol), (S)-2,3-dihydroxypropanal (22.3 mg, 0.247 mmol), NaBH(OAc)$_3$ (81 mg, 0.383 mmol) and DIPEA (0.050 ml, 0.287 mmol) were dissolved in 1.5 ml of dichloroethane and stirred for 3 h at 70° C. Then the mixture was diluted with EtOAc, washed with NaCl-solution and dried over Na$_2$SO$_4$. Evaporation gave a yellow oil. The crude product was purified by chromatography (silica gel, MeOH, EtOAc).

LC/MS: 1.75 min (2.1×50 mm, HSS T3 1.8 um at 50° C., 1.2 ml/min, gradient 2-98% acetonitrile (+0.04% formic acid) in water (+0.05% formic acid+3.75 mM NH$_4$OAc);

MS (ESI): 479 [M+H]$^+$, $^1$H-NMR (DMSO-d6, 600 MHz) δ (ppm): 7.26 (d, 2H), 7.12 (d, 2H), 6.76 (s, 1H), 6.33 (d, 1H), 6.28 (m, 1H), 4.55 (br s, 1H), 4.3 (br, 1H), 4.17 (br, 1H), 4.01 (s, 2H), 3.57 (m, 1H), 3.32 (m, 2H), 2.68 (q, 2H), 2.64 (s, 3H), 2.49 (s, 3H), 2.35 (m, 4H), 2.32 (m, 1H), 2.25 (m, 2H), 2.23 (m, 1H), 1.44 (m, 4H), 1.13 (t, 3H).

Example 7

1-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-methylamino-ethanone hydrochloride

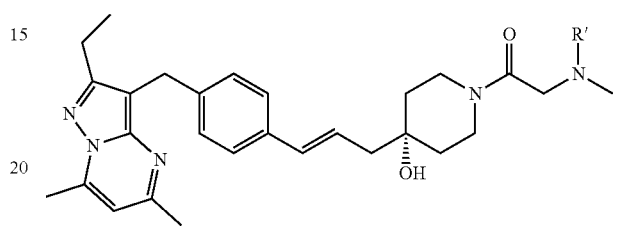

(1) Step A: [2-(4-{(E)-3-[4-(2-ethyl-5,7-dimethyl-pyrazolo[1,5-a]pyrimidin-3-ylmethyl)-phenyl]-allyl}-4-hydroxy-piperidin-1-yl)-2-oxo-ethyl]-methyl-carbamic acid tert-butyl ester (R'=Boc)

4-{(E)-3-[4-(2-Ethyl-5,7-dimethyl-pyrazolo[1,5-a]pyrimidin-3-ylmethyl)-phenyl]-allyl}-piperidin-4-ol (example 3) (150 mg, 0.371 mmol), 2-(tert-butoxycarbonyl (methyl) amino) acetic acid (70.2 mg, 0.371 mmol), EDC (107 mg, 0.556 mmol), HOBT (68.1 mg, 0.445 mmol) and NEt$_3$ (0.067 ml, 0.482 mmol) were dissolved in 8 ml of DMF and stirred for 3 h at 60° C. Then the mixture was diluted with EtOAc, washed with NaCl-solution and dried over Na$_2$SO$_4$. Evaporation gave a brown oil. The crude product was purified by chromatography (silicagel, EtOAc/cyclo hexane).

MS (ESI): 576 [M+H]$^+$, $^1$H-NMR (DMSO-d6, 600 MHz) δ (ppm): 7.25 (d, 2H), 7.12 (d, 2H), 6.75 (m, 1H), 6.30 (m, 1H), 6.23 (m, 1H), 4.53 (d, 1H), 4.00 (s, 2H), 3.6-4.0 (m, 2H), 3.47 (m, 1H), 3.25 (m, 2H), 2.94 (m, 1H), 2.72 (m, 3H), 2.65 (q, 2H), 2.62 (s, 3H), 2.48 (s, 3H), 2.27 (m, 2H), 1.45 (m, 4H), 1.24 (s, 9H), 1.12 (t, 3H).

(2) Step B: 1-(4-{(E)-3-[4-(2-ethyl-5,7-dimethyl-pyrazolo[1,5-a]pyrimidin-3-ylmethyl)-phenyl]-allyl}-4-hydroxy-piperidin-1-yl)-2-methylamino-ethanone dihydrochloride (R'=H)

This compound was synthesized from step A analogously to example 3 step B.

LC/MS: 1.83 min (2.1×50 mm, HSS T3 1.8 um at 50° C., 1.2 ml/min, gradient 2-98% acetonitrile (+0.04% formic acid) in water (+0.05% formic acid+3.75 mM NH$_4$OAc);

MS (ESI): 476 [M+H]$^+$, $^1$H-NMR (DMSO-d6, 600 MHz) δ (ppm): 8.74 (br, 2H), 7.27 (d, 2H), 7.13 (d, 2H), 6.77 (m, 1H), 6.33 (d, 1H), 6.27 (m, 1H), 3.95-4.1 (m, 5H), 4.02 (s, 2H), 3.3 (m, 1H), 3.03 (m, 1H), 2.68 (q, 2H), 2.64 (s, 3H), 2.54 (m, 3H), 2.49 (s, 3H), 2.31 (d, 2H), 1.51 (m, 2H), 1.35 (m, 1H), 1.13 (t, 3H), 1.05 (m, 1H).

Reaction Scheme 14:

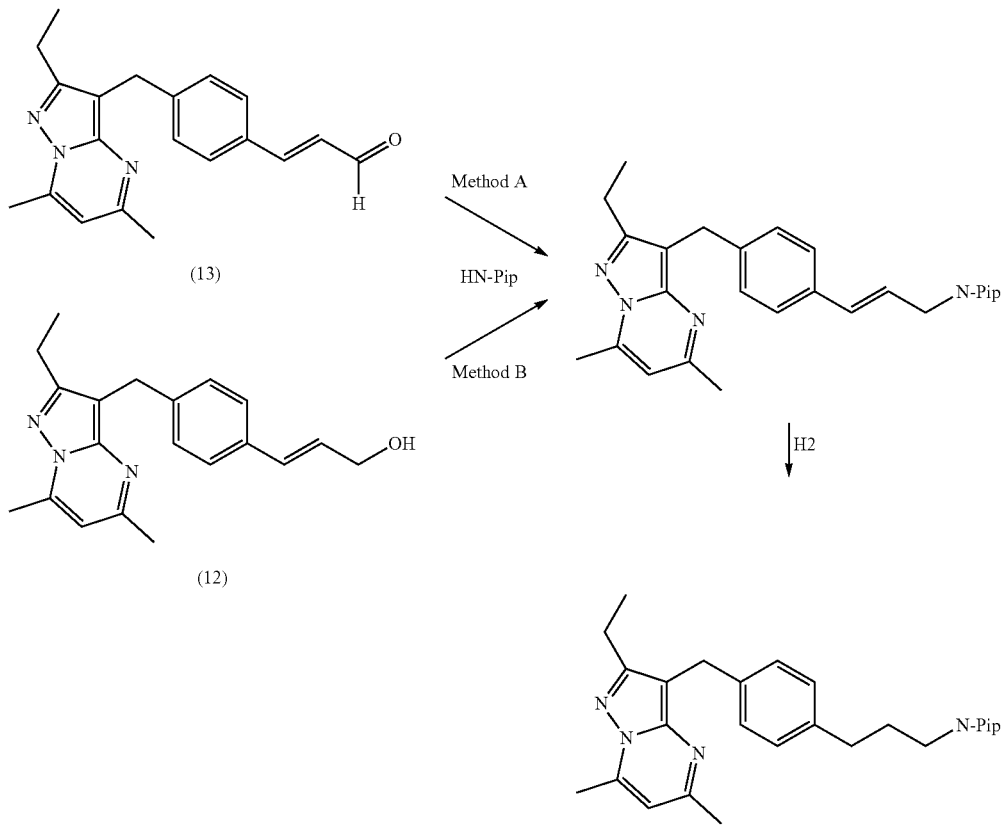

HN-Pip denotes a Piperidine- or a piperazine moiety optionally further substituted Method A relates to a reductive amination procedure, and Method B relates to an N-alkylation of an alcohol with an amine derivative by using for example the Zaragoza reagent.

Example 8

((S)-4-{(E)-3-[4-(2-Ethyl-5,7-dimethyl-pyrazolo[1,5-a]pyrimidin-3-ylmethyl)-phenyl]-allyl}-piperazin-2-yl)-methanol dihydrochloride (Method A)

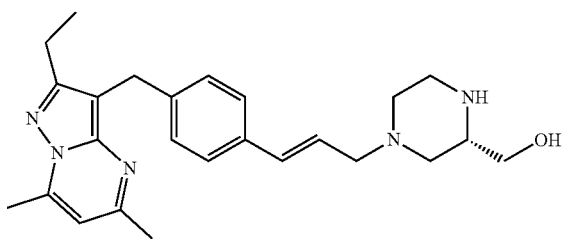 [SMILES: CCc1nn2c(C)cc(C)nc2c1Cc1ccc(/C=C/CN2CCN[C@H](CO)C2)cc1]

(E)-3-[4-(2-Ethyl-5,7-dimethyl-pyrazolo[1,5-a]pyrimidin-3-ylmethyl)-phenyl]-propenal (7) (100 mg, 0.313 mmol), (R)-tert-butyl 2-(hydroxymethyl)piperazine-1-carboxylate (67.7 mg, 0.313 mmol), NaBH(OAc)$_3$ (103 mg, 0.485 mmol) and DIPEA (0.063 ml, 0.363 mmol) were dissolved in 2 ml of dichlorethane and stirred for 4 h at rt. Then the mixture was diluted with EtOAc, washed with NaCl-solution and dried over Na$_2$ SO$_4$. Evaporation gave a yellow oil.

The crude product was purified by chromatography (silica gel, ethyl acetate/methanol) to yield a white foam. Boc deprotection was performed analogously to example 3 step B.

LC/MS: 1.77 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 420 [M+H]$^+$, $^1$H-NMR (DMSO-d6, 600 MHz) δ (ppm): 12.5 (br, 1H), 10.3 (br, 1H), 9.9 (br, 1H), 7.37 (d, 2H), 7.22 (d, 2H), 6.85 (d, 1H), 6.83 (s, 1H), 6.32 (m, 1H), 4.10 (s, 2H), 3.97 (m, 3H), 3.6-3.75 (m, 3H), 3.1-3.5 (m, 6H), 2.67 (q, 2H), 2.66 (s, 3H), 2.53 (s, 3H), 1.12 (t, 3H).

Example 9

2-Ethyl-5,7-dimethyl-3-{4-[(E)-3-((S)-3-methyl-piperazin-1-yl)-propenyl]-benzyl}-pyrazolo[1,5-a]pyrimidine (Method B)

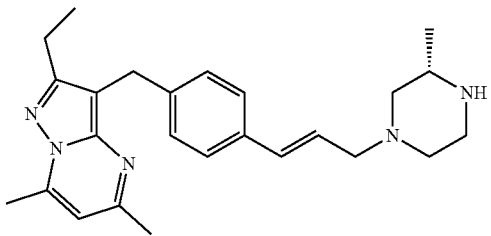 [SMILES: CCc1nn2c(C)cc(C)nc2c1Cc1ccc(/C=C/CN2CCN[C@@H](C)C2)cc1]

(E)-3-[4-(2-Ethyl-5,7-dimethyl-pyrazolo[1,5-a]pyrimidin-3-ylmethyl)-phenyl]-prop-2-en-1-ol (6) (100 mg, 0.311 mmol) was dissolved in 2 ml of propionitril and after addition of (S)-2-methyl-piperazine (31.2 mg, 0.311 mmol), DIPEA (0.272 ml, 1.556 mmol) and (cyanomethyl)-trimethylphosphonium iodide (Zaragoza reagent) (178 mg, 0.778 mmol) the mixture was stirred for 2 h at 95° C. Then the mixture was evaporated under reduced pressure (HV). The residue was diluted with ethyl acetate, washed with 5% NaHCO₃— and NaCl-solution and dried over Na₂ SO₄. Evaporation gave a brown oil. The crude product was purified by chromatography (silica gel, ethyl acetate/then methanol) to yield a beige oil.

LC/MS: 1.69 min (2.1×50 mm, HSS T3 1.8 um at 50° C., 1.2 ml/min, gradient 2-98% acetonitrile (+0.04% formic acid) in water (+0.05% formic acid+3.75 mM NH₄OAc);

MS (ESI): 404 [M+H]⁺, ¹H-NMR (DMSO-d6, 600 MHz) δ (ppm): 7.28 (d, 2H), 7.10 (d, 2H), 6.74 (d, 1H), 6.43 (d, 1H), 6.18 (dt, 1H), 4.0 (s, 2H), 3.0 (m, 2H), 2.6-2.8 (m, 6H), 2.65 (q, 2H), 2.62 (s, 3H), 2.5 (s, 3H), 1.85 (m, 1H), 1.55 (m, 1H), 1.1 (t, 3H), 0.9 (d, 3H).

Example 10

2-Ethyl-3-{4-[(E)-3-((S)-3-methoxymethyl-piperazin-1-yl)-propenyl]-benzyl}-5,7-dimethyl-pyrazolo[1,5-a]pyrimidine (Method A)

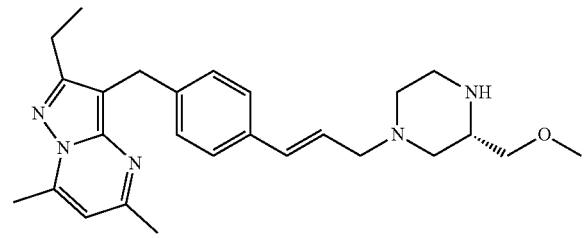

This compound was synthesized analogously to example 8 using (R)-tert-butyl 2-(methoxymethyl)piperazine-1-carboxylate.

LC/MS: 4.77 min (2.1×50 mm, HSS T3 1.7 um at 50° C., 1.2 ml/min, gradient 2-98% acetonitrile (+0.04% formic acid) in water (+0.05% formic acid+3.75 mM NH₄OAc);

MS (ESI): 434 [M+H]⁺, ¹H-NMR (DMSO-d6, 600 MHz) δ (ppm): 7.30 (d, 2H), 7.14 (d, 2H), 6.76 (s, 1H), 6.46 (d, 1H), 6.17 (dt, 1H), 4.02 (s, 2H), 3.29 (m, 3H), 3.24 (s, 3H), 3.08 (m, 2H), 3.00 (m, 1H), 2.93 (m, 1H), 2.79 (m, 1H), 2.76 (m, 2H), 2.68 (q, 2H), 2.64 (s, 3H), 2.49 (s, 3H), 2.05 (m, 1H), 1.81 (m, 1H), 1.13 (t, 3H).

Example 11

2-Amino-1-(4-{(E)-3-[4-(2-ethyl-5,7-dimethyl-pyrazolo[1,5-a]pyrimidin-3-ylmethyl)-phenyl]-allyl}-piperazin-1-yl)-ethanone dihydrochloride (Method B)

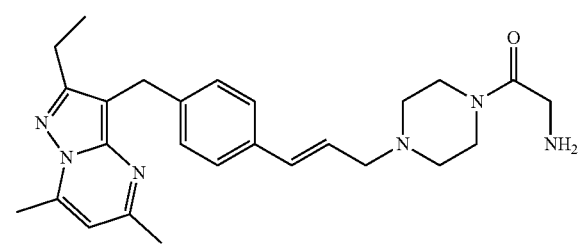 [SMILES: CCc1nn2c(C)cc(C)nc2c1Cc1ccc(/C=C/CN2CCN(C(=O)CN)CC2)cc1]

This compound was synthesized analogously to example 9 (method B) using tert-butyl 2-oxo-2-(piperazin-1-yl)ethyl-carbamate followed by Boc-deprotection analogously to example 3 step B.

LC/MS: 1.29 min (2.1×50 mm, HSS T3 1.7 um at 50° C., 1.2 ml/min, gradient 2-98% acetonitrile (+0.04% formic acid) in water (+0.05% formic acid+3.75 mM NH₄OAc);

MS (ESI): 447 [M+H]⁺, ¹H-NMR (DMSO-d6, 500 MHz) δ (ppm): 11.6 (br, 1H), 8.20 (br s, 3H), 7.35 (d, 2H), 7.20 (d, 2H), 6.76 (s, 1H), 6.74 (d, 1H), 6.31 (dt, 1H), 4.40 (m, 1H), 4.03 (s, 2H), 3.93 (m, 1H), 3.87 (m, 4H), 3.52 (m, 1H), 3.45 (m, 2H), 3.19 (m, 1H), 3.05 (m, 1H), 2.91 (m, 1H), 2.66 (q, 2H), 2.62 (s, 3H), 2.47 (s, 3H), 1.11 (t, 3H).

Example 12

2-Ethyl-5,7-dimethyl-3-(4-{(E)-3-[4-(1-methyl-1H-tetrazol-5-yl)-piperidin-1-yl]-propenyl}-benzyl)-pyrazolo[1,5-a]pyrimidine hydrochloride (Method A)

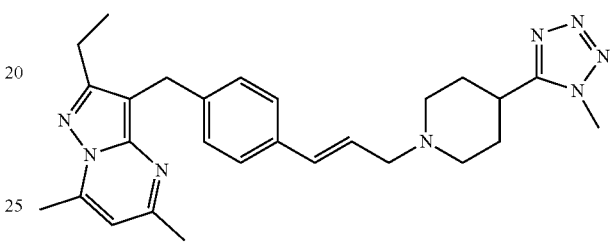

This compound was synthesized analogously to example 8 using 4-(1-methyl-1H-tetrazol-5-yl)-piperidine (38).

LC/MS: 1.77 min (2.1×50 mm, HSS T3 1.8 um at 50° C., 1.2 ml/min, gradient 2-98% acetonitrile (+0.04% formic acid) in water (+0.05% formic acid+3.75 mM NH₄OAc);

MS (ESI): 471 [M+H]⁺, ¹H-NMR (DMSO-d6, 500 MHz) δ (ppm): 7.31 (d, 2H), 7.12 (d, 2H), 6.75 (s, 1H), 6.46 (d, 1H), 6.22 (dt, 1H), 4.00 (2s, 5H), 3.09 (d, 2H), 2.98 (m, 1H), 2.93 (m, 2H), 2.65 (q, 2H), 2.62 (s, 3H), 2.47 (s, 3H), 2.08 (t, 2H), 1.97 (d, 2H), 1.67-1.76 (m, 2H).

Example 13

((S)-4-{(E)-3-[4-(2-Ethyl-5,7-dimethyl-pyrazolo[1,5-a]pyrimidin-3-ylmethyl)-phenyl]-allyl}-piperazin-2-ylmethyl)-dimethyl-amine trihydrochloride (Method B)

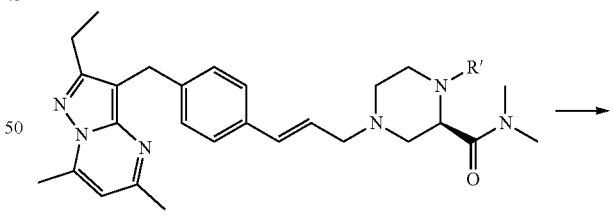

Step A

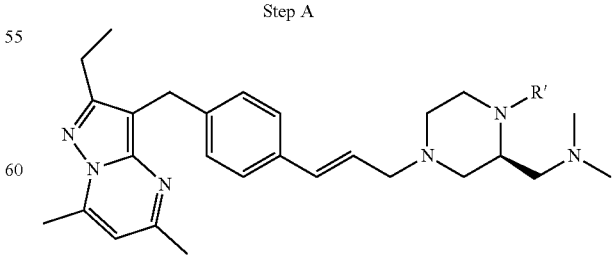

Step B (R' = Boc)
Step C (R' = H)

(1) Step A: (R)-2-dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester, R'=Boc This compound was synthesized analogously to example 8 using (R)-tert-butyl 2-(dimethylcarbamoyl)piperazine-1-carboxylate.

MS (ESI): 561 [M+H]+, 1H-NMR (DMSO-d6, 500 MHz) δ (ppm): 7.28 (d, 2H), 7.14 (d, 2H), 6.76 (s, 1H), 6.43 (d, 1H), 6.15 (dt, 1H), 4.76 (br d, 1H), 4.02 (s, 2H), 3.58 (m, 2H), 3.03 (m, 4H), 2.92 (br s, 3H), 2.81 (br s, 3H), 2.68 (q, 2H), 2.64 (s, 3H), 2.49 (s, 3H), 2.20 (m, 1H), 1.92 (m, 1H), 1.38 (br s, 9H), 1.13 (t, 3H).

(2) Step B: (S)-2-dimethylaminomethyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester (R'=Boc)

(R)-2-Dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester (step A) (80 mg, 0.143 mmol) was dissolved in 1 ml of $CH_2Cl_2$ and cooled to −78° C. After addition of DIBAH (1.577 ml, 1.577 mmol) the mixture was stirred for 3 h at −78° C. Then the mixture was quenched with water and filtrated over celite. Then it was extracted with ethyl acetate, washed with water and NaCl-solution, dried over $Na_2SO_4$ and evaporated. The crude product was purified by chromatography, ethyl acetate/methanol to yield a white solid.

MS (ESI): 547 [M+H]+, 1H-NMR (DMSO-d6, 500 MHz) δ (ppm): 7.29 (d, 2H), 7.13 (d, 2H), 6.75 (s, 1H), 6.46 (d, 1H), 6.15 (dt, 1H), 4.01 (s, 2H), 3.70 (d, 1H), 3.06 (dd, 1H), 3.00 (dd, 1H), 2.89 (m, 1H), 2.76 (m, 1H), 2.6-2.7 (m, 4H), 2.66 (q, 2H), 2.62 (s, 3H), 2.48 (s, 3H), 2.21 (br, 6H), 1.91 (m, 2H), 1.39 (s, 9H), 1.12 (t, 3H).

(3) Step C: ((S)-4-{(E)-3-[4-(2-ethyl-5,7-dimethyl-pyrazolo[1,5-a]pyrimidin-3-ylmethyl)-phenyl]-allyl}-piperazin-2-ylmethyl)-dimethyl-amine (R'=H)

This compound was synthesized from step B analogously to example 3 step B.

LC/MS: 1.38 min (2.1×50 mm, HSS T3 1.8 um at 50° C., 1.2 ml/min, gradient 2-98% acetonitrile (+0.04% formic acid) in water (+0.05% formic acid+3.75 mM $NH_4OAc$);

MS (ESI): 447 [M+H]+, 1H-NMR (DMSO-d6, 600 MHz) δ (ppm): 7.39 (d, 2H), 7.21 (d, 2H), 6.85 (m, 1H), 6.79 (s, 1H), 6.31 (m, 1H), 4.06 (s, 2H), 3.5-4.0 (m, 12H), 2.88 (s, 6H), 2.67 (q, 2H), 2.64 (s, 3H), 2.51 (s, 3H), 1.13 (t, 3H).

Example 14

2-Ethyl-5,7-dimethyl-3-[4-((E)-3-piperazin-1-yl-propenyl)-benzyl]-pyrazolo[1,5-a]pyrimidine (Method B)

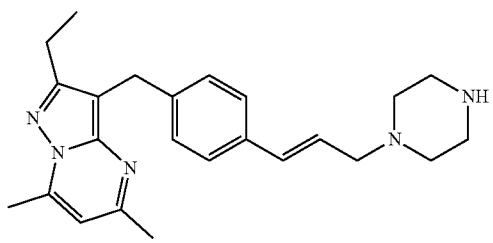 [SMILES: CCc1nn2c(C)cc(C)nc2c1Cc1ccc(/C=C/CN2CCNCC2)cc1]

This compound was synthesized analogously to example 8 using piperazine-1-carboxylic acid tert-butyl ester followed by Boc-deprotection analogously to example 3 step B.

LC/MS: 1.85 min (2.1×50 mm, HSS T3 1.8 um at 50° C., 1.2 ml/min, gradient 2-98% acetonitrile (+0.04% formic acid) in water (+0.05% formic acid+3.75 mM $NH_4OAc$);

MS (ESI): 390 [M+H]+, 1H-NMR (DMSO-d6, 500 MHz) δ (ppm): 10.01 (br, 1H), 7.36 (d, 2H), 7.22 (d, 2H), 6.86 (s, 1H), 6.82 (m, 1H), 6.32 (m, 1H), 4.09 (s, 2H), 3.95 (d, 2H), 3.25-3.7 (m, 8H), 2.67 (q, 2H), 2.66 (s, 3H), 2.51 (s, 3H), 1.12 (t, 3H).

Reaction Scheme 15:

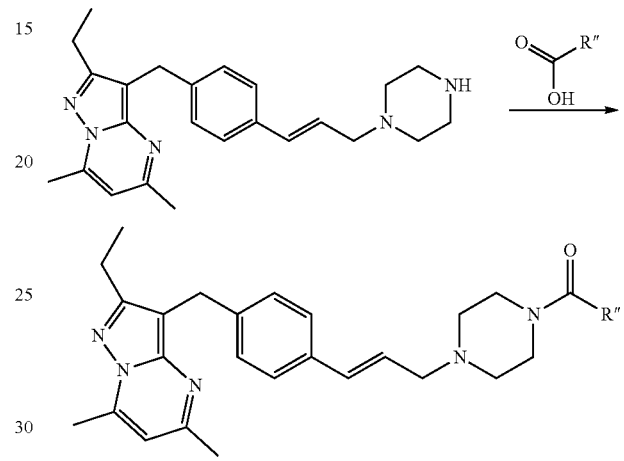

Scheme 15 describes the "peptide" coupling reaction of a carboxylic acid derivative with the amine substrate, wherein_R" denotes said carboxylic acid derivative without its hydroxy group as being described in the following examples 15 and 16

Example 15

(S)-1-(4-{(E)-3-[4-(2-Ethyl-5,7-dimethyl-pyrazolo[1,5-a]pyrimidin-3-ylmethyl)-phenyl]-allyl}-piperazin-1-yl)-3-hydroxy-2-methylamino-propan-1-one

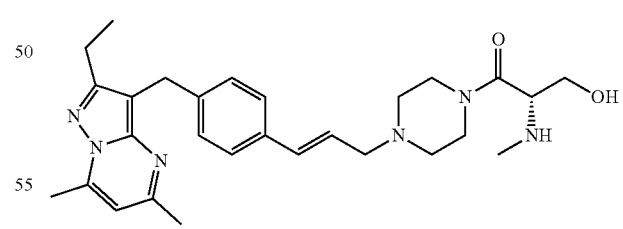

This compound was synthesized from example 14 analogously to example 7 step A using (S)-3-hydroxy-2-(methylamino)propanoic acid.

LC/MS: 1.50 min (2.1×50 mm, HSS T3 1.7 um at 50° C., 1.2 ml/min, gradient 2-98% acetonitrile (+0.04% formic acid) in water (+0.05% formic acid+3.75 mM $NH_4OAc$);

MS (ESI): 491 [M+H]+, 1H-NMR (DMSO-d6, 500 MHz) δ (ppm): 7.31 (d, 2H), 7.13 (d, 2H), 6.75 (s, 1H), 6.46 (d, 1H), 6.21 (dt, 1H), 4.01 (s, 2H), 3.25-3.7 (m, 9H), 3.07 (d, 2H), 2.67 (q, 2H), 2.62 (s, 3H), 2.48 (s, 3H), 2.35 (m, 4H), 2.15 (s, 3H), 1.12 (t, 3H).

Example 16

(4-{(E)-3-[4-(2-Ethyl-5,7-dimethyl-pyrazolo[1,5-a]pyrimidin-3-ylmethyl)-phenyl]-allyl}-piperazin-1-yl)-((2S,3R)-3-hydroxy-pyrrolidin-2-yl)-methanone dihydrochloride

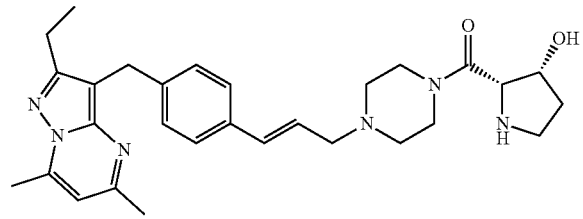 [SMILES: CCc1nn2c(C)cc(C)nc2c1Cc1ccc(/C=C/CN2CCN(C(=O)[C@H]3NCC[C@H]3O)CC2)cc1]

This compound was synthesized from example 14 analogously to example 7 step A using (2S,3R)-1-(tert-butoxycarbonyl)-3-hydroxypyrrolidine-2-carboxylic acid.

LC/MS: 1.49 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 503 [M+H]$^+$, $^1$H-NMR (DMSO-d6, 600 MHz) (ppm): 11.8 (br d, 1H), 10.3 (br d, 1H), 8.57 (brs, 1H), 7.38 (d, 2H), 7.21 (d, 2H), 6.79 (s, 1H), 6.78 (m, 1H), 6.36 (dt, 1H), 4.68 (m, 2H), 4.45 (m, 1H), 4.24 (m, 1H), 4.06 (s, 2H), 3.92 (m, 2H), 3.66 (m, 1H), 3.47 (m, 1H), 3.33 (m, 1H), 3.22 (m, 3H), 3.00 (m, 2H), 2.67 (q, 2H), 2.62 (s, 3H), 2.48 (s, 3H), 2.06 (m, 1H), 1.92 (m, 1H), 1.13 (t, 3H).

Reaction Scheme 15 (1):

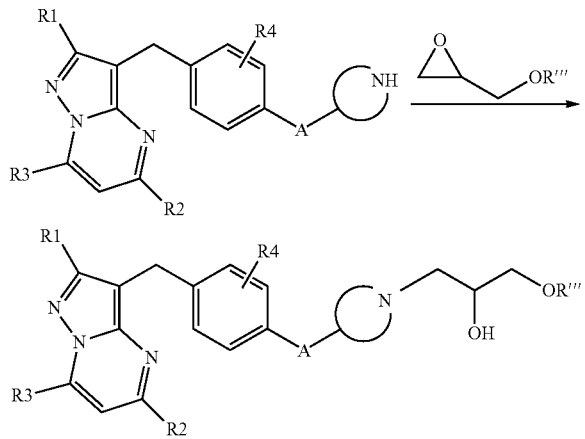

Reaction scheme 15(1) describes an alkylation reaction of the N-atom comprised in radical R of general formula (I) for example with an appropriately substituted oxirane derivative as shown above and as exemplified in the below example 17. R''' denotes an appropriate protecting group, for example a dialkyl silyl group.

Example 17

(R)-3-(4-{(E)-3-[4-(2-Ethyl-5,7-dimethyl-pyrazolo[1,5-a]pyrimidin-3-ylmethyl)-phenyl]-allyl}-piperazin-1-yl)-propane-1,2-diol dihydrochloride

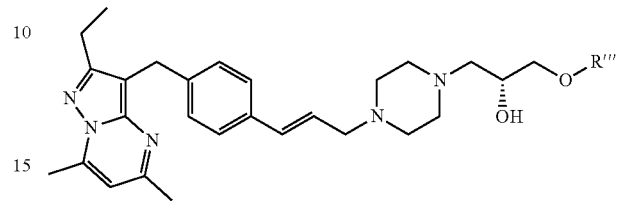

(1) Step A: (R)-1-(tert-butyl-dimethyl-silanyloxy)-3-(4-{(E)-3-[4-(2-ethyl-5,7-dimethyl-pyrazolo[1,5-]pyrimidin-3-ylmethyl)-phenyl]-allyl}-piperazin-1-yl)-propan-2-ol (R'''=TBDMS)

2-Ethyl-5,7-dimethyl-3-[4-((E)-3-piperazin-1-yl-propenyl)-benzyl]-pyrazolo[1,5-a]pyrimidine (example 14) (150 mg, 0.32 mmol) and (R)-tert-butyldimethyl(oxiran-2-ylmethoxy)silane (0.1 ml, 0.32 mmol) and K$_2$CO$_3$ (90 mg, 0.65 mmol) were dissolved in 0.9 ml of ethanol and stirred for 6 min at 120° C. in the microwave. The reaction mixture was concentrated under reduced pressure. The residue was purified via chromatography (silica gel, methanol/EtOAc (0-40%)) to give a yellow oil.

MS (ESI): 578 [M+H]$^+$, $^1$H-NMR (DMSO-d6, 600 MHz) δ (ppm): 7.29 (d, 2H), 7.12 (d, 2H), 6.75 (s, 1H), 6.44 (m, 1H), 6.18 (m, 1H), 4.32 (br, 1H), 4.02 (s, 2H), 3.59 (m, 1H), 3.49 (m, 2H), 3.02 (m, 2H), 2.67 (q, 2H), 2.63 (s, 3H), 2.49-2.5 (m, 8H), 2.48 (s, 3H), 2.35 (m, 1H), 2.20 (m, 1H), 1.13 (t, 3H), 0.85 (s, 9H), 0.03 (s, 6H).

(2) Step B: (R)-3-(4-{(E)-3-[4-(2-ethyl-5,7-dimethyl-pyrazolo[1,5-a]pyrimidin-3-ylmethyl)-phenyl]-allyl}-piperazin-1-yl)-propane-1,2-diol dihydrochloride (R'''=H)

(R)-1-(tert-Butyl-dimethyl-silanyloxy)-3-(4-{(E)-3-[4-(2-ethyl-5,7-dimethyl-pyrazolo[1,5-]pyrimidin-3-ylmethyl)-phenyl]-allyl}-piperazin-1-yl)-propan-2-ol (step A, R'''=TBDMS) (175 mg, 0.3 mmol) was dissolved in 2 ml of THF. 0.5M HCl in H$_2$O (3.6 ml, 1.8 mmol) was added and the reaction mixture was stirred for 1 h at rt. The reaction mixture was evaporated and dried on high vacuum to yield a yellow solid.

LC/MS: 0.73 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 464 [M+H]$^+$, $^1$H-NMR (DMSO-d6, 600 MHz) δ (ppm): 12.3 (br, 1H), 11.3 (br, 1H), 7.37 (d, 2H), 7.22 (d, 2H), 6.87 (m, 1H), 6.79 (s, 1H), 6.32 (m, 1H), 4.07 (s, 2H), 4.02 (m, 1H), 3.93 (m, 2H), 3.4-3.6 (m, 10H), 3.42 (m, 1H), 3.3 (m, 1H), 2.68 (q, 2H), 2.65 (s, 3H), 2.51 (s, 3H), 1.13 (t, 3H).

Reaction Scheme 16:

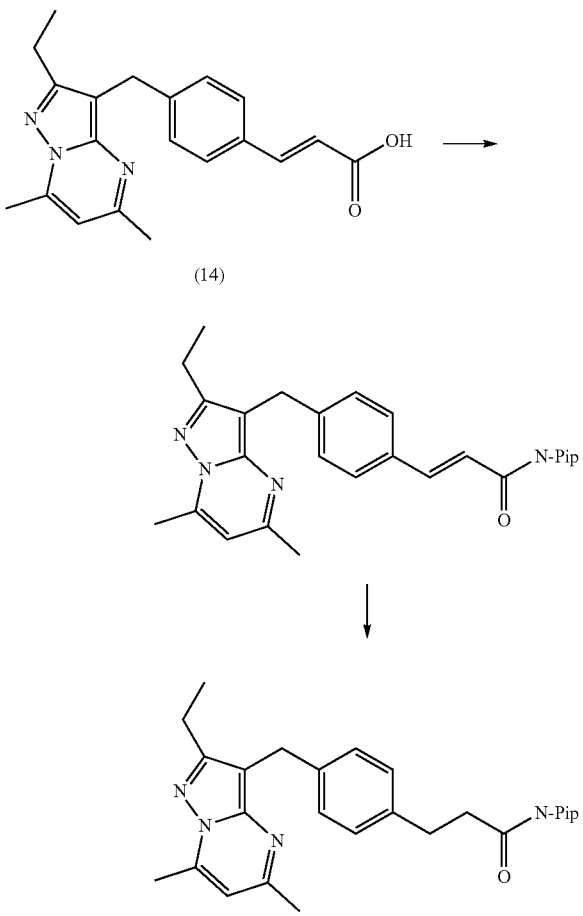

Reaction scheme 16 describes a "peptide" coupling reaction of the carboxylic acid substrate with an appropriate amine, such a for example with a piperidine derivative or a piperazine derivative. Accordingly, N-Pip may denote a Piperidine or a piperazine moiety wherein one H-atom is removed, which moiety may comprise an optional substitution.

Example 18

(E)-3-[4-(2-Ethyl-5,7-dimethyl-pyrazolo[1,5-a]pyrimidin-3-ylmethyl)-phenyl]-1-piperazin-1-yl-propenone hydrochloride

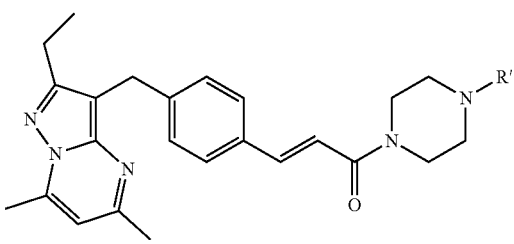

Step A: 4-{(E)-3-[4-(2-ethyl-5,7-dimethyl-pyrazolo[1,5-a]pyrimidin-3-ylmethyl)-phenyl]-acryloyl}-piperazine-1-carboxylic acid tert-butyl ester (R'=Boc)

EDC (0.575 g, 3 mmol) was added to a solution of (E)-3-[4-(2-Ethyl-5,7-dimethyl-pyrazolo[1,5-a]pyrimidin-3-ylmethyl)-phenyl]-acrylic acid (5) (671 mg, 2 mmol), Boc-piperazine (0.41 g, 2.2 mmol), HOBT (324 mg, 2.4 mmol) and Et$_3$N (0.36 ml, 2.6 mmol) were in 20 ml of CH$_2$Cl$_2$ and the reaction mixture was stirred at rt for 16 h. The mixture was quenched with saturated NaHCO$_3$ solution and extracted twice with CH$_2$Cl$_2$. The organic layer was washed with H$_2$O, dried over Na$_2$SO$_4$, filtered off and concentrated under reduced pressure. The crude product was purified by chromatography (silica gel, EtOAc/cyclohexane 50-100%) to give a yellow solid.

MS (ESI): 504 [M+H]$^+$, $^1$H-NMR (DMSO-d6, 400 MHz) δ (ppm): 7.59 (d, 2H), 7.44 (d, 1H), 7.23 (d, 2H), 7.17 (d, 1H), 6.78 (s, 1H), 4.03 (s, 2H), 3.68 (brs, 2H), 3.56 (brs, 2H), 3.37 (brs, 4H), 2.67 (q, 2H), 2.62 (s, 3H), 2.49 (s, 3H), 1.42 (s, 9H), 1.12 (t, 3H).

Step B: (E)-3-[4-(2-ethyl-5,7-dimethyl-pyrazolo[1,5-a]pyrimidin-3-ylmethyl)-phenyl]-1-piperazin-1-yl-propenone (R'=H)

This compound was synthesized from step A analogously to example 3 step B.
LC/MS: 1.51 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);
MS (ESI): 404 [M+H]$^+$, $^1$H-NMR (DMSO-d6, 400 MHz) δ (ppm): 9.38 (brs, 2H), 7.59 (d, 2H), 7.46 (d, 1H), 7.24 (d, 2H), 7.18 (d, 1H), 6.78 (s, 1H), 4.07 (s, 2H), 3.91 (brs, 2H), 3.78 (brs, 2H, 3.10 (brs, 4H), 2.68 (q, 2H), 2.64 (s, 3H), 2.49 (s, 3H), 1.13 (t, 3H).

Example 19

3-[4-(2-Ethyl-5,7-dimethyl-pyrazolo[1,5-a]pyrimidin-3-ylmethyl)-phenyl]-1-piperazin-1-yl-propan-1-one hydrochloride

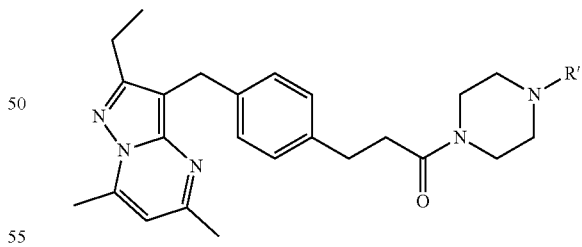

Step A: 4-{3-[4-(2-ethyl-5,7-dimethyl-pyrazolo[1,5-a]pyrimidin-3-ylmethyl)-phenyl]-propionyl}-piperazine-1-carboxylic acid tert-butyl ester (R'=Boc)

4-{(E)-3-[4-(2-Ethyl-5,7-dimethyl-pyrazolo[1,5-a]pyrimidin-3-ylmethyl)-phenyl]-acryloyl}-piperazine-1-carboxylic acid tert-butyl ester (example 18 step A) (0.353 g, 0.7 mmol) was dissolved in CH$_3$OH. Pd(OH)$_2$ (35.3 mg, 0.7 mmol) was added under argon and the mixture was hydrogenated for 1 h at rt. Then the reaction mixture was filtrated over celite and evaporated under reduced pressure. The crude product was purified by chromatography (silica gel, $CH_2Cl_2/CH_3OH/NH_3$ 0 95:4.5:0.5) to give an yellow oil.

MS (ESI): 506 [M+H]$^+$, $^1$H-NMR (DMSO-d6, 400 MHz) δ (ppm): 7.08 (s, 4H), 6.74 (s, 1H), 3.98 (s, 2H), 3.39 (m, 2H), 3.34 (m, 2H), 3.22 (brs, 4H), 2.73 (t, 2H), 2.66 (q, 2H), 2.62 (s, 3H), 2.55 (t, 2H), 2.47 (s, 3H), 1.39 (s, 9H), 1.13 (t, 3H).

Step B: 3-[4-(2-ethyl-5,7-dimethyl-pyrazolo[1,5-a]pyrimidin-3-ylmethyl)-phenyl]-1-piperazin-1-yl-propan-1-one (R'=H)

This compound was synthesized from step A analogously to example 3 step B.

LC/MS: 1.51 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 406 [M+H]$^+$, $^1$H-NMR (DMSO-d6, 400 MHz) δ (ppm): 9.07 (brs, 2H), 7.09 (s, 4H), 6.75 (s, 1H), 3.99 (s, 2H), 3.63 (brs, 4H), 3.02 (brs, 4H), 2.73 (t, 2H), 2.67 (q, 2H), 2.62 (s, 3H), 2.60 (t, 2H), 2.48 (s, 3H), 1.14 (t, 3 H).

Reaction Scheme 17:

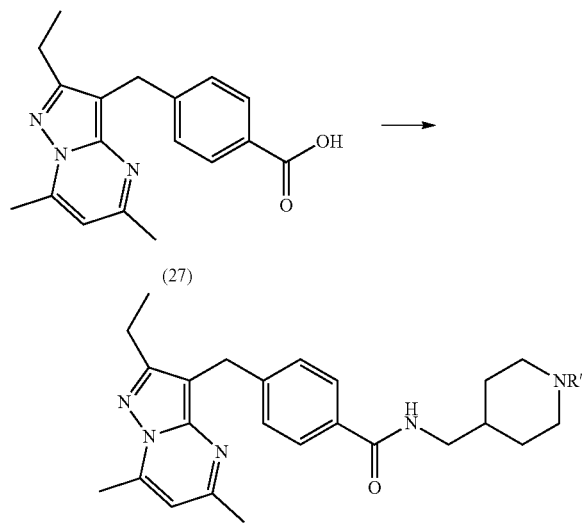

(27)

Reaction scheme 17 describes an amide coupling reaction of the carboxylic acid substrate (27) with an appropriate amine, such a for example with an aminomethyl piperidine derivative, optionally substituted by a group R' . . . .

Example 20

4-(2-Ethyl-5,7-dimethyl-pyrazolo[1,5-a]pyrimidin-3-ylmethyl)-N-piperidin-4-ylmethyl-benzamide

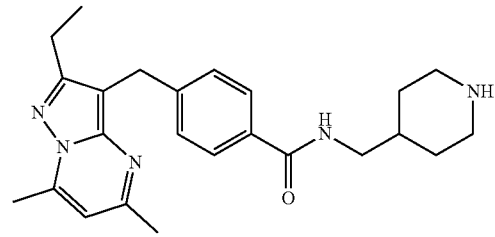 [SMILES: CCc1nn2c(C)cc(C)nc2c1Cc1ccc(C(=O)NCC2CCNCC2)cc1]

This compound was synthesized from step A analogously to example 18 from 4-((2-ethyl-5,7-dimethylpyrazolo[1,5-a]pyrimidin-3-yl)methyl)benzoic acid (27) and 1-Boc-4-(aminomethyl)piperidine followed by Boc-deprotection analogously to example 3 step B.

LC/MS: 1.63 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 406 [M+H]$^+$, $^1$H-NMR (DMSO-d6, 400 MHz) δ (ppm): 8.97 (brs, 1H), 8.69 (brs, 1H), 8.50 (t, 1H), 7.74 (d, 2H), 7.26 (d, 2H), 6.79 (s, 1H), 4.10 (s, 2H), 3.22 (m, 2H), 3.15 (dd, 2H), 2.73-2.88 (m, 2H), 2.67 (q, 2H), 2.65 (s, 3H), 2.51 (s, 3H), 1.70-1.89 (m, 3H), 1.37 (m, 2H), 1.13 (t, 3H).

Reaction Scheme 18:

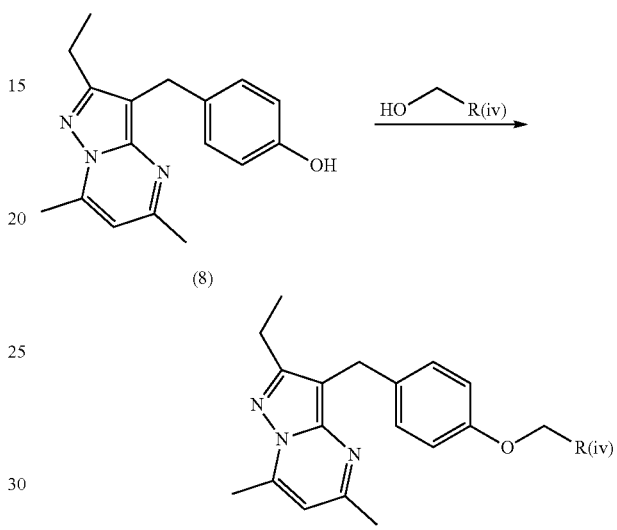

(8)

Reaction scheme 18 describes the alkylation of the phenol substrate 8 with an appropriately substituted hydroxy methylene derivate, in which R(iv) denotes a 4-piperidinyl- or a cyclohexyl-radical, each of which may be optionally substituted as shown in the following examples.

Example 21

2-Ethyl-5,7-dimethyl-3-[4-(piperidin-4-ylmethoxy)-benzyl]-pyrazolo[1,5-a]pyrimidine hydrochloride (R'=H)

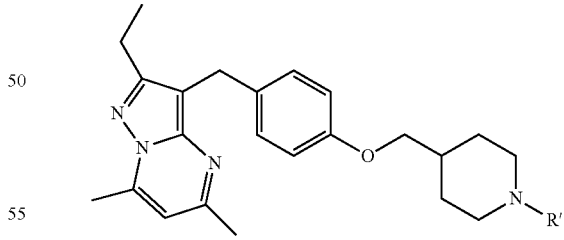

4-(2-Ethyl-5,7-dimethyl-pyrazolo[1,5-a]pyrimidin-3-yl-methyl)-phenol (8), (0.12 g, 0.4 mmol) N-Boc-4-piperidin-methanol (0.11 g, 0.49 mmol) were dissolved in 3 ml of dichloromethane and triphenylphosphine (0.13 g, 0.49 mmol) and DIAD (0.12 g, 0.49 mmol) were added. The reaction mixture was stirred at rt for 12 h. It was then diluted with ethylacetate and the organic layer was washed with 5% aqueous NaHCO$_3$ solution. The organic layer was washed again with brine and dried over Na$_2$SO$_4$. It was then concentrated under reduced pressure and the crude product purified by chromatography to give the title compound as a white solid. Boc deprotection was performed analogously to example 3 step B.

LC/MS: 1.95 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 378 [M+H]$^+$, $^1$H-NMR (DMSO-d6, 500 MHz) δ (ppm): 8.87 (br, 1H), 8.55 (br, 1H), 7.08 (d, 2H), 6.80 (d, 2H), 6.75 (s, 1H), 3.96 (s, 2H), 3.78 (d, 2H), 3.25 (m, 2H), 2.85 (m, 2H), 2.66 (q, 2H), 2.62 (s, 3H), 2.48 (s, 3H), 2.0 (m, 1H), 1.86 (m, 2H), 1.45 (m, 2H), 1.12 (t, 3H).

Example 22

{4-[4-(2-Ethyl-5,7-dimethyl-pyrazolo[1,5-a]pyrimidin-3-ylmethyl)-phenoxymethyl]-piperidin-1-yl}-((2S,3R)-3-hydroxy-pyrrolidin-2-yl)-methanone

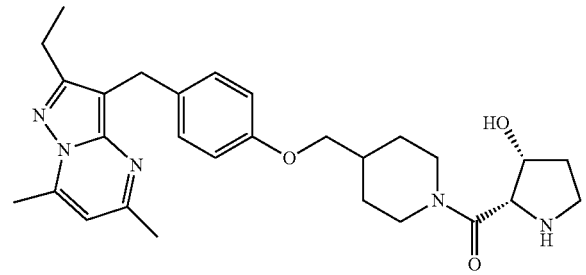 [SMILES: CCc1nn2c(C)cc(C)nc2c1Cc1ccc(OCC2CCN(C(=O)[C@H]3NCC[C@H]3O)CC2)cc1]

This compound was synthesized analogously to example 21 using Boc-cis-3-hydroxy-L-proline followed by Boc-deprotection analogously to example 3 step B.

LC/MS: 2.07 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 492 [M+H]$^+$, $^1$H-NMR (DMSO-d6, 500 MHz) δ (ppm): 8.5 (bs, 1H, NH), 7.09 (d, 2H), 6.81 (d, 2H), 6.7 (s, 1H), 4.65-4.59 (m, 3H), 4.50 (dd, 1H), 3.98 (s, 2H), 3.79 (d, 2H), 3.36-3.33 (m, 1H), 3.21-3.17 (m, 1H), 3.14 (dd, 1H), 2.67 (q, 2H), 2.64 (s, 3H), 2.34-2.30 (m, 1H), 2.08.2.02 (m, 1H), 1.95-1.91 (m, 1H), 1.83-1.79 (m, 3H), 1.13 (t, 3H).

Example 23

4-[4-(2-Ethyl-5,7-dimethyl-pyrazolo[1,5-a]pyrimidin-3-ylmethyl)-phenoxymethyl]-cyclohexylamine

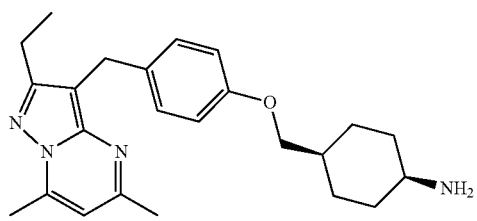 [SMILES: CCc1nn2c(C)cc(C)nc2c1Cc1ccc(OC[C@H]2CC[C@@H](N)CC2)cc1]

This compound was synthesized analogously to example 21 using tert-butyl (1S,4S)-4-(hydroxymethyl)cyclohexylcarbamate followed by Boc-deprotection analogously to example 3 step B.

LC/MS: 0.85 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 394.4 [M+H]$^+$, $^1$H-NMR (MeOH-d4, 500 MHz) δ (ppm): 1.20 (t, 3 H) 1.63-1.89 (m, 8 H) 1.98-2.10 (m, 1 H) 2.68-2.79 (m, 5 H) 2.90 (s, 3 H) 3.91 (d, 2H) 4.16 (s, 2 H) 6.86 (m, 2 H) 7.03 (s, 1 H) 7.10 (m, 2 H).

Example 24

(2S,3R)-3-Hydroxy-pyrrolidine-2-carboxylic acid {4-[4-(2-ethyl-5,7-dimethyl-pyrazolo[1,5-a]pyrimidin-3-ylmethyl)-phenoxymethyl]-cyclohexyl}-amide

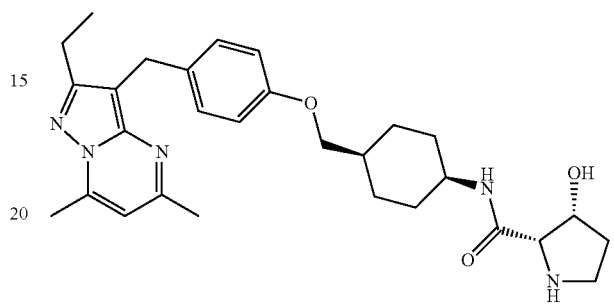

This compound was synthesized analogously to example 7 using (2S,3R)-1-(tert-butoxycarbonyl)-3-hydroxypyrrolidine-2-carboxylic acid followed by Boc-deprotection analogously to example 3 step B.

LC/MS: 0.88 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 507 [M+H]$^+$, $^1$H-NMR (MeOD, 500 MHz) δ (ppm): 6.89-7.03 (m, 3H), 6.73 (d, 2H), 4.63 (d, 1H), 4.12 (d, 1H), 4.05 (s, 2H), 3.92 (br. s, 1H), 3.74 (d, 2H), 3.56 (s, 1H), 3.37-3.50 (m, 1H), ) 3.32 (d, 1H), 2.80 (s, 3H), 2.60-2.68 (m, 5H), 2.06-2.19 (m, 1H), 2.01 (d, 1H), 2.01 (d, 1H), 1.82 (d, J=4.80 Hz, 1 H), 1.54-1.70 (m, 5 H), 1.46 (dd, 2 H), 1.08 (t, 3 H).

Example 25

4-{2-[4-(2-Ethyl-5,7-dimethyl-pyrazolo[1,5-a]pyrimidin-3-ylmethyl)-phenoxy]-ethyl}-piperidin-4-ol

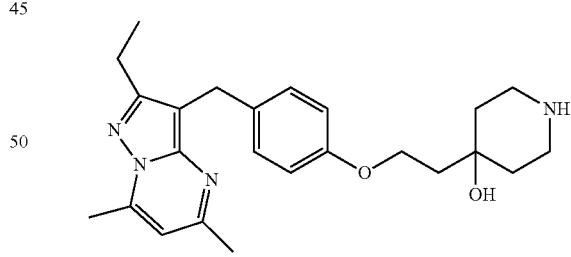

This compound was synthesized analogously to example 21 using 4-hydroxy-4-(2-hydroxy-ethyl)-piperidine-1-carboxylic acid tert-butyl ester (41) followed by Boc-deprotection analogously to example 3 step B.

LC/MS: 1.83 min (2.1×50 mm, HSS T3 1.8 um at 50° C., 1.2 ml/min, gradient 2-98% acetonitrile (+0.04% formic acid) in water (+0.05% formic acid+3.75 mM NH$_4$OAc);

MS (ESI): 409 [M+H]$^+$, $^1$H-NMR (DMSO-d6, 400 MHz) δ (ppm): 8.61 (brs, 1H), 8.39 (brs, 1H) 7.08 (d, 2H), 6.79 (d, 2H), 6.75 (s, 1H), 4.04 (t, 2H), 3.96 (s, 2H), 3.07 (m, 4H), 2.66 (q, 2H), 2.62 (s, 3H), 2.48 (s, 3H), 1.84 (t, 3H), 1.60-1.77 (m, 4H), 1.13 (t, 3H).

Reaction Scheme 19:

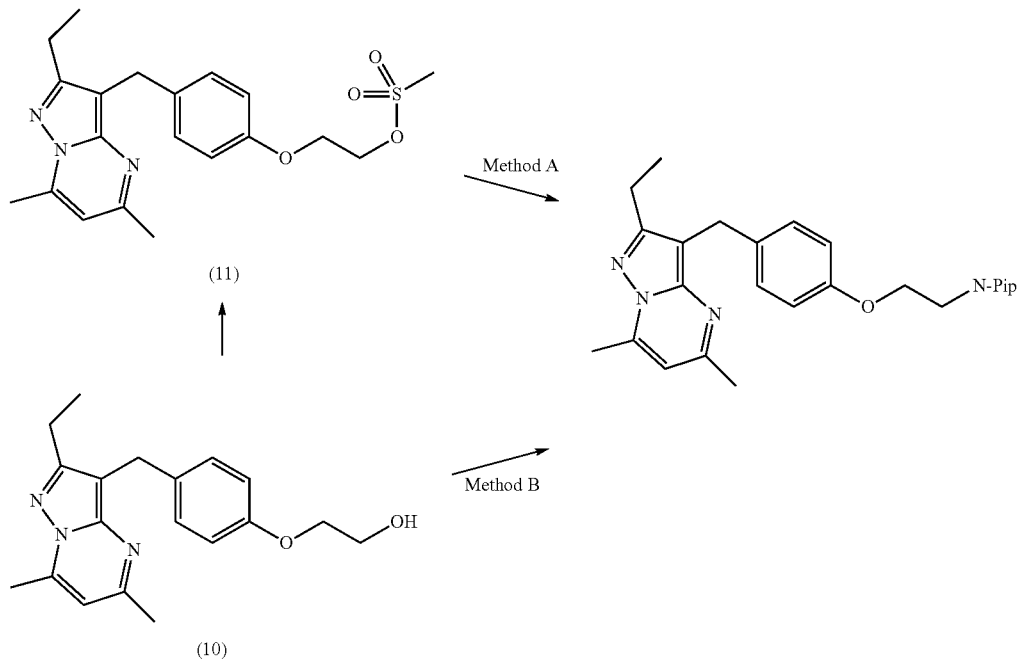

N-Pip may denote a piperazine or a Piperidine moiety

Example 26

2-Ethyl-5,7-dimethyl-3-[4-(2-piperazin-1-yl-ethoxy)-benzyl]-pyrazolo[1,5-a]pyrimidine (Method A)

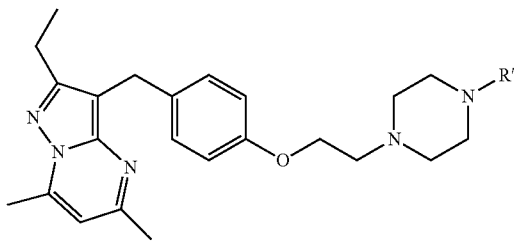

(1) Step A: 4-{2-[4-(2-ethyl-5,7-dimethyl-pyrazolo[1,5-a]pyrimidin-3-ylmethyl)-phenoxy]-ethyl}-piperazine-1-carboxylic acid tert-butyl ester (R'=Boc)

A mixture of 2-(4-((2-ethyl-5,7-dimethylpyrazolo[1,5-a]pyrimidin-3-yl)methyl)phenoxy)ethyl methanesulfonate (11) (90 mg, 0.223 mmol), tert-butyl piperazine-1-carboxylate (41.5 mg, 0.223 mmol) and $K_2CO_3$ (92 mg, 0.669 mmol) in dry DMF (4 ml) was heated at 80° C. for 3 hours. After cooling to rt, ethyl acetate was added and the mixture was extracted with water and washed with NaCl-solution. After drying ($Na_2SO_4$) and evaporation of solvents, the residue was purified by reverse phase chromatography ($H_2O$—$CH_3CN$ gradient) to afford the title product.

MS (ESI): 494 [M+H]$^+$, $^1$H-NMR (CDCl$_3$, 400 MHz) δ (ppm): 7.15 (d, 2H), 6.77 (d, 2H), 6.45 (s, 1H), 4.14 (m, 2H), 4.08 (s, 2H), 3.52 (m, 4H), 2.87 (m, 2H), 2.73 (q, 2H), 2.70 (s, 3H), 2.55 (s, 3H), 1.58 (m, 4H), 1.46 (s, 9H), 1.20 (t, 3H).

(2) Step B: 2-ethyl-5,7-dimethyl-3-[4-(2-piperazin-1-yl-ethoxy)-benzyl]-pyrazolo[1,5-a]pyrimidine (R'=H)

This compound was synthesized from step A analogously to example 3 step B.

LC/MS: 1.75 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 394 [M+H]$^+$, $^1$H-NMR (DMSO-d6, 400 MHz) δ (ppm): 11.76 (brs, 1H), 9.52 (brs, 2H), 7.13 (d, 2H), 6.88 (d, 2H), 6.75 (s, 1H), 4.33 (t, 2H), 3.98 (s, 2H), 3.57 (m, 10H), 2.66 (q, 2H), 2.62 (s, 3H), 2.48 (s, 3H), 1.13 (t, 3H).

Example 27

2-Ethyl-3-{4-[2-((R)-3-methoxymethyl-piperazin-1-yl)-ethoxy]-benzyl}-5,7-dimethyl-pyrazolo[1,5-a]pyrimidine (Method B)

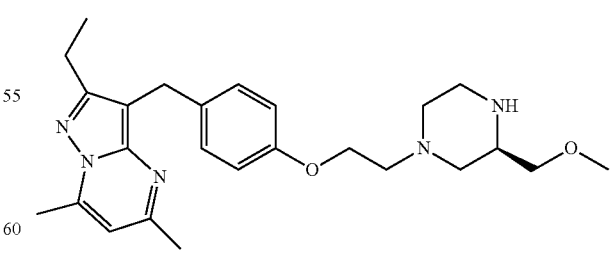

This compound was synthesized from step A analogously to example 9 (which is an alkylation reaction using Zaragoza reagent) using 2-[4-(2-Ethyl-5,7-dimethyl-pyrazolo[1,5-a]pyrimidin-3-ylmethyl)-phenoxy]-ethanol (intermediate (10) described above in reaction scheme 3) and (R)-tert-butyl 2-(methoxymethyl)piperazine-1-carboxylate followed by Boc-deprotection analogously to example 3 step B.

LC/MS: 1.63 min (2.1×50 mm, HSS T3 1.7 um at 50° C., 1.2 ml/min, gradient 2-98% acetonitrile (+0.04% formic acid) in water (+0.05% formic acid+3.75 mM NH₄OAc);

MS (ESI): 438 [M+H]⁺, ¹H-NMR (DMSO-d6, 600 MHz) δ (ppm): 10.0-10.3 (br, 1H), 7.13 (d, 2H), 6.90 (d, 2H), 6.78 (s, 1H), 4.37 (m, 2H), 4.01 (s, 2H), 3.95 (m, 1H), 3.80 (m, 2H), 3.66 (m, 2H), 3.59 (m, 4H), 3.50 (m, 2H), 3.33 (s, 3H), 2.68 (q, 2H), 2.64 (s, 3H), 2.51 (s, 3H), 1.14 (t, 3H).

Reaction Scheme 20:

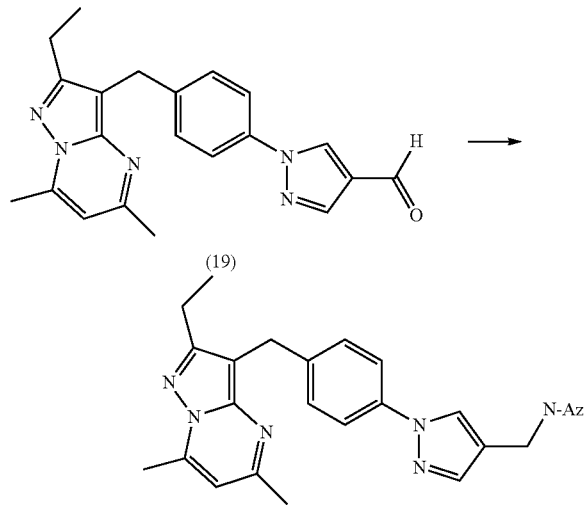

Reaction scheme 20 describes a reductive amination procedure in analogy to reaction scheme 14 (Method A).

N-Az denotes an azetidine moiety optionally substituted by OH, NH₂, and the like; and N-Az may also be N-Pip and hence may denote a Piperidine or a piperazine moiety optionally substituted by amino, hydroxymethyl and the like.

Example 28

1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ol

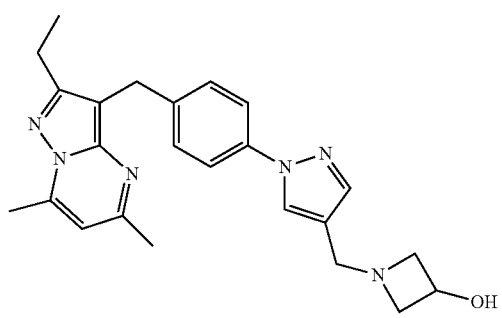 [SMILES: CCc1nn2c(C)cc(C)nc2c1Cc1ccc(-n2cc(CN3CC(O)C3)cn2)cc1]

This compound was synthesized from step A analogously to example 9 step A using 1-[4-(2-Ethyl-5,7-dimethyl-pyrazolo[1,5-a]pyrimidin-3-ylmethyl)-phenyl]-3-methyl-1H-pyrazole-4-carbaldehyde (19) and azetidin-3-ol.

LC/MS: 0.78 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 417 [M+H]⁺, ¹H-NMR (CDCL₃, 400 MHz) δ (ppm): 7.79 (s, 1H), 7.60 (s, 1H), 7.53 (d, 2H), 7.30 (d, 2H), 6.49 (s, 1H), 4.46 (q, 1H), 4.18 (s, 2H), 3.66 (dd, 2H), 3.58 (s, 2H), 2.92-2.99 (m, 2H), 2.71-2.79 (m, 6H), 2.57 (s, 3H), 1.22 (t, 3H).

Example 29

1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ylamine

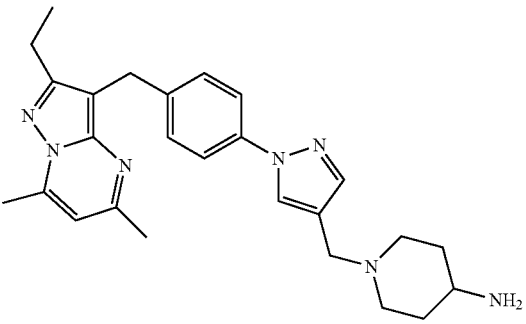 [SMILES: CCc1nn2c(C)cc(C)nc2c1Cc1ccc(-n2cc(CN3CCC(N)CC3)cn2)cc1]

This compound was synthesized from step A analogously to example 9 step A using 1-[4-(2-Ethyl-5,7-dimethyl-pyrazolo[1,5-a]pyrimidin-3-ylmethyl)-phenyl]-3-methyl-1H-pyrazole-4-carbaldehyde (19) and tert-butyl azetidin-3-ylcarbamate followed by Boc-deprotection analogously to example 3 step B.

LC/MS: 0.78 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 416 [M+H]⁺, ¹H-NMR (MeOD, 500 MHz) δ (ppm): 8.46-8.51 (m, 1H), 7.86-7.92 (m, 1H), 7.63-7.71 (m, 2H), 7.36 (d, 2H), 6.90 (s, 1H), 4.57 (br s, 1H), 4.44-4.53 (m, 3 H), 4.31-4.44 (m, 1 H), 4.25 (s, 2H), 2.73-2.85 (m, 5 H), 2.66 (s, 3 H), 1.21 (t, 3H).

Example 30

1-{1-[4-(2-Ethyl-5,7-dimethyl-pyrazolo[1,5-a]pyrimidin-3-ylmethyl)-phenyl]-1H-pyrazol-4-ylmethyl}-piperidin-4-ylamine This compound was synthesized from step A analogously to example 9 step A using 1-[4-(2-Ethyl-5,7-dimethyl-pyrazolo[1,5-a]pyrimidin-3-ylmethyl)-phenyl]-3-methyl-1H- pyrazole-4-carbaldehyde (19) and piperidin-4-yl-carbamic acid tert-butyl ester followed by Boc-deprotection analogously to example 3 step B.

LC/MS: 0.59 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 444 [M+H]$^+$, $^1$H-NMR (400 MHz, MeOD) δ (ppm): 8.52 (s, 1H), 7.90 (s, 1H), 7.71 (m, 2H), 7.36 (m, 2H), 7.03 (s, 1, H), 4.37 (s, 2H), 4.29 (s, 2H), 3.63-3.74 (m, 2H), 3.50 (d, 1H), 3.17 (t, 2H), 2.89 (s, 3H), 2.71-2.82 (m, 5H), 2.30 (d, 2H), 2.06 (t, 2H), 1.22 (t, 3H).

Example 31

2-Ethyl-5,7-dimethyl-3-[4-(4-piperazin-1-ylmethyl-pyrazol-1-yl)-benzyl]-pyrazolo[1,5-a]pyrimidine

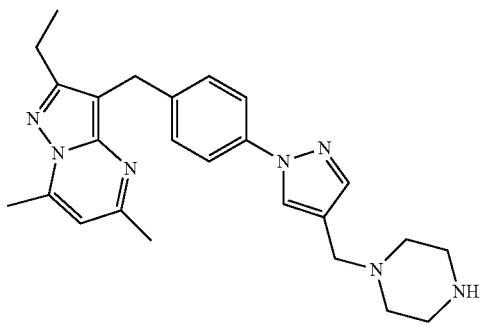 [SMILES: CCc1nn2c(C)cc(C)nc2c1Cc1ccc(-n2cc(CN3CCNCC3)nn2)cc1]

This compound was synthesized from step A analogously to example 9 step A using 1-[4-(2-Ethyl-5,7-dimethyl-pyrazolo[1,5-a]pyrimidin-3-ylmethyl)-phenyl]-3-methyl-1H-pyrazole-4-carbaldehyde (19) and tert-butyl piperazine-1-carboxylate followed by Boc-deprotection analogously to example 3 step B.

LC/MS: 0.73 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 430 [M+H]$^+$, $^1$H-NMR (CDCl$_3$, 500 MHz) δ (ppm): 7.85 (br. s., 1 H), 7.62 (s, 1 H), 7.53 (m, 2H), 7.32 (m, 2H), 6.49 (s, 1H), 4.19 (s, 2H), 3.60 (br. s., 2H), 3.27 (br s, 4H), 2.86 (br s, 3H), 2.70-2.78 (m, 5H), 2.57 (s, 3 H), 1.22 (t, 3H).

Example 32

((R)-4-{1-[4-(2-Ethyl-5,7-dimethyl-pyrazolo[1,5-a]pyrimidin-3-ylmethyl)-phenyl]-1H-pyrazol-4-ylmethyl}-piperazin-2-yl)-methanol

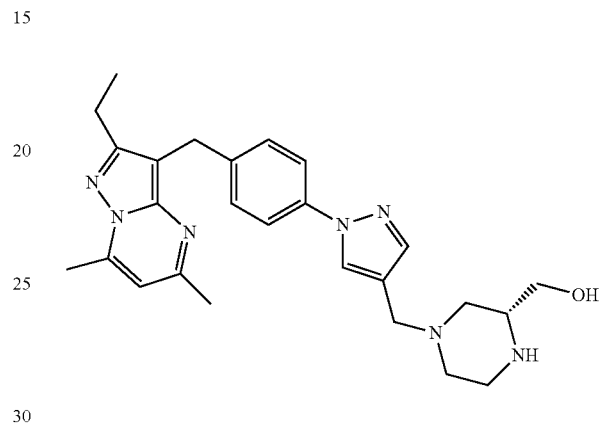

This compound was synthesized from step A analogously to example 8 step A using 1-[4-(2-Ethyl-5,7-dimethyl-pyrazolo[1,5-a]pyrimidin-3-ylmethyl)-phenyl]-3-methyl-1H-pyrazole-4-carbaldehyde (19) and (R)-tert-butyl 2-(hydroxymethyl)piperazine-1-carboxylate.

LC/MS: 1.60 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 460 [M+H]$^+$, $^1$H-NMR (DMSO-d6, 500 MHz) δ (ppm): 8.26 (s, 1H), 7.68 (d, 2H), 7.58 (s, 1H), 7.27 (d, 2H), 6.75 (s, 1H), 5.76 (s, 2H), 4.51 (br, 1H), 4.07 (s, 2H), 3.38 (m, 2H), 3.25 (m, 2H), 3.24 (m, 1H), 2.74 (m, 1H), 2.71 (m, 1H), 2.69 (q, 2H), 2.64 (s, 3H), 2.51 (m, 1H), 2.49 (s, 3H), 1.91 (m, 1H), 1.59 (m, 1H), 1.14 (t, 3H).

Reaction Scheme 21:

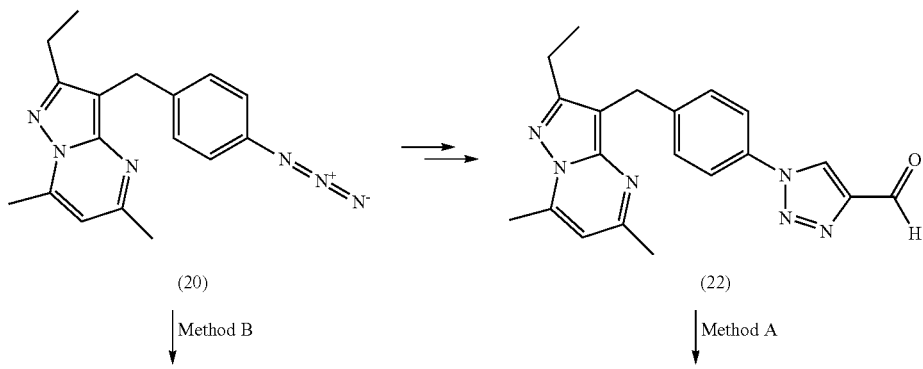

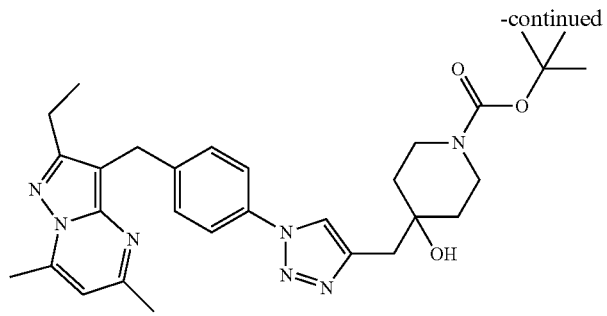

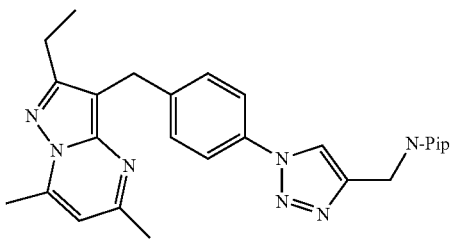

Reaction scheme 21 describes the synthesis of those compounds of the invention which carry a triazolo-methylene linker "A". The azide intermediate (20) is described in reaction scheme 5. Reaction scheme 5 also describes the conversion of intermediate into intermediate 22. The above intermediate (20) may be used for synthesizing compounds of the invention with a triazolo-methylene linker "A" and different "R" groups, for example 1-piperidinyl- or 4-piperidinyl groups.

N-Pip may denote a Piperidine or a piperazine moiety, e.g. as shown in example 33

Example 33

2-Ethyl-5,7-dimethyl-3-[4-(4-piperazin-1-ylmethyl-[1,2,3]triazol-1-yl)-benzyl]-pyrazolo[1,5-a]pyrimidine (Method A)

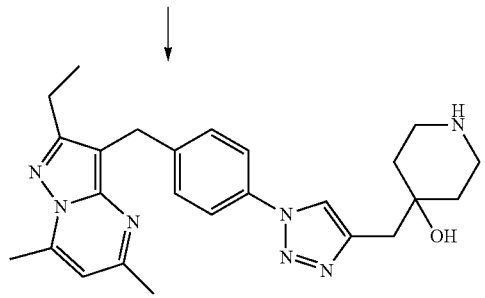

A solution of aldehyde 22 (100 mg, 0.28 mmol) and piperazine (47.8 mg, 0.56 mmol) in 6 ml of MeOH/AcOH (98:2) was stirred at r.t. for 30 min. NaCNBH$_3$ (26.2 mg, 0.416 mmol) was added and the reaction mixture was stirred at r.t. for 1 hr. The reaction was diluted with EtOAc and washed with sat aq NaHCO$_3$ and brine. The organic layer was dried over anhydrous Na$_2$SO$_4$, filtered and concentrated under HV. The crude product was purified by preparative HPLC (water/acetonitril (0.1% TFA)) to yield a white solid.

LC/MS: 0.70 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI) 431 [M+H]$^+$, $^1$H-NMR (360 MHz, MeOD) δ (ppm): 8.47 (s, 1H), 7.74 (d, 2H), 7.44 (d, 2H), 6.78 (s, 1H), 4.26 (s, 2H), 3.89 (s, 2H), 3.24-3.31 (m, 4H), 2.76-2.88 (m, 6H), 2.75 (s, 3H), 2.59 (s, 3H), 1.22 (t, 3H).

Example 34

4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol (Method B) (R'=H)

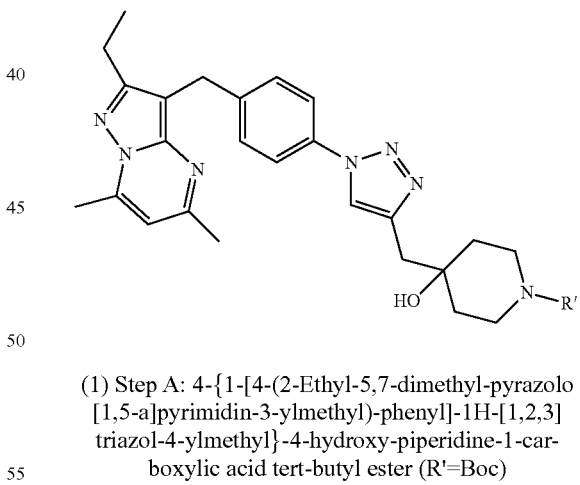

(1) Step A: 4-{1-[4-(2-Ethyl-5,7-dimethyl-pyrazolo[1,5-a]pyrimidin-3-ylmethyl)-phenyl]-1H-[1,2,3]triazol-4-ylmethyl}-4-hydroxy-piperidine-1-carboxylic acid tert-butyl ester (R'=Boc)

3-(4-Azido-benzyl)-2-ethyl-5,7-dimethyl-pyrazolo[1,5-a]pyrimidine (20) (0.25 g, 0.81 mmol) and 4-hydroxy-4-prop-2-ynyl-piperidine-1-carboxylic acid tert-butyl ester (43) (0.29 g, 1.22 mmol) were dissolved in 2 ml of acetonitrile. Copper (I) iodide (0.186 g, 0.97 mmol) was added. The reaction mixture was stirred for 2 h at 50° C. It was allowed to cool down to rt and concentrated. The residue was redissolved in dichloromethane and washed with brine. The organic layer was separated, dried and concentrated. The remaining crude material was purified by flash chromatography on silica gel to give the title compound as a yellow foam.

MS (ESI): 546 [M+H]+, 1H-NMR (CDCl3, 500 MHz) δ (ppm): 1.21-1.25 (m, 3 H) 1.47 (s, 9 H) 1.61 (d, J=12.13 Hz, 4H) 2.58 (s, 3 H) 2.71-2.80 (m, 5 H) 2.94 (s, 2 H) 3.23 (t, J=9.22 Hz, 3 H) 3.83 (d, J=10.11 Hz, 2 H) 4.23 (s, 2 H) 6.51 (s, 1 H) 7.40 (m, J=8.34 Hz, 2 H) 7.60 (m, J=8.34 Hz, 2 H) 7.77 (s, 1 H).

(2) Step B: 4-{1-[4-(2-ethyl-5,7-dimethyl-pyrazolo[1,5-a]pyrimidin-3-ylmethyl)-phenyl]-1H-[1,2,3]triazol-4-ylmethyl}-piperidin-4-ol (R'=H)

4-{1-[4-(2-Ethyl-5,7-dimethyl-pyrazolo[1,5-a]pyrimidin-3-ylmethyl)-phenyl]-1H-[1,2,3]triazol-4-ylmethyl}-4-hydroxy-piperidine-1-carboxylic acid tert-butyl ester (step A) was submitted to conditions described in example 3 step B for Boc deprotection.

LC/MS: 0.70 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 446 [M+H]+, 1H-NMR (CDCl3, 500 MHz) δ (ppm): 7.79 (s, 1H), 7.60 (m, 2H), 7.40 (m, 2H), 6.51 (s, 1H), 4.22 (s, 2H), 3.00-3.08 (m, 2H), 2.96 (s, 2H), 2.89 (d, 2H), 2.71-2.79 (m, 5H), 2.58 (s, 3H), 1.63 (br s, 4H), 1.24 (t, 3H).

Reaction Scheme 22:

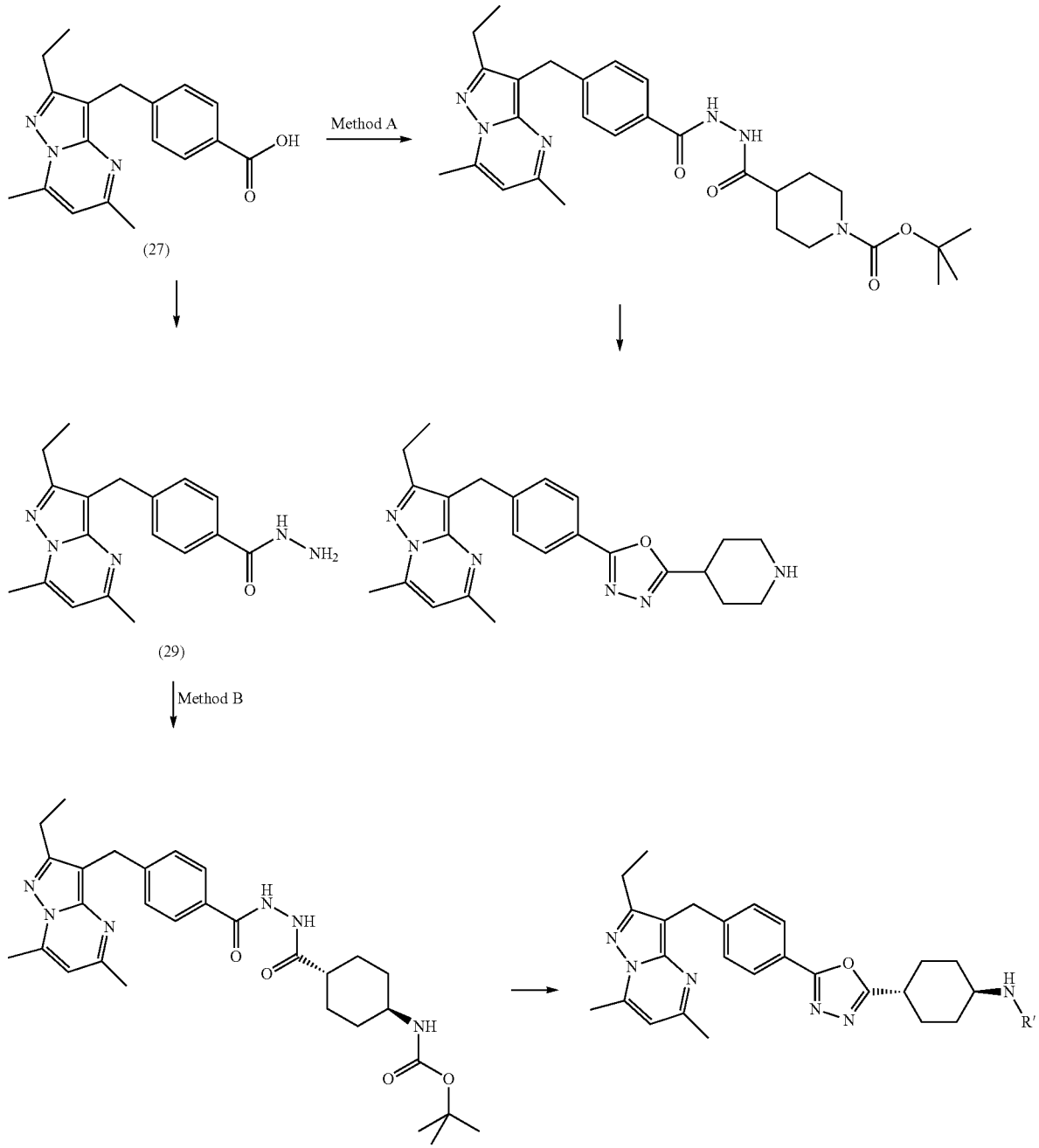

Reaction scheme 22 describes two alternative routes (method A and method B) by which compounds of the invention may be prepared that carry a central oxadiazole linker "A". In both methods, the oxadiazole linker may be obtained by reacting the hydrazone derivatives with an appropriate dehydration reaction, e.g. tosylchloride in the presence of a base, to yield the desired oxadiazole.

Example 35

2-Ethyl-5,7-dimethyl-3-[4-(5-piperidin-4-yl-[,3,4]oxadiazol-2-yl)-benzyl]-pyrazolo[1,5-a]pyrimidine (Method A)

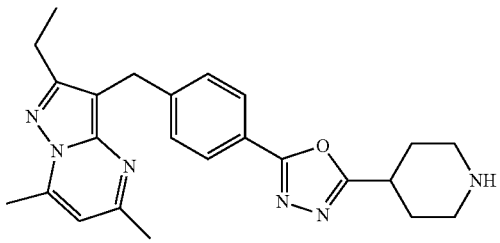 [SMILES: CCc1nn2c(C)cc(C)nc2c1Cc1ccc(-c2nnc(C3CCNCC3)o2)cc1]

(1) Step A: 4-{N'-[4-(2-ethyl-5,7-dimethyl-pyrazolo[1,5-a]pyrimidin-3-ylmethyl)-benzoyl]-hydrazinocarbonyl}-piperidine-1-carboxylic acid tert-butyl ester A 500 ml four-necked flask equipped with an overhead stirrer and a thermocouple was charged with acid 27 (10.0 g, 32.3 mmol, 1.0 eq), 120 ml of DMF and 2,4,6 trimethylpyridine (11.75 g, 96.9 mmol) under nitrogen purge. After stirring the reaction mixture for 30 min at 23° C., 4-hydrazinocarbonyl-piperidine-1-carboxylic acid tert-butyl ester (9.4 g, 38.7 mmol, 1.2 eq), EDC (12.3 g, 64.3 mmol), HOBT (1.48 g, 9.6 mmol) were added. The reaction mixture was stirred for 12 h at 23° C. After completion of the reaction, it was diluted with i-PrOAc/heptane (100 mL, 1:1) and followed by water (250 ml) at 23° C. The suspension was stirred for 1 h at 23° C. The solid was collected by filtration and washed with 50 ml of water. The wet product was dried at 40° C. for 12 h to obtain a white solid.

MS (ESI): 446 [M+H]+, 1H NMR (500 MHz, CDCl3) δ (ppm): 7.89 (d, 2 H), 7.36 (d, 2 H), 4.20 (s, 2 H), 4.06-4.15 (m, 2H), 3.07-3.17 (m, 2 H), 2.97 (d, 2 H), 2.68-2.77 (m, 5 H), 2.55 (s, 3 H), 2.09 (dd, 2 H), 1.81-1.92 (m, 2 H), 1.47 (s, 9 H), 1.39-1.44 (m, 1 H), 1.20 (t, 3 H).

(2) Step B: 2-ethyl-5,7-dimethyl-3-[4-(5-piperidin-4-yl-[1,3,4]oxadiazol-2-yl)-benzyl]-pyrazolo[1,5-a]pyrimidine A 500 ml four-necked flask equipped with an overhead stirrer, a thermocouple, and an addition funnel was charged with 4-{N'-[4-(2-Ethyl-5,7-dimethyl-pyrazolo[1,5-a]pyrimidin-3-ylmethyl)-benzoyl]-hydrazinocarbonyl}-piperidine-1-carboxylic acid tert-butyl ester (step A) (10.0 g, 18.7 mmol), TsCl (3.92 g, 20.5 mmol) and 150 ml of CH2Cl2. Triethyl amine (2.83 g 28.0 mol) was added over 10 min, maintaining the batch temperature below r.t. and the mixture was stirred for 12 h at 23° C. Then TFA (10.6 g, 93.6 mmol) was added and stirring was continued for an additional 6 h at r.t. After completion of the reaction, solvent was evaporated under reduced pressure until a final volume of ~30 mL was reached. 100 ml of ethyl acetate was added and the mixture was evaporated under reduced pressure. This procedure was repeated one more time to ensure all CH2Cl2 is removed. 150 ml of ethyl acetate was added and cooled to 0° C. 6 N NaOH (100 ml) solution was added to the reaction over a period of 30 min while maintaining the batch temperature at 0° C. Then the mixture was stirred at 0° C. for 30 min. The organic layer was separated and washed with 6 N NaOH, followed by water. The organic layer was evaporated under reduced pressure to a final volume of ~50 ml and crystallized from heptanes. The solid was collected by filtration and rinsed with ethyl acetate/heptanes (20 ml, 1:3). The wet product was dried at 40° C. for 12 h to obtain a white solid.

LC/MS: 1.54 min (2.1×50 mm, HSS T3 1.8 um at 50° C., 1.2 ml/min, gradient 2-98% acetonitrile (+0.04% formic acid) in water (+0.05% formic acid+3.75 mM NH4OAc);

MS (ESI): 446 [M+H]+, 1H NMR (500 MHz, CDCl3) δ (ppm): 7.89 (d, 2 H), 7.36 (d, 2 H), 6.48 (s, 1 H), 4.20 (s, 2 H), 3.16-3.22 (m, 2 H), 3.05-3.14 (m, 1 H), 2.68-2.80 (m, 7 H), 2.55 (s, 3 H), 2.04-2.13 (m, 2 H), 1.80-1.91 (m, 2 H), 1.20 (t, 3 H).

Example 36

4-{5-[4-(2-Ethyl-5,7-dimethyl-pyrazolo[1,5-a]pyrimidin-3-ylmethyl)-phenyl]-[1,3,4]oxadiazol-2-yl}-cyclohexylamine (Method B)

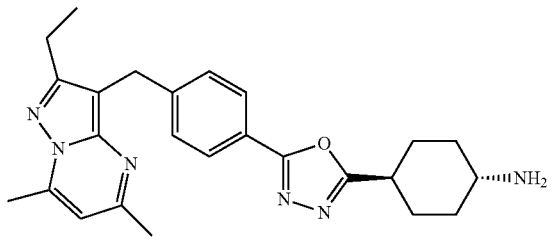 [SMILES: CCc1nn2c(C)cc(C)nc2c1Cc1ccc(-c2nnc([C@H]3CC[C@H](N)CC3)o2)cc1]

(1) Step A: (4-{N'-[4-(2-ethyl-5,7-dimethyl-pyrazolo[1,5-a]pyrimidin-3-ylmethyl)-benzoyl]-hydrazinocarbonyl}-cyclohexyl)-carbamic acid tert-butyl ester)

4-(2-Ethyl-5,7-dimethyl-pyrazolo[1,5-a]pyrimidin-3-ylmethyl)-benzoic acid hydrazide (29) (200 mg, 0.618 mmol), trans-4-(tert-butoxycarbonylamino) cyclohexanecarboxylic acid (226 mg, 0.928 mmol), EDC (119 mg, 0.618 mmol), HOBT (95 mg, 0.618 mmol) and Et3N (0.086 ml, 0.618 mmol) were dissolved in 2 ml of DMF and stirred for 16 h at rt. Then the mixture was diluted with EtOAc, washed with NaCl-solution and dried over Na2SO4. Evaporation gave a brown oil. The crude product was purified by chromatography (silica gel, methanol/EtOAc) to yield a white solid.

MS (ESI): 549 [M+H]+, 1H-NMR (DMSO-d6, 600 MHz) δ (ppm): 10.15 (s, 1H), 9.71 (s, 1H), 7.73 (d, 2H), 7.26 (d, 2H), 6.77 (s, 1H), 6.70 (br, 1H), 4.10 (s, 2H), 3.17 (m, 1H), 2.67 (q, 2H), 2.63 (s, 3H), 2.48 (s, 3H), 2.14 (m, 1H), 1.7-1.85 (m, 4H), 1.3-1.4 (m, 2H), 1.37 (s, 9H), 1.17 (m, 2H), 1.12 (t, 3H).

(2) Step B: 4-{1-[4-(2-ethyl-5,7-dimethyl-pyrazolo[1,5-a]pyrimidin-3-ylmethyl)-phenyl]-1H-[1,2,3]triazol-4-ylmethyl}-piperidin-4-ol (R'=Boc)

(4-{N'-[4-(2-Ethyl-5,7-dimethyl-pyrazolo[1,5-a]pyrimidin-3-ylmethyl)-benzoyl]-hydrazinocarbonyl}-cyclohexyl)- carbamic acid tert-butyl ester) (step A) (110 mg, 0.200 mmol) and tosylchloride (57.3 mg, 0.301 mmol) were dissolved in 2 ml of CH$_2$Cl$_2$ and 0.2 ml of DMF. Then Et$_3$N (0.111 ml, 0.802 mmol) was added and the reaction mixture was stirred for 4 h at rt. The reaction mixture was quenched with NaHCO$_3$ and extracted twice with CH$_2$Cl$_2$. The organic layers were washed with H$_2$O, combined, dried over Na$_2$SO$_4$ and concentrated. The residue was purified by chromatography (silica gel, methanol/EtOAc). MS (ESI): 531 [M+H]$^+$, $^1$H-NMR (DMSO-d6, 500 MHz) δ (ppm): 7.86 (d, 2H), 7.40 (d, 2H), 6.82 (br, 1H), 6.79 (s, 1H), 4.14 (s, 2H), 3.30 (m, 1H), 2.88 (m, 1H), 2.70 (q, 2H), 2.65 (s, 3H), 2.50 (s, 3H), 2.12 (m, 2H), 1.89 (m, 2H), 1.59 (m, 2H), 1.40 (s, 9H), 1.30 (m, 2H), 1.13 (t, 3H).

(3) Step C: 4-{5-[4-(2-Ethyl-5,7-dimethyl-pyrazolo[1,5-a]pyrimidin-3-ylmethyl)-phenyl]-[1,3,4]oxadiazol-2-yl}-cyclohexylamine hydrochloride (R'=H)

4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol (step B), (61 mg, 0.115 mmol) was dissolved in 1 ml of dioxane. Then 4M HCl in dioxane (0.287 ml, 1.150 mmol) was added and the mixture was stirred for 2 h at rt. The reaction mixture was concentrated. The residue was tritiated with diethylether and a yellow solid was filtered off. The compound was be used without further purification.

LC/MS: 1.72 min (2.1×50 mm, HSS T3 1.8 um at 50° C., 1.2 ml/min, gradient 2-98% acetonitrile (+0.04% formic acid) in water (+0.05% formic acid+3.75 mM NH$_4$OAc);

MS (ESI): 431 [M+H]$^+$, $^1$H-NMR (DMSO-d6, 600 MHz) δ (ppm): 8.10 (br, 3H), 7.85 (d, 2H), 7.39 (d, 2H), 6.79 (s, 1H), 4.14 (s, 2H), 3.07 (m, 1H), 2.97 (m, 1H), 2.68 (q, 2H), 2.64 (s, 3H), 2.48 (s, 3H), 2.18 (m, 2H), 2.06 (m, 2H), 1.63 (m, 2H), 1.51 (m, 2H), 1.12 (t, 3H).

Example 37

1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-2-methylamino-ethanone

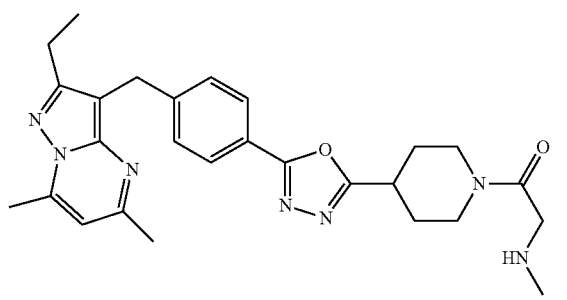

This compound was synthesized from example 36 analogously to example 8 step A using 2-(tert-butoxycarbonyl(methyl)amino)acetic acid followed by Boc-deprotection analogously to example 3 step B.

LC/MS: 1.55 min (2.1×50 mm, HSS T3 1.8 um at 50° C., 1.2 ml/min, gradient 2-98% acetonitrile (+0.04% formic acid) in water (+0.05% formic acid+3.75 mM NH$_4$OAc);

MS (ESI): 488 [M+H]$^+$, $^1$H-NMR (DMSO-d6, 600 MHz) δ (ppm): 7.85 (d, 2H), 7.38 (d, 2H), 6.75 (s, 1H), 4.26 (m, 1H), 4.12 (s, 2H), 3.77 (m, 1H), 3.60 (m, 2H), 3.34 (m, 1H), 3.21 (m, 1H), 2.94 (m, 1H), 2.67 (q, 2H), 2.62 (s, 3H), 2.47 (s, 3H), 2.38 (s, 3H), 2.07 (m, 2H), 1.76 (m, 1H), 1.62 (m, 1H), 1.11 (t, 3H).

Example 38

(S)-1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-3-hydroxy-2-methylamino-propan-1-one hydrochloride

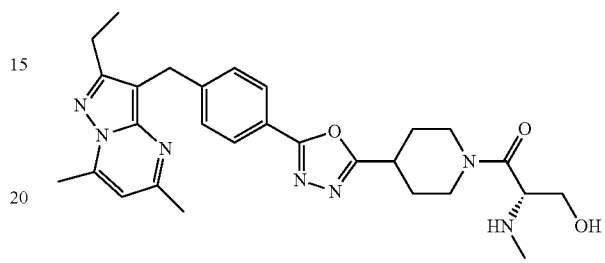

This compound was synthesized from example 36 analogously to example 8 step A using (S)-2-(tert-butoxycarbonyl(methyl)amino)-3-hydroxypropanoic acid followed by Boc-deprotection analogously to example 3 step B.

LC/MS: 0.74 min (4.6×50 mm, Sunfire C18, 5 um at 45° C., 2 ml/min, gradient 5-100% acetonitrile (+0.1% trifluoroacetic acid) in water (+0.1% trifluoroacetic acid) in 8 min;

MS (ESI): 518 [M+H]$^+$, $^1$H-NMR (DMSO-d6, 500 MHz) δ (ppm): 9.13 (br, 1H), 8.74 (br, 1H), 7.86 (m, 2H), 7.40 (d, 2H), 6.79 (s, 1H), 4.6 (br, 1H), 4.49 (m, 1H), 4.32 (m, 1H), 4.15 (s, 2H), 3.93 (m, 1H), 3.79 (m, 1H), 3.70 (m, 1H), 3.40 (m, 1H), 3.33 (m, 2H), 3.03 (m, 2H), 2.68 (q, 2H), 2.64 (s, 3H), 2.50 (s, 3H), 2.12 (m, 2H), 1.80 (m, 1H), 1.71 (m, 1H), 1.12 (t, 3H).

Example 39 (Labelled Compound for Binding Assay)

[$^3$H]$_4$-2-Ethyl-3-{4-[3-(4-isopropyl-piperazin-1-yl)-propyl]-benzyl}-5,7-dimethyl-pyrazolo[1,5-a]pyrimidine

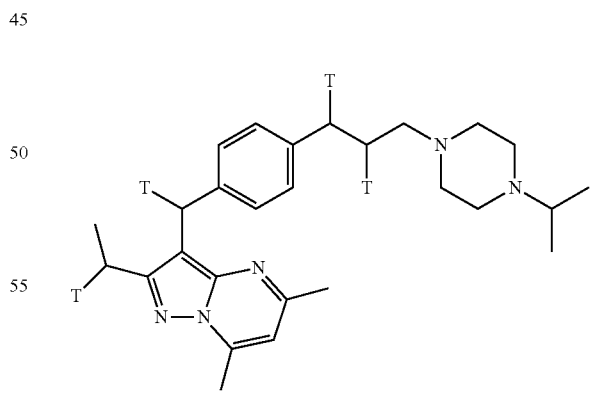

(1) Step A: 2-Ethyl-3-{4-[(E)-3-(4-isopropyl-piperazin-1-yl)-propenyl]-benzyl}-5,7-dimethyl-pyrazolo[1,5-a]pyrimidine dihydrochloride This compound was synthesized analogously to example 10 using 1-isopropylpiperazine.

MS (ESI): 432 [M+H]+, 1H-NMR (DMSO-d6, 500 MHz) δ (ppm): 12.1 (br, 1H), 11.8 (br, 1H), 7.37 (d, 2H), 7.21 (d, 2H), 6.84 (d, 1H), 6.77 (s, 1H), 6.29 (m, 1H), 4.05 (s, 2H), 3.93 (m, 2H), 3.4-3.8 (m, 9H), 2.66 (q, 2H), 2.63 (s, 3H), 2.49 (s, 3H), 1.28 (d, 6H), 1.12 (t, 3H).

(2) Step B: 2-Ethyl-3-{4-[(E)-3-(4-isopropyl-piperazin-1-yl)-propenyl]-benzyl}-5,7-dimethyl-pyrazolo[1,5-a]pyrimidine 2-Ethyl-3-{4-[(E)-3-(4-isopropyl-piperazin-1-yl)-propenyl]-benzyl}-5,7-dimethyl-pyrazolo[1,5-a]pyrimidine (step A) (70 mg, 0.13 mmol) was dissolved in 2 ml of methanol and after addition of Pd/C (14 mg) the mixture was hydrogenated with tritium for 2 h at rt. Then the mixture was filtrated over celite and evaporated under reduced pressure. The crude product was purified by preparative HPLC (methanol/water). The title compound was (partially) tritiated on 4 different locations as indicated in the formula shown above.

LC/MS: 1.26 min (2.1×50 mm, HSS T3 1.7 um at 50° C., 1.2 ml/min, gradient 2-98% acetonitrile (+0.04% formic acid) in water (+0.05% formic acid+3.75 mM NH$_4$OAc);

MS (ESI): 434 [M+H]+, 1H-NMR (DMSO-d6, 500 MHz) δ (ppm): 11.0-11.8 (br, 2H), 7.12 (m, 4H), 6.76 (s, 1H), 4.01 (s, 2H), 3.35-3.8 (m, 9H), 3.10 (m, 2H), 2.66 (q, 2H), 2.63 (s, 3H), 2.58 (m, 2H), 2.48 (s, 3H), 1.96 (m, 2H), 1.28 (d, 6H), 1.13 (t, 3H).

Example 40 (Comparative Example)

2-Ethyl-3-{4-[(E)-3-(4-isopropyl-piperazin-1-yl)-propenyl]-benzyl}-5,7-dimethyl-3H-imidazo[4,5-b]pyridine

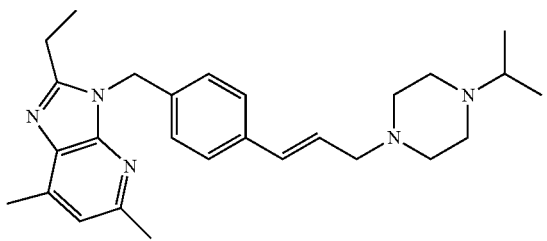 [SMILES: CCc1nc2c(C)cc(C)nc2n1Cc1ccc(/C=C/CN2CCN(C(C)C)CC2)cc1]

This compound has been prepared as described in WO 2009/144201, example No. 46.

The compounds of the invention in free form or in pharmaceutically acceptable salt form exhibit valuable pharmacological properties, e.g. as GPR4 antagonists as indicated in the various tests described below.

a) Human GPR4 Binding Assay

Assay measuring [3H]$_4$ (example 39) binding to membranes prepared from murine pre-B cell line 300.19 cells expressing human GPR4 receptor.

Membrane preparation: Homogenized membranes are prepared from murine pre-B cell line 300.19 clones stably expressing a human GPR4 with N-terminal c-myc tag. Cells were grown in T175 flasks to a density of about 1×10$^6$ cells/mL in growth medium. The cells were harvested by centrifugation (3000 rpm for 30 minutes at 4° C.) and the pellet resuspended in ice cold buffer A (20 mM HEPES pH 7.8, 10 mM EDTA, 100 mM NaCl, 1 tab/40 mL protease inhibitor complete). The cell suspension was homogenized on ice, using a Polytron homogenizer (PT10/35) at speed 8 at two intervals of 30 seconds each. The homogenate was centrifuged at 18000 rpm for 50 min at 4° C. and the membrane protein pellet resuspended in cold buffer A using the Polytron (2×20 seconds). The protein concentration is determined using the Bio Rad Protein Assay and human IgG as standard. The volume of the membrane protein suspension is adjusted to a final concentration of about 2 mg protein/mL. The suspension is then once again homogenized (Polytron) on ice at 25000 rpm for 20 seconds before being aliquoted and stored at −80° C.

Radio Ligand Binding Assay: Serial dilutions of compounds (stock in 10 mM DMSO) are prepared by first diluting the compounds in DMSO followed by a 1:50 dilution into assay buffer (10 mM HEPES, pH 8.0, 100 mM NaCl, 5 mM MgCl$_2$, 1 mM CaCl$_2$, 0.5% fatty acid-free BSA, 0.05% Tween-20). The radioligand [3H]$_4$ (example 39) (specific activity 1500 GBq/mmol) is diluted directly into the assay buffer immediately before use to obtain a 20 nM solution. The desired amount of membranes (20 μg/well) is diluted with assay buffer. 50 μL of pre-diluted compound and 50 μL of [3H]$_4$ (example 39) is placed into the bottom of a 96-well well plate. 100 μL of the membrane-suspension is added and the plate stirred for 60 minutes. The reaction is stopped by transfer onto the filter of a 96-well GF/C filter plate (soaked for 1 hour in 0.25% PEI) using a cell harvester. The filter plate is washed 5 times with ice-cold wash buffer, dried and sealed at the bottom. Then 20 μL of Microscint 40 is added into each well and the top of the plate is sealed. Finally the plate is counted for 2 min/well in a TopCount NXT instrument (Packard Instruments). The data are analyzed using the GraphPad Prism™ software.

As negative control, membranes isolated from parental (non-transfected) murine pre-B cell line 300.19 were used. In the presence of 5 nM radioligand [3H]$_4$ (example 39) a background signal was observed only. This experiment confirms the affinity of the radioligand example 39 with the human GPR4 receptor.

Based upon the above described test procedure, the compounds of the invention exhibited the following IC$_{50}$ values:

| Example | GPR4 [nM] |
| --- | --- |
| 1 | 45 |
| 2 | 34 |
| 3 | 44 |
| 4 | 47 |
| 5 | 15 |
| 6 | 24 |
| 7 | 34 |
| 8 | 28 |
| 9 | 19 |
| 10 | 33 |
| 11 | 38 |
| 12 | 33 |
| 13 | 7 |
| 14 | 10 |
| 15 | 51 |
| 16 | 35 |
| 17 | 30 |
| 18 | 81 |
| 19 | 54 |
| 20 | nd |
| 21 | 22 |
| 22 | 19 |
| 23 | 35 |
| 24 | 54 |
| 25 | 110 |
| 26 | 44 |
| 27 | 59 |
| 28 | 118 |

-continued

| Example | GPR4 [nM] |
|---------|-----------|
| 29 | 21 |
| 30 | 26 |
| 31 | 43 |
| 32 | nd |
| 33 | 38 |
| 34 | 77 |
| 35 | 74 |
| 36 | 5 |
| 37 | nd |
| 38 | 15 |
| 39 | 13 |
| 40 | 55 |

In a similar manner, a binding assay with additional human serum albumin (4% HSA) has been established. In this assay the compounds of the invention exhibited the following $IC_{50}$ values:

| Example | GPR4 4% HSA [nM] |
|---------|------------------|
| 1 | 25 |
| 2 | 52 |
| 3 | 49 |
| 4 | nd |
| 5 | 11 |
| 6 | 18 |
| 7 | 56 |
| 8 | 51 |
| 9 | 6 |
| 10 | 93 |
| 11 | nd |
| 12 | nd |
| 13 | 7 |
| 14 | 12 |
| 15 | 44 |
| 16 | 120 |
| 17 | 78 |
| 18 | 67 |
| 19 | 28 |
| 20 | nd |
| 21 | 13 |
| 22 | 12 |
| 23 | 19 |
| 24 | 63 |
| 25 | 63 |
| 26 | 69 |
| 27 | 81 |
| 28 | 180 |
| 29 | 30 |
| 30 | 18 |
| 31 | 61 |
| 32 | nd |
| 33 | nd |
| 34 | 78 |
| 35 | 51 |
| 36 | 17 |
| 37 | nd |
| 38 | 29 |
| 39 | nd |
| 40 | 512 | b) Cell-Based Assay for Human GPR4 Activity

HeLa cells stably expressing human GPR4 were established by transfecting the cells with a construct containing the human GPR4 coding sequence. The cells were grown in Dulbecco's Modified Eagle Medium (DMEM)/HAM's tissue culture medium F12 (HAM's F12) supplemented with 10% fetal calf serum (FCS), 100 u/ml penicillin, 100 µg/ml streptomycin and 400 µg/ml G418 and 10 mM Hepes pH 8.0. pH-induced formation of cAMP was determined using the homogeneous time resolved fluorescence (HTRF) technology as provided by CisBio Inc. The cells were seeded in 384-well plates and cultured for 24 hours at 37° C., 5% $CO_2$ before performing the assay. Medium was removed and 10 µl buffer A (Hepes buffered saline (HBS), 10 mM Hepes, pH 8, 2 mM 3-Isobutyl-1-methylxanthin (IBMX)) was added. For compound testing, buffer A with 2× concentrated compounds was used. Cells were incubated for 15 min at room temperature. 10 µl buffer B (HBS, 30 mM Hepes, specific pH) was added to reach the appropriate final pH for stimulation (see below) and incubation was continued for 15 min at room temperature. Finally, 10 µl of cAMP-XL 665 and 10 µl anti cAMP-cryptate were dispensed and plates were read on a Pherastar reader after 60 min incubation at room temperature. Data were calculated from the 665 nm/620 nm ratio and % activity was normalized according to values at minimum and maximum of GPR4 activation. HBS: 130 mM NaCl, 0.9 mM $NaH_2PO_4$, 5.4 mM KCl, 0.8 mM $MgSO_4$, $CaCl_2$ 1.8 mM, 25 mM glucose, 10-30 mM Hepes. Adjustment of HBS buffers:

| Buffer A | Buffer B |
|----------|----------|
| Final stimulation pH (1 volume buffer A + 1 volume buffer B) | |
| pH 5.68 | 6.92 |
| pH 6.19 | 6.98 |
| pH 6.46 | 7.04 |
| pH 6.86 | 7.19 |
| pH 7.26 | 7.44 |
| pH 7.62 | 7.70 |
| pH 8.00 | 8.00 |
| pH 8.19 | 8.14 |

Compounds were diluted from fresh stock solutions at 10 mM in DMSO to 2 mM and then used for serial dilutions in DMSO. 2× concentrated compound solutions were prepared to reach final concentrations of 20, 6.33, 2, 0.63, 0.2, 0.063, 0.02, 0.0063 uM (micro molar).

Based upon the above described test procedure, the compounds of the invention exhibited the following $IC_{50}$ values:

| Exmple | cAMP [nM] |
|--------|-----------|
| 1 | 37 |
| 2 | 55 |
| 3 | 31 |
| 4 | 50 |
| 5 | 17 |
| 6 | 19 |
| 7 | 33 |
| 8 | 34 |
| 9 | 59 |
| 10 | 54 |
| 11 | 46 |
| 12 | 27 |
| 13 | 68 |
| 14 | 55 |
| 15 | 56 |
| 16 | 41 |
| 17 | 21 |
| 18 | 43 |
| 19 | 44 |
| 20 | 79 |
| 21 | 12 |
| 22 | 13 |
| 23 | 21 |
| 24 | 70 |
| 25 | 52 |

| Exmple | cAMP [nM] |
|---|---|
| 26 | 96 |
| 27 | 64 |
| 28 | 49 |
| 29 | 36 |
| 30 | 29 |
| 31 | 53 |
| 32 | 61 |
| 33 | 31 |
| 34 | 58 |
| 35 | 50 |
| 36 | 51 |
| 37 | 40 |
| 38 | 45 |
| 39 | 18 |
| 40 | 114 |

In a similar manner, assays for the mouse (m) and rat (r) GPR4 receptors have been established. Due to the species specificity of the GPR4 antagonists, the compounds of the invention had an $IC_{50}$ between 0.07 and 1.92 µM in the mouse GPR4 assay and between 0.18 and 2.64 µM (micromolar) in rat GPR4 assay:

| Ex | m cAMP [nM] |
|---|---|
| 1 | 265 |
| 2 | 632 |
| 3 | 124 |
| 4 | 125 |
| 5 | 70 |
| 6 | 128 |
| 7 | 253 |
| 8 | 378 |
| 9 | 890 |
| 10 | 401 |
| 11 | 499 |
| 12 | 233 |
| 13 | 388 |
| 14 | 127 |
| 15 | 216 |
| 16 | 200 |
| 17 | 86 |
| 18 | 1283 |
| 19 | 1924 |
| 20 | 366 |
| 21 | 96 |
| 22 | 90 |
| 23 | 262 |
| 24 | 365 |
| 25 | 635 |
| 26 | 633 |
| 27 | 507 |
| 28 | 687 |
| 29 | 211 |
| 30 | 384 |
| 31 | 511 |
| 32 | 255 |
| 33 | 872 |
| 34 | 534 |
| 35 | 982 |
| 36 | 284 |
| 37 | nd |
| 38 | 180 |
| 39 | 123 |
| 40 | 760 |

| Ex | r cAMP [nM] |
|---|---|
| 1 | 931 |
| 2 | 989 |
| 3 | 338 |
| 4 | 1171 |
| 5 | 162 |
| 6 | 491 |
| 7 | 1724 |
| 8 | 670 |
| 9 | 1443 |
| 10 | 1340 |
| 11 | 2791 |
| 12 | 181 |
| 13 | 1694 |
| 14 | 691 |
| 15 | 634 |
| 16 | 837 |
| 17 | 949 |
| 18 | 1795 |
| 19 | 2580 |
| 20 | 1502 |
| 21 | 489 |
| 22 | 202 |
| 23 | 1412 |
| 24 | 792 |
| 25 | 2087 |
| 26 | 2644 |
| 27 | 2629 |
| 28 | 2303 |
| 29 | 430 |
| 30 | 497 |
| 31 | 1333 |
| 32 | 1331 |
| 33 | 616 |
| 34 | 1227 |
| 35 | 972 |
| 36 | 2286 |
| 37 | nd |
| 38 | 811 |
| 39 | 274 |
| 40 | 1290 | c) Human H3 Binding Assay

The Scintillation Proximity Binding Assay (SPA) assay was performed in a final volume of 50 µL per well in a 384-well polystyrene plate. The components of the wells were added as follows:

10 µL test compounds in 1.5% DMSO/distilled water

Total binding was determined by adding 10 µL water with 1.5% DMSO and non specific binding was determined by the addition of 10 µL Clobenpropit (10 µM final concentration).

20 µL [$^3$H]-R-alpha-Methylhistamine 7.5 nM in assay buffer (50 mM Tris-HCl, 5 mM EDTA, 1 mM EDTA, pH 7.4). The final concentration of the radioligand was 3 nM.

20 µL of a beads (PVT-WGA type A) and membranes mixed suspension in assay buffer, in order to get a final concentration of 10 µg/well of membranes and 200 µg/well of beads. As an example, 1471 µL membranes (Conc.: 5.1 mg/mL) and 1500 µL of bead suspension (Conc.: 100 mg/mL) are diluted to a final volume of 15 mL of assay buffer.

The plates were sealed and shaken at room temperature, then allowed to stand at room temperature for at least 1 hour. The plates were counted using a Perkin Elmer TopCount reader, each well being counted for 1 minute.

| Example | h H3 [uM] |
|---|---|
| 1 | >30 |
| 2 | >10 |
| 3 | >30 |
| 4 | >10 |
| 5 | >30 |
| 6 | nd |
| 7 | >30 |
| 8 | >30 |
| 9 | 18 |
| 10 | >30 |
| 11 | >30 |
| 12 | >30 |
| 13 | 4.9 |
| 14 | >30 |
| 15 | 26 |
| 16 | >30 |
| 17 | >30 |
| 18 | >30 |
| 19 | >30 |
| 20 | >30 |
| 21 | 25 |
| 22 | >30 |
| 23 | >30 |
| 24 | >30 |
| 25 | >30 |
| 26 | >30 |
| 27 | >30 |
| 28 | 20 |
| 29 | >30 |
| 30 | >30 |
| 31 | >30 |
| 32 | >30 |
| 33 | >10 |
| 34 | >30 |
| 35 | >10 |
| 36 | >30 |
| 37 | nd |
| 38 | >30 |
| 39 | 0.17 |
| 40 | 0.9 | d) GPR4 Activity in VEGF-Induced Angiogenesis in Mice

The functional activity of GPR4 was determined in the angiogenesis growth factor implant model. Porous tissue chambers made of perfluoro-alkoxy-Teflon were filled with 0.8% agar and 20 U/ml heparin supplemented with or without 8 μg/ml recombinant human VEGF. The solutions were maintained at 39° C. prior to the filling procedure. Mice were anesthetized using 3% isoflurane inhalation. For subcutaneous implantation, a small skin incision was made at the base of the tail to allow the insertion of an implant trocar. The chamber was implanted under aseptic conditions through the small incision onto the back of the animal. The skin incision was closed by wound clips. The compounds were applied po at 30 mg/kg bid starting at the day of the chamber implantation.

On the 4th day after implantation, animals were sacrificed using $CO_2$. Chambers were excised and the vascularized fibrous tissue formed around each implant carefully removed and weighed and expressed as Δ tissue weight % [((compound/VEGF)−(no compound/no VEGF))/((no compound/VEGF)−no compound/no VEGF))×100]. Body weight was used to monitor the general condition of the mice.

| Compound Example No. | Dose [mg/kg] | Δ tissue weight [%] |
|---|---|---|
| 9 | 30 (bid) | 44 |
| 35 | 30 (bid) | 49 | e) GPR4 Activity in Rat Antigen-induced Arthritis Model

Female Lewis rats were sensitised intradermally on the back at two sites to methylated bovine serum albumin (mBSA) homogenised 1:1 with complete Freund's adjuvant on days −21 and −14 (0.1 ml containing 1 mg/ml mBSA). On day 0, the right knee received 50 ml of 10 mg/ml mBSA in 5% glucose solution (antigen injected knee), while the left knee received 50 ml of 5% glucose solution alone (vehicle injected knee). The diameters of the left and right knees were then measured using calipers immediately after the intra-articular injections and again on days 2, 4 and 7. The compounds of the invention were administered twice daily by oral gavage; vehicle (saline) at 5 ml/kg, and dexamethasone at 0.3 mg/kg was given as a control. Right knee swelling was calculated as a ratio of left knee swelling, and the R/L knee swelling ratio plotted against time to give Area Under the Curve (AUC) graphs for control and treatment groups. The percentage inhibition of the individual treatment group AUCs were calculated vs the control group AUC (0% inhibition).

| example | Dose [mg/kg] | Inhibition of swelling |
|---|---|---|
| 8 | 90 (bid) | 30 |
| 17 | 30 (bid) | 36 |
| 23 | 30 (bid) | 24 |
| 28 | 90 (bid) | 25 |
| 31 | 30 (bid) | 24 |
| 31 | 60 (bid) | 38 |
| 35 | 30 (bid) | 26 |
| 35 | 60 (bid) | 34 |
| 35 | 90 (bid) | 40 | f) Established Rat Hyperalgesia Model

Naïve withdrawal thresholds of both hind paws were determined by using an increasing pressure stimulus placed onto the dorsal surface of each paw using an analgesymeter. Delayed inflammatory pain was then induced by intra-plantar injection of 25 μl of complete Freund's adjuvant (CFA) into one hindpaw with the contralateral paw acting as the control. After 3 days, compounds of the invention (3, 10, and 30 mg/kg), or diclofenac (30 mg/kg) as a control, or vehicle, were administered by gavage as suspension in methylcellulose 5%. One hour later, paw withdrawal thresholds were re-measured on both the ipsilateral (CFA-injected) and contralateral (uninjected) paw; measurements were repeated at 3 hrs and 6 hrs post dosing. The reversal of hyperalgesia was calculated using the following formula: Reversal (%)=100× (postdose ipsilateral threshold−predose ipsilateral threshold)/(naïve ipsilateral threshold−predose ipsilateral threshold).

| example | Dose [mg/kg] | % reversal of hyperalgesia | | |
| --- | --- | --- | --- | --- |
| | | 1 h | 3 h | 6 h |
| vehicle | | 5 | 3 | 3 |
| diclofenac | 30 | 58 | 60 | 30 |
| 17 | 3 | 28 | 18 | 3 |
| 17 | 10 | 36 | 29 | 7 |
| 17 | 30 | 55 | 32 | 15 |
| 35 | 3 | 36 | 25 | 5 |
| 35 | 10 | 43 | 36 | 15 |
| 35 | 30 | 62 | 47 | 25 |
| 40 | 3 | 23 | 11 | 0 |
| 40 | 10 | 48 | 40 | 0 |
| 40 | 30 | 55 | 45 | 8 |

The compounds of the present invention are in particular useful in the treatment wherein GPR4 modulation such as inhibition plays a role, for example wherein proton homeostasis is imbalanced, and hence may be useful in treating medical conditions selected from the group consisting of:

Osteoporosis (juvenile, menopausal, post-menopausal, post-traumatic, caused by old age or corticosteroid therapy or inactivity), gingivitis, periodontitis, Paget's disease, hypercalcemia of malignancy, tumor induced hypercalcemia, metabolic bone disease, cancer, solid tumors, cardiovascular disorders, atherosclerose, myocardial infarction, limb diseases, peripheral arterial occlusive disease, eye diseases, diabetic retinopathy, macular degeneration, uveitis, arthritis, rheumatoid arthritis, osteoarthritis, wound healing, skin diseases, inflammatory and obstructive airway diseases, asthma, intrinsic and extrinsic asthma, mild asthma, moderate asthma, severe asthma, bronchitic asthma, exercise induced asthma, occupational asthma and asthma induced following bacterial infection, acute lung injury, acute/adult respiratory distress syndrome, chronic obstructive pulmonary airways or lung diseases, chronic bronchitis, dyspnea associated herewith, emphysema, exacerbation of airways hyperactivity consequent to other drug therapy, bronchitis, acute arachidic, catarrhal, croupus, chronic or phthinoid bronchitis.

Pneumoconiosis, aluminosis, anthracosis, asbestosis, chlicosis, ptilosis, siderosis, silicosis, tabacosis byssinosis, eosinophilia, bronchopulmonar aspergillosis, polyarteritis nodosa, eosinophilic granuloma and eosinophil-related disorders affecting the airways occasioned by drug reaction, infections by organisms such as *pneumocystis carinii, trypanosoma cruzi, trypanosoma brucei*, crithidia fusculata, parasitic diseases such as schistosomiasis and malaria, sarcoidosis and other granulmomatous inflammation, tumor invasion and metastasis, metachromatic leukodystrophy, muscular dystrophy, amythrophy, autoimmune disease, respiratory disease, immunologically mediated disease, transplant rejection, inflammatory pain, visceral pain, acute and chronic pain, tumor pain, neuropathic pain, kidney diseases, renal tubular acidosis and other disorders of acid-base and metabolism, Crohn's disease, inflammatory bowel disease, hypersensitivity reactions.

There is further provided a compound of the present invention for use as a pharmaceutical, in particular for use in the treatment of a disease or disorder being mediated by the GPR4 receptor, especially by the inhibition of GPR4.

As used herein the term "mediation" by or "modulation" of the GPR4 receptor addresses in particular the inhibition of the GPR4 receptor by a compound of the invention.

In another embodiment the invention provides a method of modulating GPR4 receptor activity in a subject, in particular a method of treating a disorder or a disease in a subject mediated by the GPR4 receptor, wherein the method comprises administering to the subject a therapeutically effective amount of the compound according to the present invention.

In another embodiment the invention provides the method or use in accordance to the preceding paragraphs, wherein said treatment of a disorder or disease in a subject mediated by the GPR4 receptor or characterized by an activity of the GPR4 receptor.

In another embodiment the invention provides a pharmaceutical composition comprising a compound of the present invention together with a pharmaceutically acceptable carrier.

In another embodiment the invention provides a combination comprising a compound of the invention together with one or more other suitable active agents, which may be selected from but which are not limited to the following classes of agents: Anti IL-1 agents, e.g: Anakinra; anti cytokine and anti-cytokine receptor agents, e.g. anti IL-6 R Ab, anti IL-15 Ab, anti IL-17 Ab, anti IL-12 Ab; B-cell and T-cell modulating drugs, e.g. anti CD20 Ab; CTL4-1 g, disease-modifying anti-rheumatic agents (DMARDs), e.g. methotrexate, leflunamide, sulfasalazine; anti-nocioceptive and analgesic agents including but not limited to nonsteroidal anti-inflammatory agents (including both non-selective and selective COX2 inhibitors) and salicylic acid derivatives, acetaminophen; natural and synthetic opiods; agents which modulate migration of immune cells, e.g. chemokine receptor antagonists; modulators of adhesion molecules, e.g. inhibitors of LFA-1, VLA-4; anti-tumor agents, e.g. VEGF-inhibitors, or PDGFR-inhibitors; and also cytotoxic and anti-mitotic agents.

Another embodiment of the invention describes a combination, e.g. a pharmaceutical combination or a kit, comprising a) a first agent which is a compound of the present invention, or a salt thereof, in particular a pharmaceutically acceptable salt thereof, and b) at least one co-agent, e.g. an immunosuppressant, immunomodulatory, anti-inflammatory, chemotherapeutic or anti-infectious agent.

Summary of the Invention

Embodiment one relates to a compound of formula (I) or a pharmaceutically acceptable salt thereof,

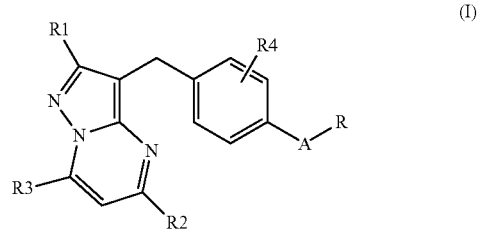

(I)

wherein
R1 is H or $C_1$-$C_6$ alkyl;
R2 and R3 are independently from each other H or $C_1$-$C_6$ alkyl;
A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—

—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—,

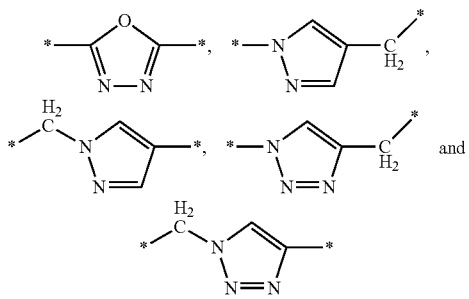

(wherein a * denote the link (or places of attachment));

R stands for heterocyclyl or cycloalkyl, each of which may be optionally substituted 1 to 4 times; and R4 is H, C$_1$-C$_6$ alkyl, C$_1$-C$_6$ alkoxy, halogen, hydroxy, cyano or trifluoromethyl.

Embodiment two relates to a compound of formula (I') or a pharmaceutically acceptable salt thereof,

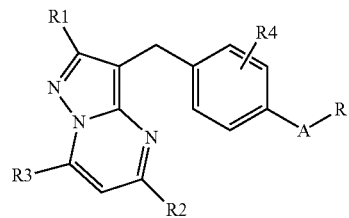

(I')

wherein

R1 is H or C$_1$-C$_6$ alkyl;

R2 and R3 are independently from each other H or C$_1$-C$_6$ alkyl;

A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—,

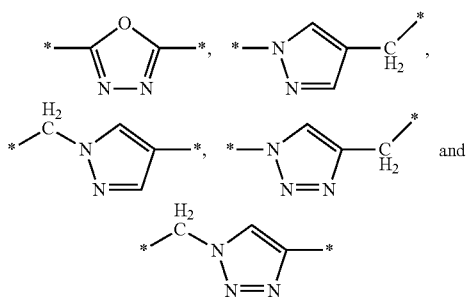

(wherein a * denote the link (or places of attachment));

R stands for azetidine, pyrrolidine, piperidine, piperazine, cyclohexane or cyclopentane, each of which may be optionally substituted 1 to 4 times by oxo (=O); hydroxy; C$_1$-C$_6$ alkyl optionally substituted one or more times by hydroxy, oxo (=O), amino optionally substituted by C$_1$-C$_6$ alkoxycarbonyl, mono C$_1$-C$_6$ alkyl-amino optionally substituted by C$_1$-C$_6$ alkoxycarbonyl, di-C$_1$-C$_6$ alkyl-amino, C$_1$-C$_6$ alkoxy, C$_1$-C$_6$ alkoxycarbonyl or tri-C$_1$-C$_6$ alkyl silyloxy; tetrazole optionally substituted by C$_1$-C$_6$ alkyl; a hydroxypyrrolidine-carbonyl group; a hydroxypyrrolidine-aminocarbonyl group or a hydroxypyrrolidine-carbonylamino group; and R4 is H, C$_1$-C$_6$ alkyl, C$_1$-C$_6$ alkoxy, halogen, hydroxy, cyano or trifluoromethyl.

Embodiment three relates to a compound of formula (I") or a pharmaceutically acceptable salt thereof,

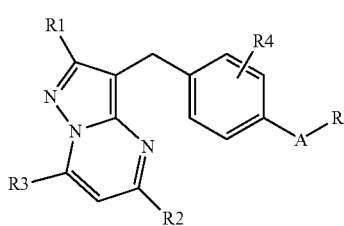

(I")

wherein

R1 is H or C$_1$-C$_6$ alkyl;

R2 and R3 are independently from each other H or C$_1$-C$_6$ alkyl;

A is a bivalent linking group selected from the group consisting of: —CH=CH—, —CH=CH—CH$_2$—, —CH$_2$—CH$_2$—CH$_2$—, —CH=CH—C(O)—, —CH$_2$—CH$_2$—C(O)—, —C(O)—NH—CH$_2$—, —O—CH$_2$—, —O—CH$_2$—CH$_2$—,

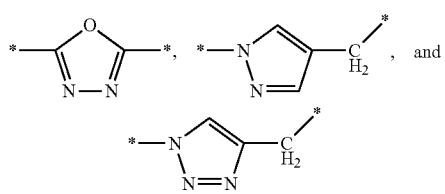

(wherein a * denote the link (or places of attachment));

R stands for azetidine, pyrrolidine, piperidine, piperazine, cyclohexane or cyclopentane, each of which may be optionally substituted 1 to 4 times by oxo (=O); hydroxy; C$_1$-C$_6$ alkyl optionally substituted one or more times by hydroxy, oxo (=O), amino optionally substituted by C$_1$-C$_6$ alkoxycarbonyl, mono C$_1$-C$_6$ alkyl-amino optionally substituted by C$_1$-C$_6$ alkoxycarbonyl, di-C$_1$-C$_6$ alkyl-amino, C$_1$-C$_6$ alkoxy, C$_1$-C$_6$ alkoxycarbonyl or tri-C$_1$-C$_6$ alkyl silyloxy; tetrazole optionally substituted by C$_1$-C$_6$ alkyl; a hydroxypyrrolidine-carbonyl group; a hydroxypyrrolidine-aminocarbonyl group or a hydroxypyrrolidine-carbonylamino group; and R4 is H or C$_1$-C$_6$ alkyl.

Embodiment four relates to a compound in accordance to the definition of embodiment one, which is a compound of formula (II) or a pharmaceutically acceptable salt thereof,

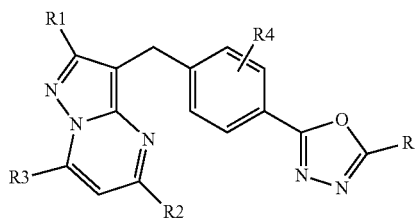

(II)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

Embodiment five relates to a compound in accordance to the definition of embodiment one, which is a compound of formula (III) or a pharmaceutically acceptable salt thereof,

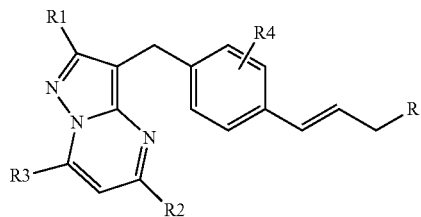

(III)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

Embodiment six relates to a compound in accordance to the definition of embodiment 1, which is a compound of formula (IV) or a pharmaceutically acceptable salt thereof,

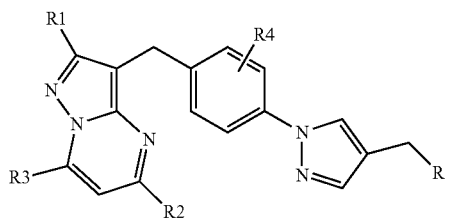

(IV)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

Embodiment seven relates to a compound in accordance to the definition of embodiment 1, which is a compound of formula (V) or a pharmaceutically acceptable salt thereof,

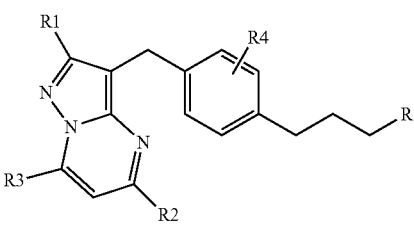

(V)

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, or $C_1$-$C_6$ alkoxycarbonyl; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H or $C_1$-$C_6$ alkyl.

Embodiment eight relates to a compound of any one of embodiments 1, 2, 3, 4, 5 or 6, or a pharmaceutically acceptable salt thereof, wherein R1 is $C_1$-$C_2$ alkyl;

R2 and R3 are independently from each other methyl;

R stands for piperidine or piperazine which may be optionally substituted 1 to 2 times by $C_1$-$C_6$ alkyl optionally substituted one or more times by hydroxy, oxo (=O), amino optionally substituted by $C_1$-$C_6$ alkoxycarbonyl, or mono $C_1$-$C_6$ alkyl-amino optionally substituted by $C_1$-$C_6$ alkoxycarbonyl; and R4 is H.

Embodiment nine relates to a compound of any one of embodiments 1, 2, 3, 4, 5, 6 or 7, or a pharmaceutically acceptable salt thereof, wherein R1 is ethyl;

R2 and R3 are independently from each other methyl;

R stands for 4-piperidinyl or 1-piperazinyl which may be optionally substituted 1 to 2 times by $C_1$-$C_6$ alkyl optionally substituted 1-3 times by hydroxy, oxo (═O), or mono $C_1$-$C_6$ alkyl-amino, with the proviso that the substituent $C_1$-$C_6$ alkyl cannot be unsubstituted when $C_1$-$C_6$ alkyl is attached to a N-atom;

and

R4 is H.

Embodiment ten relates to a compound of any one of previous embodiments, or a pharmaceutically acceptable salt thereof, wherein the compound is selected from:

4-{(E)-2-[4-(2-Ethyl-5,7-dimethyl-pyrazolo[1,5-a]pyrimidin-3-ylmethyl)-phenyl]-vinyl}-piperidin-4-ol, 4-{(E)-2-[4-(2-Ethyl-5,7-dimethyl-pyrazolo[1,5-a]pyrimidin-3-ylmethyl)-phenyl]-vinyl}-4-hydroxy-piperidine-1-carboxylic acid tert-butyl ester, 3-{(E)-3-[4-(2-Ethyl-5,7-dimethyl-pyrazolo[1,5-a]pyrimidin-3-ylmethyl)-phenyl]-allyl}-azetidin-3-ol, 3-{(E)-3-[4-(2-Ethyl-5,7-dimethyl-pyrazolo[1,5-a]pyrimidin-3-ylmethyl)-phenyl]-allyl}-3-hydroxy-azetidine-1-carboxylic acid tert-butyl ester, 4-{(E)-3-[4-(2-Ethyl-5,7-dimethyl-pyrazolo[1,5-a]pyrimidin-3-ylmethyl)-phenyl]-allyl}-piperidin-4-ol, 4-{(E)-3-[4-(2-Ethyl-5,7-dimethyl-pyrazolo[1,5-a]pyrimidin-3-ylmethyl)-phenyl]-allyl}-4-hydroxy-piperidine-1-carboxylic acid tert-butyl ester, 4-{3-[4-(2-Ethyl-5,7-dimethyl-pyrazolo[1,5-a]pyrimidin-3-ylmethyl)-phenyl]-propyl}-piperidin-4-ol, 4-{3-[4-(2-Ethyl-5,7-dimethyl-pyrazolo[1,5-a]pyrimidin-3-ylmethyl)-phenyl]-propyl}-4-hydroxy-piperidine-1-carboxylic acid tert-butyl ester, (2S,4S)-4-{(E)-3-[4-(2-Ethyl-5,7-dimethyl-pyrazolo[1,5-a]pyrimidin-3-ylmethyl)-phenyl]-allyl}-2-methyl-piperidin-4-ol, 1-{(E)-3-[4-(2-Ethyl-5,7-dimethyl-pyrazolo[1,5-a]pyrimidin-3-ylmethyl)-phenyl]-allyl}-piperazin-2-one, (R)-3-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-propane-1,2-diol, 1-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-methylamino-ethanone,

[2-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-oxo-ethyl]-methyl-carbamic acid tert-butyl ester, ((S)-4-{(E)-3-[4-(2-Ethyl-5,7-dimethyl-pyrazolo[1,5-a]pyrimidin-3-ylmethyl)-phenyl]-allyl}-piperazin-2-yl)-methanol, (S)-4-{(E)-3-[4-(2-Ethyl-5,7-dimethyl-pyrazolo[1,5-a]pyrimidin-3-ylmethyl)-phenyl]-allyl}-2-hydroxymethyl-piperazine-1-carboxylic acid tert-butyl ester, 2-Ethyl-5,7-dimethyl-3-{4-[(E)-3-((S)-3-methyl-piperazin-1-yl)-propenyl]-benzyl}-pyrazolo[1,5-a]pyrimidine, 2-Ethyl-3-{4-[(E)-3-((S)-3-methoxymethyl-piperazin-1-yl)-propenyl]-benzyl}-5,7-dimethyl -pyrazolo[1,5-a]pyrimidine, 2-Amino-1-(4-{(E)-3-[4-(2-ethyl-5,7-dimethyl-pyrazolo[1,5-a]pyrimidin-3-ylmethyl)-phenyl]-allyl}-piperazin-1-yl)-ethanone, 2-Ethyl-5,7-dimethyl-3-(4-{(E)-3-[4-(1-methyl-1H-tetrazol-5-yl)-piperidin-1-yl]-propenyl}-benzyl)-pyrazolo[1,5-a]pyrimidine, ((S)-4-{(E)-3-[4-(2-Ethyl-5,7-dimethyl-pyrazolo[1,5-a]pyrimidin-3-ylmethyl)-phenyl]-allyl}-piperazin-2-ylmethyl)-dimethyl-amine, (R)-2-Dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester, (S)-2-Dimethylaminomethyl-4-{(E)-3-[4-(2-ethyl-5,7-dimethyl-pyrazolo[1,5-a]pyrimidin-3-ylmethyl)-phenyl]-allyl}-piperazine-1-carboxylic acid tert-butyl ester, 2-Ethyl-5,7-dimethyl-3-[4-((E)-3-piperazin-1-yl-propenyl)-benzyl]-pyrazolo[1,5-a]pyrimidine, (S)-1-(4-{(E)-3-[4-(2-Ethyl-5,7-dimethyl-pyrazolo[1,5-a]pyrimidin-3-ylmethyl)-phenyl]-allyl}-piperazin-1-yl)-3-hydroxy-2-methylamino-propan-1-one, (4-{(E)-3-[4-(2-Ethyl-5,7-dimethyl-pyrazolo[1,5-a]pyrimidin-3-ylmethyl)-phenyl]-allyl}-piperazin-1-yl)-((2S,3R)-3-hydroxy-pyrrolidin-2-yl)-methanone, (R)-3-(4-{(E)-3-[4-(2-Ethyl-5,7-dimethyl-pyrazolo[1,5-a]pyrimidin-3-ylmethyl)-phenyl]-allyl}-piperazin-1-yl)-propane-1,2-diol, (R)-1-(tert-Butyl-dimethyl-silanyloxy)-3-(4-{(E)-3-[4-(2-ethyl-5,7-dimethyl-pyrazolo[1,5-]pyrimidin-3-ylmethyl)-phenyl]-allyl}-piperazin-1-yl)-propan-2-ol, (E)-3-[4-(2-Ethyl-5,7-dimethyl-pyrazolo[1,5-a]pyrimidin-3-ylmethyl)-phenyl]-1-piperazin-1-yl-propenone, 4-{(E)-3-[4-(2-Ethyl-5,7-dimethyl-pyrazolo[1,5-a]pyrimidin-3-ylmethyl)-phenyl]-acryloyl}-piperazine-1-carboxylic acid tert-butyl ester, 3-[4-(2-Ethyl-5,7-dimethyl-pyrazolo[1,5-a]pyrimidin-3-ylmethyl)-phenyl]-1-piperazin-1-yl -propan-1-one, 4-{3-[4-(2-Ethyl-5,7-dimethyl-pyrazolo[1,5-a]pyrimidin-3-ylmethyl)-phenyl]-propionyl}-piperazine-1-carboxylic acid tert-butyl ester, 4-(2-Ethyl-5,7-dimethyl-pyrazolo[1,5-a]pyrimidin-3-ylmethyl)-N-piperidin-4-ylmethyl -benzamide, 2-Ethyl-5,7-dimethyl-3-[4-(piperidin-4-ylmethoxy)-benzyl]-pyrazolo[1,5-a]pyrimidine, 4-[4-(2-Ethyl-5,7-dimethyl-pyrazolo[1,5-a]pyrimidin-3-ylmethyl)-phenoxymethyl]-piperidine-1-carboxylic acid tert-butyl ester, {4-[4-(2-Ethyl-5,7-dimethyl-pyrazolo[1,5-a]pyrimidin-3-ylmethyl)-phenoxymethyl]-piperidin-1-yl}-((2S,3R)-3-hydroxy-pyrrolidin-2-yl)-methanone, 4-[4-(2-Ethyl-5,7-dimethyl-pyrazolo[1,5-a]pyrimidin-3-ylmethyl)-phenoxymethyl]-cyclohexylamine, (2S,3R)-3-Hydroxy-pyrrolidine-2-carboxylic acid {4-[4-(2-ethyl-5,7-dimethyl-pyrazolo[1,5-a]pyrimidin-3-ylmethyl)-phenoxymethyl]-cyclohexyl}-amide, 4-{2-[4-(2-Ethyl-5,7-dimethyl-pyrazolo[1,5-a]pyrimidin-3-ylmethyl)-phenoxy]-ethyl}-piperidin-4-ol, 2-Ethyl-5,7-dimethyl-3-[4-(2-piperazin-1-yl-ethoxy)-benzyl]-pyrazolo[1,5-a]pyrimidine, 4-{2-[4-(2-Ethyl-5,7-dimethyl-pyrazolo[1,5-a]pyrimidin-3-ylmethyl)-phenoxy]-ethyl}-piperazine-1-carboxylic acid tert-butyl ester, 2-Ethyl-3-{4-[2-((R)-3-methoxymethyl-piperazin-1-yl)-ethoxy]-benzyl}-5,7-dimethyl -pyrazolo[1,5-a]pyrimidine, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ol, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ylamine, 1-{1-[4-(2-Ethyl-5,7-dimethyl-pyrazolo[1,5-a]pyrimidin-3-ylmethyl)-phenyl]-1H-pyrazol-4-ylmethyl}-piperidin-4-ylamine, 2-Ethyl-5,7-dimethyl-3-[4-(4-piperazin-1-ylmethyl-pyrazol-1-yl)-benzyl]-pyrazolo[1,5-a]pyrimidine, ((R)-4-{1-[4-(2-Ethyl-5,7-dimethyl-pyrazolo[1,5-a]pyrimidin-3-ylmethyl)-phenyl]-1H-pyrazol-4-ylmethyl}-piperazin-2-yl)-methanol, 2-Ethyl-5,7-dimethyl-3-[4-(4-piperazin-1-ylmethyl-[1,2,3]triazol-1-yl)-benzyl]-pyrazolo[1,5-a]pyrimidine, 4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol, 4-{1-[4-(2-Ethyl-5,7-dimethyl-pyrazolo[1,5-a]pyrimidin-3-ylmethyl)-phenyl]-1H-[1,2,3]triazol-4-ylmethyl}-4-hydroxy-piperidine-1-carboxylic acid tert-butyl ester, 2-Ethyl-5,7-dimethyl-3-[4-(5-piperidin-4-yl-[1,3,4]oxadiazol-2-yl)-benzyl]-pyrazolo[1,5-a]pyrimidine, 4-{N'-[4-(2-Ethyl-5,7-dimethyl-pyrazolo[1,5-a]pyrimidin-3-ylmethyl)-benzoyl]-hydrazinocarbonyl}-piperidine-1-carboxylic acid tert-butyl ester, 4-{5-[4-(2-Ethyl-5,7-dimethyl-pyrazolo[1,5-a]pyrimidin-3-ylmethyl)-phenyl]-[1,3,4]oxadiazol-2-yl}-cyclohexylamine, 4-{N'-[4-(2-Ethyl-5,7-dimethyl-pyrazolo[1,5-a]pyrimidin-3-ylmethyl)-benzoyl]-hydrazinocarbonyl}-cyclohexyl)-carbamic acid tert-butyl ester, 4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-ol, 1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-2-methylamino-ethanone, and (S)-1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-3-hydroxy-2-methylamino-propan-1-one.

Embodiment eleven relates to a compound in accordance to any one of the preceding embodiments, or a pharmaceutically acceptable salt thereof, for use as a medicament, in particular for use in the treatment of a GPR4 susceptible disease or disorder.

Embodiment twelve relates to a method for treating a patient susceptible to GPR4 modulation comprising administering an effective amount of a compound of any of the preceding embodiments, or a pharmaceutically acceptable salt thereof, thereby treating a disease or condition being selected from:

Osteoporosis (juvenile, menopausal, post-menopausal, post-traumatic, caused by old age or corticosteroid therapy or inactivity), gingivitis, periodontitis, Paget's disease, hypercalcemia of malignancy, tumor induced hypercalcemia, metabolic bone disease, cancer, solid tumors, cardiovascular disorders, atherosclerose, myocardial infarction, limb diseases, peripheral arterial occlusive disease, eye diseases, diabetic retinopathy, macular degeneration, uveitis, arthritis, rheumatoid arthritis, osteoarthritis wound healing, skin diseases, inflammatory and obstructive airway diseases, asthma, intrinsic and extrinsic asthma, mild asthma, moderate asthma, severe asthma, bronchitic asthma, exercise induced asthma, occupational asthma and asthma induced following bacterial infection, acute lung injury, acute/adult respiratory distress syndrome, chronic obstructive pulmonary airways or lung diseases, chronic bronchitis, dyspnea associated herewith, emphysema, exacerbation of airways hyperactivity consequent to other drug therapy, bronchitis, acute arachidic, catarrhal, croupus, chronic or phthinoid bronchitis. Pneumoconiosis, aluminosis, anthracosis, asbestosis, chlicosis, ptilosis, siderosis, silicosis, tabacosis byssinosis, eosinophilia, bronchopulmonar aspergillosis, polyarteritis nodosa, eosinophilic granuloma and eosinophil-related disorders affecting the airways occasioned by drug reaction, infections by organisms such as *pneumocystis carinii, trypanosoma cruzi, trypanosoma brucei*, crithidia fusculata, parasitic diseases such as schistosomiasis and malaria, tumor invasion and metastasis, metachromatic leukodystrophy, muscular dystrophy, amythrophy, autoimmune disease, respiratory disease, immunologically mediated disease, transplant rejection, inflammatory pain, visceral pain, chronic pain, tumor pain, renal tubular acidosis, Crohn's disease, and inflammatory bowel disease.

Embodiment thirteen relates to a pharmaceutical composition comprising a compound of any one of the preceding embodiments, or a pharmaceutically acceptable salt thereof, together with a pharmaceutically acceptable carrier.

Embodiment fourteen relates to a combination, e.g. a pharmaceutical combination or a kit, comprising a) a first agent which is a compound of any one or the preceding embodiments, or a salt thereof, in particular a pharmaceutically acceptable salt thereof, and b) at least one co-agent, e.g. an immunosuppressant, immunomodulatory, anti-inflammatory, chemotherapeutic or anti-infectious agent.

Embodiment fifteen relates to a process for synthesizing a compound of formula (II), (III), (IV), or (V) as defined in embodiments 3, 4, 5, or 6, comprising the steps of:

(a) reacting a 4-bromo-phenyl propionitrile optionally substituted by R4 with an ester $R1COOC_{1-6}$alkyl e.g. in the presence of a base, e.g. sodium t-butylate, potassium t-pentylate or the like and a solvent e.g. THF, to form intermediate (1), which is reacted with hydrazine, for example under heat to form the aminopyrazole intermediate (2), which is reacted with an appropriately substituted diketone as shown in the below scheme to form intermediate (3);

which intermediate (3) may conveniently be reacted with a compound of formula $CH_2=CH-(CH_2)_x-R$ and optionally in the presence of a catalyst, e.g. $Pd(t-Bu_3P)_2$, to form the compounds of the invention, e.g. a compound in accordance to general formula (III), carrying for example a central triazolo-, oxadiazolo-, imidazo methylene-, vinyl-, or allyl-linker (for x=1); wherein x is 0 or 1, and wherein the other variables are as defined in the embodiments 3, 4, 5 and 6;

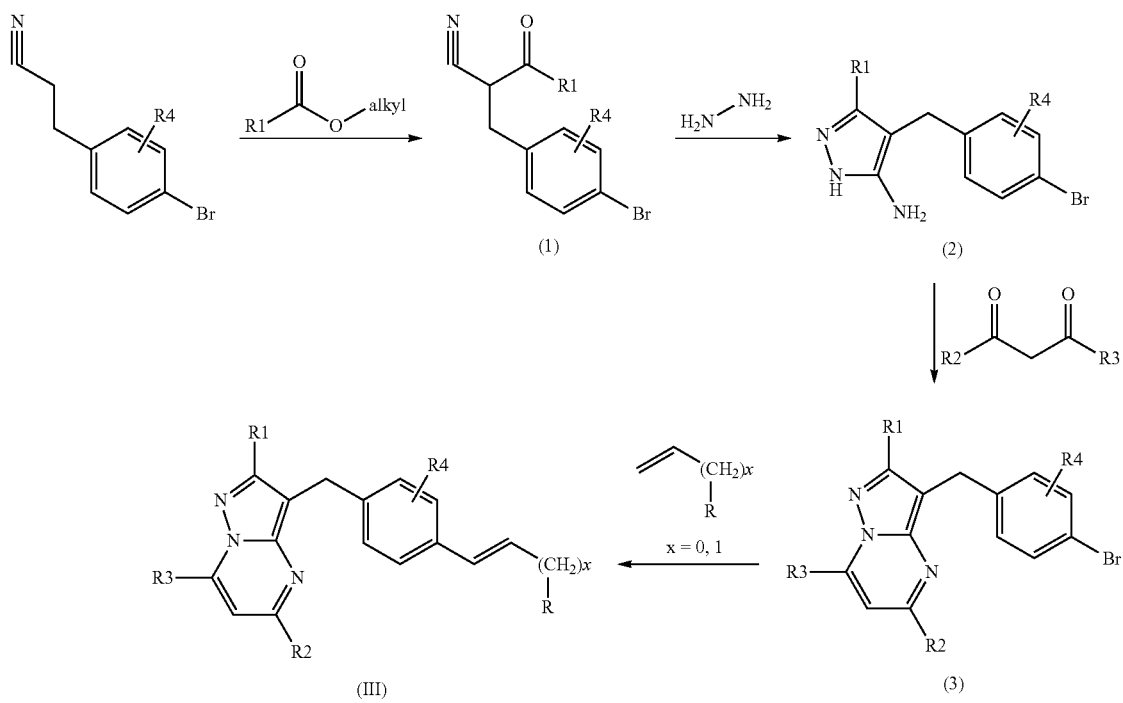

or, (b) reacting a compound of general formula (III) for example with hydrogen e.g. in the absence or presence of a catalyst to yield a compound of general formula (V), wherein the variables are as provided in the above paragraph;

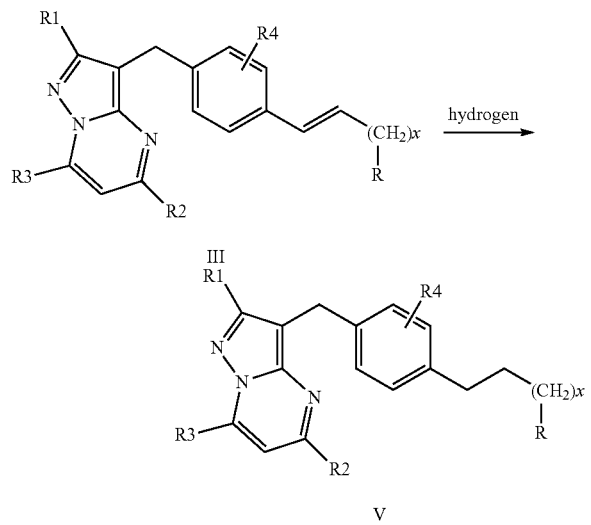

or (c) intermediate (3) may also be reacted for example in 4 steps; (i) with diphenylmethanimine in the presence of a base such as sodium t-butoxide, thereupon (ii) with conc. HCl to furnish the primary amine, which (iii) may be reacted e.g. with isopentylnitrite to yield the diazonium salt, which (iv) may be reacted e.g. with tin(II)chloride in a strong acid, e.g. HCl, to yield the hydrazine intermediate (15) (see scheme below), which intermediate (15) may be reacted e.g. with an acrylate such as (E)-ethyl 2-cyano-3-ethoxyacrylate to form an imidazole intermediate (16), which is then reacted e.g. with isoamylnitrite to form intermediate (17) which may be reacted e.g. with DIBAH and manganese dioxide to yield aldehyde intermediate (19) as shown in reaction scheme 4, which aldehyde (19) is reacted for example under reductive amination conditions (e.g. in accordance to reaction scheme 20) with the free amino group e.g. of a piperidine-, piperazine-, pyrrolidine-, or an azetidine-derivative to yield a compound in accordance to general formula (IV);

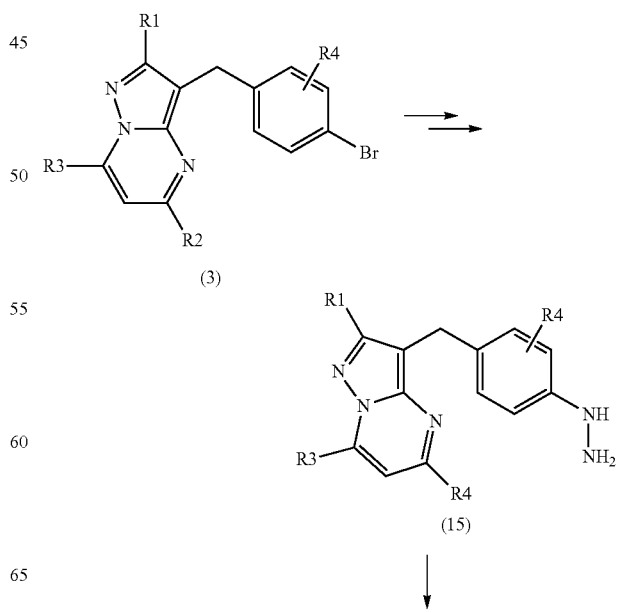

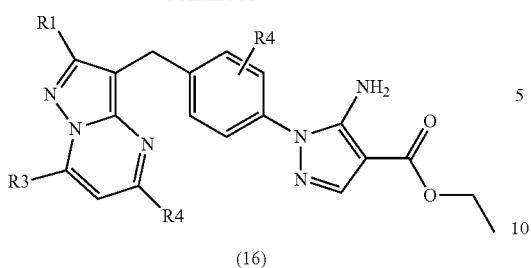

(16)

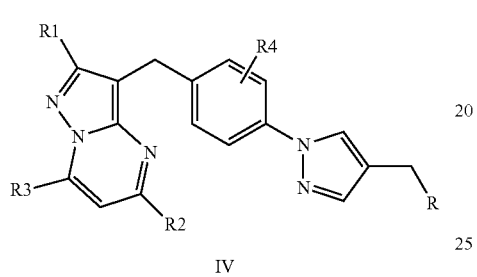

IV or (d) reacting cyanoketone (23) with an optionally substituted cyanobenzaldehyde under standard condensation reaction conditions, e.g. sodium hydroxide in methanol to yield the nitrile (24), which upon hydrogenation reaction yields ketonitrile (25), which is reacted with the appropriate diketone R2-CO—CH$_2$—CO—R3 to furnish the ring-closed intermediate (27), which may be conveniently converted to hydrazide derivative (29);

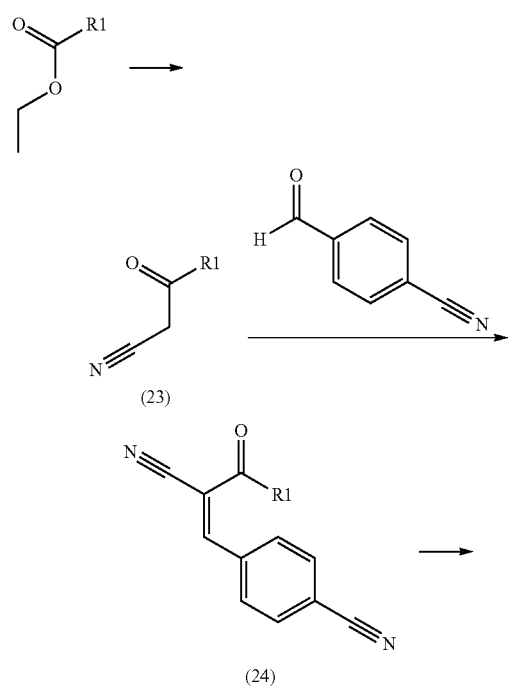

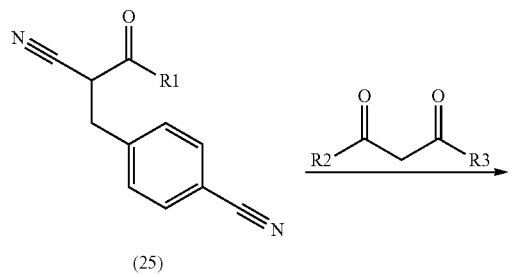

(25)

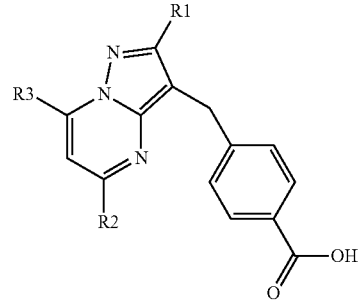

(27)

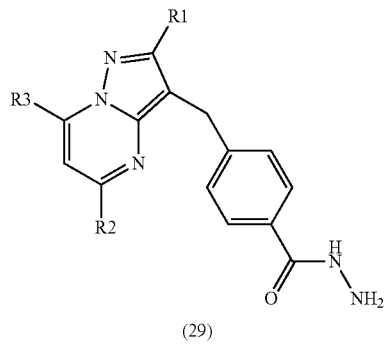

(29)

whereupon intermediate (29) is reacted with a carboxylic acid in accordance to the formula RCOOH, wherein R stands for the definitions of claim 1, e.g. under peptide coupling conditions, e.g. with HOBT/EDC, to furnish the coupled hydrazone, which is then reacted for example with tosylchloride e.g. in the presence of an organic base to render the ring closed compound, i.e. the oxadiazole compound of the invention in accordance to general formula II.

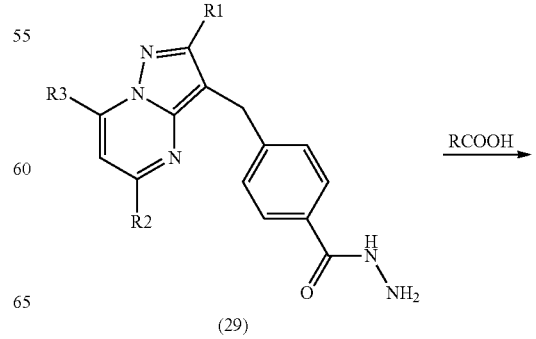

(29)

-continued

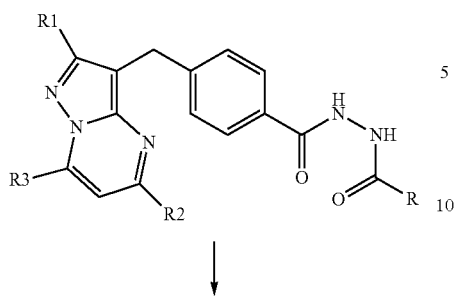

Embodiment sixteen relates to a process for synthesizing a compound of formula (II),

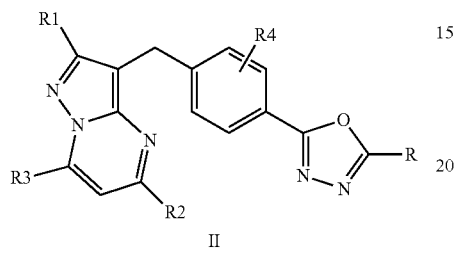

wherein

R1 is H or $C_1$-$C_6$ alkyl;

R2 and R3 are independently from each other H or $C_1$-$C_6$ alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$ alkyl optionally substituted one or more times by hydroxy, oxo (=O), amino optionally substituted by $C_1$-$C_6$ alkoxycarbonyl, mono $C_1$-$C_6$ alkyl-amino optionally substituted by $C_1$-$C_6$ alkoxycarbonyl, di-$C_1$-$C_6$ alkyl-amino, $C_1$-$C_6$ alkoxy, $C_1$-$C_6$ alkoxycarbonyl or tri-$C_1$-$C_6$ alkyl silyloxy; tetrazole optionally substituted by $C_1$-$C_6$ alkyl; a hydroxypyrrolidine-carbonyl group; a hydroxypyrrolidine-aminocarbonyl group or a hydroxypyrrolidine-carbonylamino group; and R4 is H, $C_1$-$C_6$ alkyl, $C_1$-$C_6$ alkoxy, halogen, hydroxy, cyano or trifluoromethyl;

Or to a process for synthesizing a compound of formula (III)

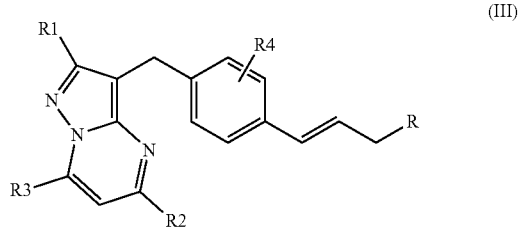

wherein the variables are as defined above, or to a process for synthesizing a compound of formula (IV),

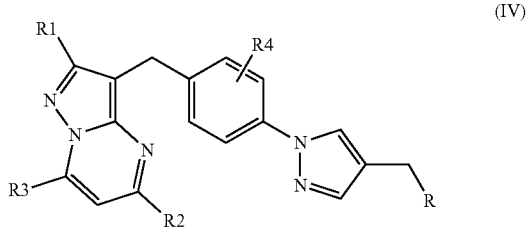

wherein the variables are as defined above, or to a process for synthesizing a compound of formula (V)

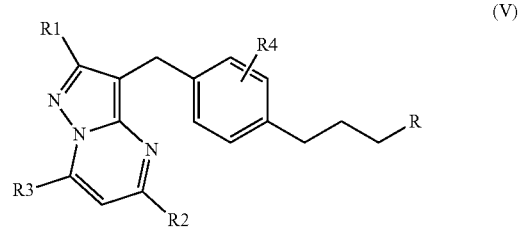

wherein the variables are as defined above;

comprising the steps of:

(a) reacting a 4-bromo-phenyl propionitrile optionally substituted by R4 with an ester R1COOC$_{1-6}$ alkyl in the presence of a base, e.g. sodium t-butylate, potassium t-pentylate or the like and a solvent e.g. THF, to form intermediate (1), which is reacted with hydrazine, for example under heat to form the aminopyrazole intermediate (2), which is reacted with an appropriately substituted diketone as shown in the below scheme to form intermediate (3);

which intermediate (3) may conveniently be reacted with a compound of formula $CH_2$=CH—$(CH_2)_x$—R and optionally in the presence of a catalyst, e.g. Pd(t-Bu$_3$P)$_2$, to form e.g. a compound in accordance to general formula (III), carrying for example a central triazolo-, oxadiazolo-, imidazo methylene-, vinyl-, or allyl-linker (for x=1); wherein x is 0 or 1, and wherein the other variables are as defined in the claims 3, 4, 5 or 6;

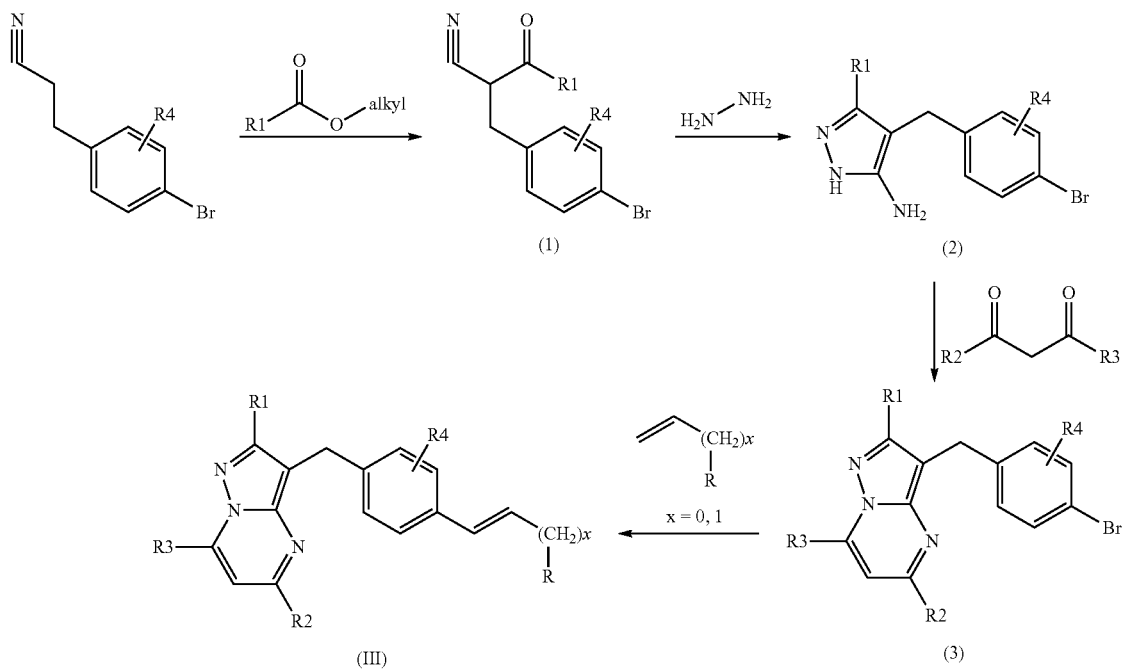

(1)   (2)   (3)

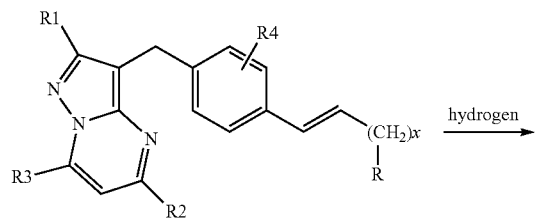

(III)

or (b) reacting a compound of general formula (III) for example with hydrogen e.g. in the absence or presence of a catalyst to yield a compound of general formula (V), wherein the variables are as provided in the above paragraph;

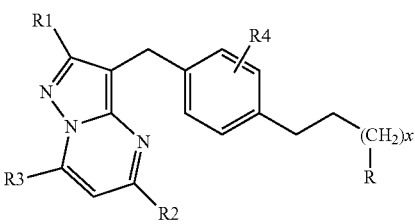

III hydrogen →

V or (c) intermediate (3) may also be reacted for example in 4 steps; (i) with diphenylmethanimine in the presence of a base such as sodium t-butoxide, thereupon (ii) with conc. HCl to furnish the primary amine, which (iii) may be reacted e.g. with isopentylnitrite to yield the diazonium salt, which (iv) may be reacted e.g. with tin(II)chloride in a strong acid, e.g. HCl, to yield the hydrazine intermediate (15) (see scheme below), which intermediate (15) may be reacted e.g. with an acrylate such as (E)-ethyl 2-cyano-3-ethoxyacrylate to form an imidazole intermediate (16), which is then reacted e.g. with isoamylnitrite to form intermediate (17) which may be reacted e.g. with DIBAH and manganese dioxide to yield aldehyde intermediate (19) as shown in reaction scheme 4, which aldehyde (19) is reacted for example under reductive amination conditions (e.g. in accordance to reaction scheme 20) with the free amino group e.g. of a piperidine-, piperazine-, pyrrolidine-, or an azetidine-derivative to yield a compound in accordance to general formula (IV);

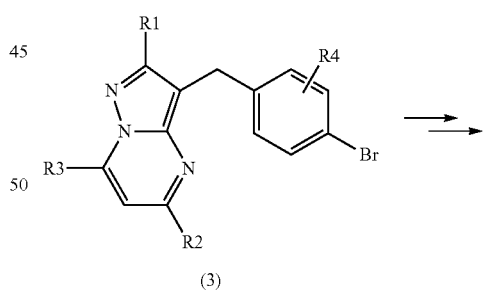

(3)

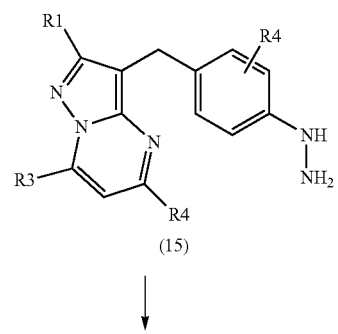

(15)

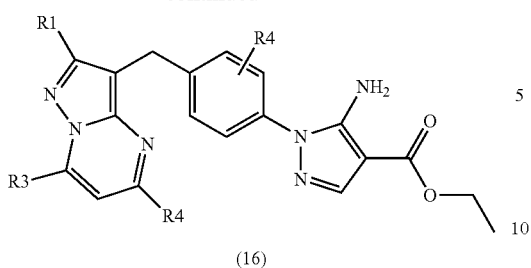

(16)

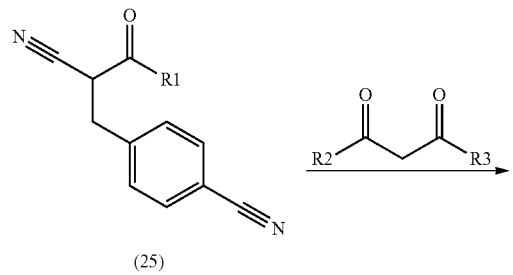

(25)

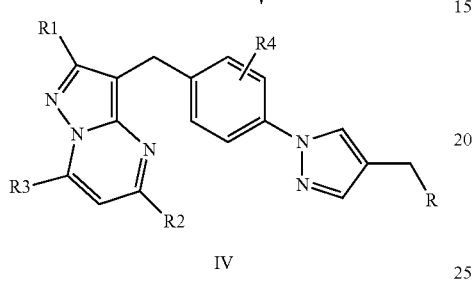

IV

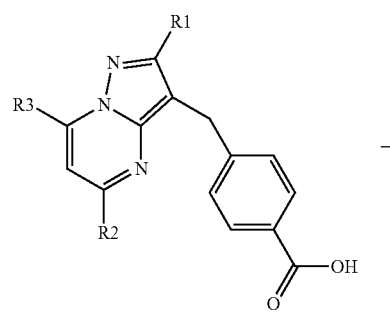

(27)

or (d) reacting cyanoketone (23) with an optionally substituted cyanobenzaldehyde under standard condensation reaction conditions, e.g. sodium hydroxide in methanol to yield the nitrile (24), which upon hydrogenation reaction yields ketonitrile (25), which is reacted with the appropriate diketone R2—CO—CH$_2$—CO—R3 to furnish the ring-closed intermediate (27), which may be conveniently converted to hydrazide derivative (29);

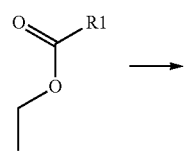

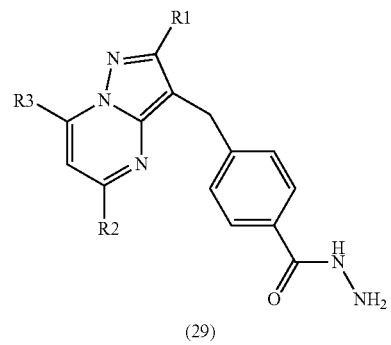

(29)

whereupon intermediate (29) is reacted with a carboxylic acid in accordance to the formula RCOOH, wherein R stands for the definitions of claim 1, e.g. under peptide coupling conditions, e.g. with HOBT/EDC, to furnish the coupled hydrazone, which is then reacted for example with tosylchloride e.g. in the presence of an organic base to render the ring closed compound, i.e. the oxadiazole compound of the invention in accordance to general formula II.

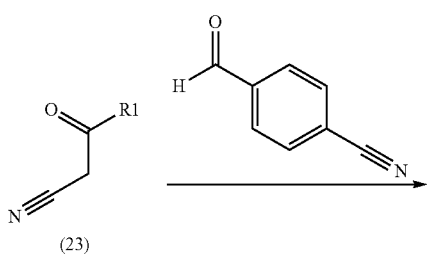

(23)

(24)

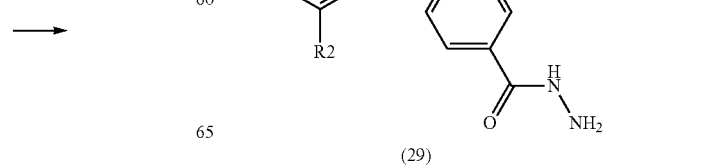

(29)

-continued

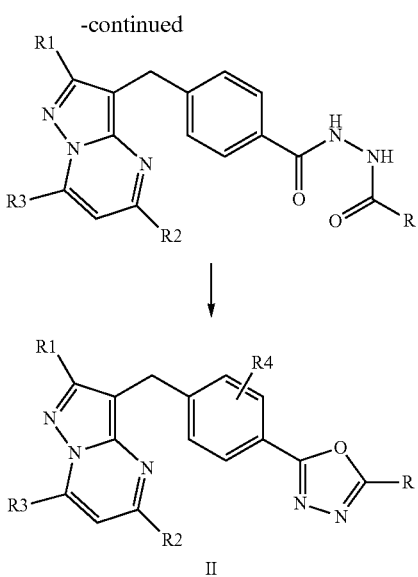

II

What is claimed is:
1. A compound of formula (I) or a pharmaceutically acceptable salt thereof,

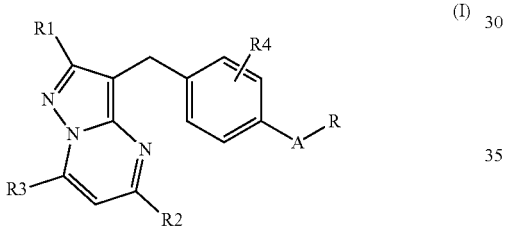

wherein
R1 is H or $C_1$-$C_6$alkyl;
R2 and R3 are independently from each other H or $C_1$-$C_6$alkyl;
A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—,

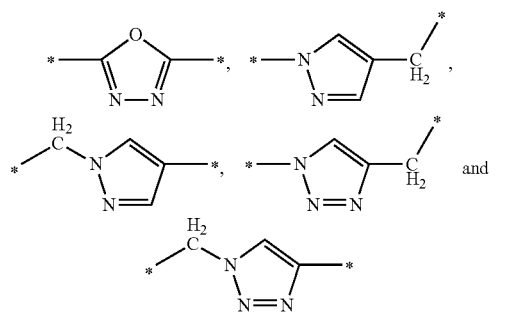

(wherein a* denote the link (or places of attachment));

R stands for heterocyclyl or cycloalkyl, each of which may be optionally substituted 1 to 4 times; and
R4 is H, $C_1$-$C_6$alkyl, $C_1$-$C_6$alkoxy, halogen, hydroxy, cyano or trifluoromethyl.

2. A compound of claim 1, which is a compound of formula (I') or a pharmaceutically acceptable salt thereof,

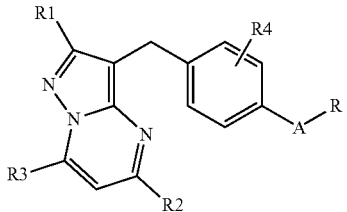

wherein
R1 is H or $C_1$-$C_6$alkyl;
R2 and R3 are independently from each other H or $C_1$-$C_6$alkyl;
A is a bivalent linking group selected from the group consisting of:
—CH=CH—, —CH=CH—CH$_2$—, —CH$_2$—CH=CH—, —CH$_2$—CH$_2$—CH$_2$—, —CH=CH—C(O)—, —C(O)—CH=CH—, —CH$_2$—CH$_2$—C(O)—, —C(O)—CH$_2$—CH$_2$—, —C(O)—NH—CH$_2$—, —CH$_2$—NH—C(O)—, —O—CH$_2$—, —CH$_2$—O—, —O—CH$_2$—CH$_2$—, —CH$_2$—CH$_2$—O—, (wherein a * denote the link (or places of attachment));
R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkyl-amino optionally substituted by $C_1$-$C_6$alkoxycarbonyl, di-$C_1$-$C_6$alkyl-amino, $C_1$-$C_6$alkoxy, $C_1$-$C_6$alkoxycarbonyl or tri-$C_1$-$C_6$alkyl silyloxy; tetrazole optionally substituted by $C_1$-$C_6$alkyl; a hydroxypyrrolidine- Carbonyl group;
a hydroxypyrrolidine-aminocarbonyl group or a hydroxypyrrolidine-Carbonylamino group; and
R4 is H, $C_1$-$C_6$alkyl, $C_1$-$C_6$alkoxy, halogen, hydroxy, cyano or trifluoromethyl.

3. A compound of claim 1, which is a compound of formula (I") or a pharmaceutically acceptable salt thereof,

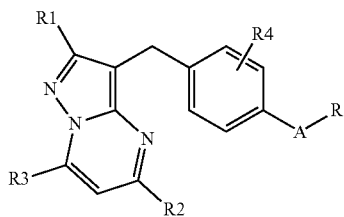

wherein
R1 is H or $C_1$-$C_6$alkyl;
R2 and R3 are independently from each other H or $C_1$-$C_6$alkyl;
A is a bivalent linking group selected from the group consisting of:
—CH=CH—, —CH=CH—CH$_2$—, —CH$_2$—CH$_2$—CH$_2$—, —CH=CH—C(O)—, —CH$_2$—CH$_2$—C(O)—, —C(O)—NH—CH$_2$—, —O—CH$_2$—, —O—CH$_2$—CH$_2$—,

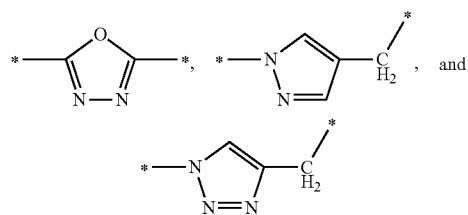

(wherein a * denote the link (or places of attachment));
R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkyl-amino optionally substituted by $C_1$-$C_6$alkoxycarbonyl, di-$C_1$-$C_6$alkyl-amino, $C_1$-$C_6$alkoxy, $C_1$-$C_6$alkoxycarbonyl or tri-$C_1$-$C_6$alkyl silyloxy; tetrazole optionally substituted by $C_1$-$C_6$alkyl; a hydroxypyrrolidine-Carbonyl group;
a hydroxypyrrolidine-aminocarbonyl group or a hydroxypyrrolidine-Carbonylamino group; and
R4 is H or $C_1$-$C_6$alkyl.
4. A compound according to claim 1, which is a compound of formula (II) or a pharmaceutically acceptable salt thereof,

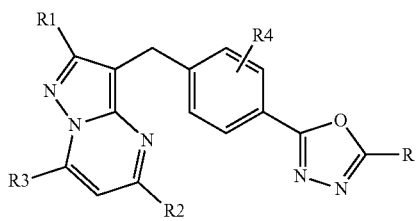

wherein
R1 is H or $C_1$-$C_6$alkyl;
R2 and R3 are independently from each other H or $C_1$-$C_6$alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkyl-amino optionally substituted by $C_1$-$C_6$alkoxycarbonyl, di-$C_1$-$C_6$alkyl-amino, $C_1$-$C_6$alkoxy, or $C_1$-$C_6$alkoxycarbonyl; tetrazole optionally substituted by $C_1$-$C_6$alkyl; a hydroxypyrrolidine-Carbonyl group; a hydroxypyrrolidine-aminocarbonyl group or a hydroxypyrrolidine-carbonylamino group; and
R4 is H or $C_1$-$C_6$alkyl.
5. A compound according to claim 1, which is a compound of formula (III) or a pharmaceutically acceptable salt thereof,

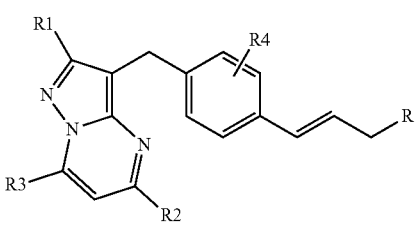

wherein
R1 is H or $C_1$-$C_6$alkyl;
R2 and R3 are independently from each other H or $C_1$-$C_6$alkyl;
R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkyl-amino optionally substituted by $C_1$-$C_6$alkoxycarbonyl, di-$C_1$-$C_6$alkyl-amino, $C_1$-$C_6$alkoxy, or $C_1$-$C_6$alkoxycarbonyl; tetrazole optionally substituted by $C_1$-$C_6$alkyl; a hydroxypyrrolidine-carbonyl group; a hydroxypyrrolidine-aminocarbonyl group or a hydroxypyrrolidine-Carbonylamino group; and
R4 is H or $C_1$-$C_6$alkyl.
6. A compound according to claim 1, which is a compound of formula (IV) or a pharmaceutically acceptable salt thereof,

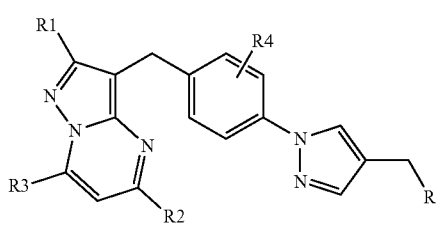

wherein
R1 is H or $C_1$-$C_6$alkyl;
R2 and R3 are independently from each other H or $C_1$-$C_6$alkyl;
R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkylamino optionally substituted by $C_1$-$C_6$alkoxycarbonyl, di-$C_1$-$C_6$alkyl-amino, $C_1$-$C_6$alkoxy, or $C_1$-$C_6$alkoxycarbonyl; tetrazole optionally substituted by $C_1$-$C_6$alkyl; a hydroxypyrrolidine-carbonyl group; a hydroxypyrrolidine-aminocarbonyl group or a hydroxypyrrolidine-carbonylamino group; and R4 is H or $C_1$-$C_6$alkyl.

7. A compound according to claim 1, which is a compound of formula (V) or a pharmaceutically acceptable salt thereof,

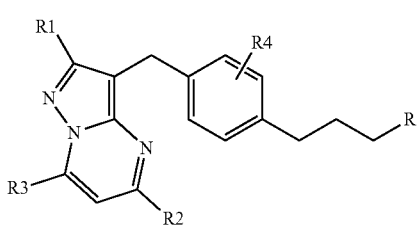

wherein

R1 is H or $C_1$-$C_6$alkyl;

R2 and R3 are independently from each other H or $C_1$-$C_6$alkyl;

R stands for azetidine, pyrrolidine, piperidine, piperazine, cyclohexane or cyclopentane, each of which may be optionally substituted 1 to 4 times by oxo (=O); hydroxy; $C_1$-$C_6$alkyl optionally substituted one or more times by hydroxy, oxo(=O), amino optionally substituted by $C_1$-$C_6$alkoxycarbonyl, mono $C_1$-$C_6$alkylamino optionally substituted by $C_1$-$C_6$alkoxycarbonyl, di-$C_1$-$C_6$alkyl-amino, $C_1$-$C_6$alkoxy, or $C_1$-$C_6$alkoxycarbonyl; tetrazole optionally substituted by $C_1$-$C_6$alkyl; a hydroxypyrrolidine-Carbonyl group; a hydroxypyrrolidine-aminocarbonyl group or a hydroxypyrrolidine-Carbonylamino group; and R4 is H or $C_1$-$C_6$alkyl.

8. A compound of claim 1, or a pharmaceutically acceptable salt thereof, wherein R1 is $C_1$-$C_2$alkyl;

R2 and R3 are independently from each other methyl;

R stands for piperidine or piperazine which may be optionally substituted 1 to 2 times by $C_1$-$C_6$alkyl optionally substituted one or more times by hydroxy, oxo(=O), amino optionally substituted by $C_1$-$C_6$alkoxycarbonyl, or mono $C_1$-$C_6$alkyl-amino optionally substituted by $C_1$-$C_6$alkoxycarbonyl; and R4 is H.

9. A compound of claim 1, or a pharmaceutically acceptable salt thereof, wherein R1 is ethyl;

R2 and R3 are independently from each other methyl;

R stands for 4-piperidinyl or 1-piperazinyl which may be optionally substituted 1 to 2 times by $C_1$-$C_6$alkyl optionally substituted 1 - 3 times by hydroxy, oxo(=O), or mono $C_1$-$C_6$alkyl-amino, with the proviso that the substituent $C_1$-$C_6$alkyl cannot be unsubsituted when $C_1$-$C_6$alkyl is attached to a N-atom; and R4 is H.

10. A compound of claim 1, or a pharmaceutically acceptable salt thereof, wherein the compound is selected from:

4-{(E)-2-[4-(2-Ethyl-5,7-dimethyl-pyrazolo[1,5-a]pyrimidin-3-ylmethyl)-phenyl]-vinyl}-piperidin-4-Ol, 4-{(E)-2-[4-(2-Ethyl-5,7-dimethyl-pyrazolo[1,5-a]pyrimidin-3-ylmethyl)-phenyl]-vinyl}-4-hydroxy-piperidine-1-Carboxylic acid tert-butyl ester, 3-{(E)-3-[4-(2-Ethyl-5,7-dimethyl-pyrazolo[1,5-a]pyrimidin-3-ylmethyl)-phenyl]-allyl}-azetidin-3-Ol, 3-{(E)-3-[4-(2-Ethyl-5,7-dimethyl-pyrazolo[1,5-a]pyrimidin-3-ylmethyl)-phenyl]-allyl}-3-hydroxy-azetidine-1-Carboxylic acid tert-butyl ester, 4-{(E)-3-[4-(2-Ethyl-5,7-dimethyl-pyrazolo[1,5-a]pyrimidin-3-ylmethyl)-phenyl]-allyl}-piperidin-4-Ol, 4-{(E)-3-[4-(2-Ethyl-5,7-dimethyl-pyrazolo[1,5-a]pyrimidin-3-ylmethyl)-phenyl]-allyl}-4-hydroxy-piperidine-1-Carboxylic acid tert-butyl ester, 4-{3-[4-(2-Ethyl-5,7-dimethyl-pyrazolo[1,5-a]pyrimidin-3-ylmethyl)-phenyl]-propyl}-piperidin-4-Ol, 4-{3-[4-(2-Ethyl-5,7-dimethyl-pyrazolo[1,5-a]pyrimidin-3-ylmethyl)-phenyl]-propyl}-4-hydroxy-piperidine-1-Carboxylic acid tert-butyl ester, (2S,4S)-4-{(E)-3-[4-(2-Ethyl-5,7-dimethyl-pyrazolo[1,5-a]pyrimidin-3-ylmethyl)-phenyl]-allyl}-2-methyl-piperidin-4-Ol, 1-{(E)-3-[4-(2-Ethyl-5,7-dimethyl-pyrazolo[1,5-a]pyrimidin-3-ylmethyl)-phenyl]-allyl}-piperazin-2-One, (R)-3-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-propane-1,2-diol, 1-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-methylamino-ethanone,

[2-(4-{(E)-3-[4-(2-Ethyl-5,7-dimethyl-pyrazolo[1,5-a]pyrimidin-3-ylmethyl)-phenyl]-allyl}-4-hydroxy-piperidin-1-yl)-2-Oxo-ethyl]-methyl-Carbamic acid tert-butyl ester, ((S)-4-{(E)-3-[4-(2-Ethyl-5,7-dimethyl-pyrazolo[1,5-a]pyrimidin-3-ylmethyl)-phenyl]-allyl}-piperazin-2-yl)-methanol, (S)-4-{(E)-3-[4-(2-Ethyl-5,7-dimethyl-pyrazolo[1,5-a]pyrimidin-3-ylmethyl)-phenyl]-allyl}-2-hydroxymethyl-piperazine-1-Carboxylic acid tert-butyl ester, 2-Ethyl-5,7-dimethyl-3-{4-[(E)-3-((S)-3-methyl-piperazin-1-yl)-propenyl]-benzyl}-pyrazolo[1,5-a]pyrimidine, 2-Ethyl-3-{4-[(E)-3-((S)-3-methoxymethyl-piperazin-1-yl)-propenyl]-benzyl}-5,7-dimethyl-pyrazolo[1,5-a]pyrimidine, 2-Amino-1-(4-{(E)-3-[4-(2-ethyl-5,7-dimethyl-pyrazolo[1,5-a]pyrimidin-3-ylmethyl)-phenyl]-allyl}-piperazin-1-yl)-ethanone, 2-Ethyl-5,7-dimethyl-3-(4-{(E)-3-[4-(1-methyl-1H-tetrazol-5-yl)-piperidin-1-yl]-propenyl}-benzyl)-pyrazolo[1,5-a]pyrimidine, ((S)-4-{(E)-3-[4-(2-Ethyl-5,7-dimethyl-pyrazolo[1,5-a]pyrimidin-3-ylmethyl)-phenyl]-allyl}-piperazin-2-ylmethyl)-dimethyl-amine, (R)-2-Dimethylcarbamoyl-4-{(E)-3-[4-(2-ethyl-5,7-dimethyl-pyrazolo[1,5-a]pyrimidin-3-ylmethyl)-phenyl]-allyl}-piperazine-1-Carboxylic acid tert-butyl ester, (S)-2-Dimethylaminomethyl-4-{(E)-3-[4-(2-ethyl-5,7-dimethyl-pyrazolo[1,5-a]pyrimidin-3-ylmethyl)-phenyl]-allyl}-piperazine-1-Carboxylic acid tert-butyl ester, 2-Ethyl-5,7-dimethyl-3-[4-((E)-3-piperazin-1-yl-propenyl)-benzyl]-pyrazolo[1,5-a]pyrimidine, (S)-1-(4-{(E)-3-[4-(2-Ethyl-5,7-dimethyl-pyrazolo[1,5-a]pyrimidin-3-ylmethyl)-phenyl]-allyl}-piperazin-1-yl)-3-hydroxy-2-methylamino-propan-1-One, (4-{(E)-3-[4-(2-Ethyl-5,7-dimethyl-pyrazolo[1,5-a]pyrimidin-3-ylmethyl)-phenyl]-allyl}-piperazin-1-yl)-((2S,3R)-3-hydroxy-pyrrolidin-2-yl)-methanone, (R)-3-(4-{(E)-3-[4-(2-Ethyl-5,7-dimethyl-pyrazolo[1,5-a]pyrimidin-3-ylmethyl)-phenyl]-allyl}-piperazin-1-yl)-propane-1,2-diol, (R)-1-(tert-Butyl-dimethyl-silanyloxy)-3-(4-{(E)-3-[4-(2-ethyl-5,7-dimethyl-pyrazazolo[1,5-]pyrimidin-3-ylmethyl)-phenyl]-allyl}-piperazin-1-yl)-propan-2-Ol, (E)-3-[4-(2-Ethyl-5,7-dimethyl-pyrazolo[1,5-a]pyrimidin-3-ylmethyl)-phenyl]-1-piperazin-1-yl-propenone, 4-{(E)-3-[4-(2-Ethyl-5,7-dimethyl-pyrazolo[1,5-a]pyrimidin-3-ylmethyl)-phenyl]-acryloyl}-piperazine-1-Carboxylic acid tert-butyl ester, 3-[4-(2-Ethyl-5,7-dimethyl-pyrazolo[1,5-a]pyrimidin-3-ylmethyl)-phenyl]-1-piperazin-1-yl-propan-1-One, 4-{3-[4-(2-Ethyl-5,7-dimethyl-pyrazolo[1,5-a]pyrimidin-3-ylmethyl)-phenyl]-propionyl}-piperazine-1-Carboxylic acid tert-butyl ester, 4-(2-Ethyl-5,7-dimethyl-pyrazolo[1,5-a]pyrimidin-3-ylmethyl)-N-piperidin-4-ylmethyl-benzamide, 2-Ethyl-5,7-dimethyl-3-[4-(piperidin-4-ylmethoxy)-benzyl]-pyrazolo[1,5-a]pyrimidine, 4-[4-(2-Ethyl-5,7-dimethyl-pyrazolo[1,5-a]pyrimidin-3-ylmethyl)-phenoxymethyl]-piperidine-1-Carboxylic acid tert-butyl ester, {4-[4-(2-Ethyl-5,7-dimethyl-pyrazolo[1,5-a]pyrimidin-3-ylmethyl)-phenoxymethyl]-piperidin-1-yl}-((2S,3R)-3-hydroxy-pyrrolidin-2-yl)-methanone, 4-[4-(2-Ethyl-5,7-dimethyl-pyrazolo[1,5-a]pyrimidin-3-ylmethyl)-phenoxymethyl]-Cyclohexylamine, (2S,3R)-3-Hydroxy-pyrrolidine-2-Carboxylic acid {4-[4-(2-ethyl-5,7-dimethyl-pyrazolo[1,5-a]pyrimidin-3-ylmethyl)-phenoxymethyl]-Cyclohexyl}-amide, 4-{2-[4-(2-Ethyl-5,7-dimethyl-pyrazolo[1,5-a]pyrimidin-3-ylmethyl)-phenoxy]-ethyl}-piperidin-4-Ol, 2-Ethyl-5,7-dimethyl-3-[4-(2-piperazin-1-yl-ethoxy)-benzyl]-pyrazolo[1,5-a]pyrimidine, 4-{2-[4-(2-Ethyl-5,7-dimethyl-pyrazolo[1,5-a]pyrimidin-3-ylmethyl)-phenoxy]-ethyl}-piperazine-1-Carboxylic acid tert-butyl ester, 2-Ethyl-3-{4-[2-((R)-3-methoxymethyl-piperazin-1-yl)-ethoxy]-benzyl}-5,7-dimethyl-pyrazolo[1,5-a]pyrimidine, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-Ol, 1-{1-[4-(2-Ethyl-5,7-dimethyl-pyrazolo[1,5-a]pyrimidin-3-ylmethyl)-phenyl]-1H-pyrazol-4-ylmethyl}-azetidin-3-ylamine, 1-{1-[4-(2-Ethyl-5,7-dimethyl-pyrazolo[1,5-a]pyrimidin-3-ylmethyl)-phenyl]-1H-pyrazol-4-ylmethyl}-piperidin-4-ylamine, 2-Ethyl-5,7-dimethyl-3-[4-(4-piperazin-1-ylmethyl-pyrazol-1-yl)-benzyl]-pyrazolo[1,5-a]pyrimidine, ((R)-4-{1-[4-(2-Ethyl-5,7-dimethyl-pyrazolo[1,5-a]pyrimidin-3-ylmethyl)-phenyl]-1H-pyrazol-4-ylmethyl}-piperazin-2-yl)-methanol, 2-Ethyl-5,7-dimethyl-3-[4-(4-piperazin-1-ylmethyl-[1,2,3]triazol-1-yl)-benzyl]-pyrazolo[1,5-a]pyrimidine, 4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-Ol, 4-{1-[4-(2-Ethyl-5,7-dimethyl-pyrazolo[1,5-a]pyrimidin-3-ylmethyl)-phenyl]-1H-[1,2,3]triazol-4-ylmethyl}-4-hydroxy-piperidine-1-Carboxylic acid tert-butyl ester, 2-Ethyl-5,7-dimethyl-3-[4-(5-piperidin-4-yl-[1,3,4]oxadiazol-2-yl)-benzyl]-pyrazolo[1,5-a]pyrimidine, 4-{N'-[4-(2-Ethyl-5,7-dimethyl-pyrazolo[1,5-a]pyrimidin-3-ylmethyl)-benzoyl]-hydrazinocarbonyl}-piperidine-1-Carboxylic acid tert-butyl ester, 4-{5-[4-(2-Ethyl-5,7-dimethyl-pyrazolo[1,5-a]pyrimidin-3-ylmethyl)-phenyl]-[1,3,4]oxadiazol-2-yl}-Cyclohexylamine, 4-{N'-[4-(2-Ethyl-5,7-dimethyl-pyrazolo[1,5-a]pyrimidin-3-ylmethyl)-benzoyl]-hydrazinocarbonyl}-Cyclohexyl)-Carbamic acid tert-butyl ester, 4-{1-[4-(2-Ethyl-5,7-dimethyl-pyrazolo[1,5-a]pyrimidin-3-ylmethyl)-phenyl]-1H-[1,2,3]triazol-4-ylmethyl}-piperidin-4-Ol, 1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-2-methylamino-ethanone, and (S)-1-(4-{5-[4-(2-Ethyl-5,7-dimethyl-pyrazolo[1,5-a]pyrimidin-3-ylmethyl)-phenyl]-[1,3,4]oxadiazol-2-yl}-piperidin-1-yl)-3-hydroxy-2-methylamino-propan-1-One.

11. A pharmaceutical composition comprising a compound of claim 1, or a pharmaceutically acceptable salt thereof, together with a pharmaceutically acceptable carrier.

12. A method for treating a patient susceptible to GPR4 modulation comprising administering an effective amount of a compound of claim 1, or a pharmaceutically acceptable salt thereof, thereby treating a disease or condition being selected from:
  solid tumors, rheumatoid arthritis, and inflammatory pain, visceral pain.

* * * * *